United States Patent
Lee et al.

(10) Patent No.: US 7,342,027 B2
(45) Date of Patent: Mar. 11, 2008

(54) 1-PHENYLPIPERIDIN-3-ONE DERIVATIVES AND PROCESSES FOR THE PREPARATION THEREOF

(75) Inventors: Jong Wook Lee, Kwacheon (KR); Bong Yong Lee, Suwon (KR); Chun Ho Lee, Seoul (KR); Yun Hur, Anyang (KR); Tae Dong Han, Uiwang (KR); Hyun Kyoung Ko, Iksan (KR); Suk Won Yun, Seoul (KR); Jae Young Shim, Uiwang (KR); Joong In Lim, Suwon (KR); Moon Ho Son, Suwon (KR); Jae Sung Yang, Seoul (KR); Mi Kyung Kim, Suwon (KR)

(73) Assignees: Yuhan Corporation, Seoul (KR); Dong-A Pharmaceutical Co., Ltd, Seoul (KR)

( * ) Notice: Subject to any disclaimer, the term of this patent is extended or adjusted under 35 U.S.C. 154(b) by 577 days.

(21) Appl. No.: 10/521,752

(22) PCT Filed: Jul. 26, 2003

(86) PCT No.: PCT/KR03/01502

§ 371 (c)(1),
(2), (4) Date: Jan. 19, 2005

(87) PCT Pub. No.: WO2004/011457

PCT Pub. Date: Feb. 5, 2004

(65) Prior Publication Data

US 2005/0234057 A1    Oct. 20, 2005

(30) Foreign Application Priority Data

Jul. 26, 2002   (KR) .............. 10-2002-0044164
Mar. 6, 2003    (KR) .............. 10-2003-0013889

(51) Int. Cl.
A61K 31/445   (2006.01)
C07D 451/12   (2006.01)
C07D 401/04   (2006.01)

(52) U.S. Cl. ............ 514/326; 514/237.2; 514/314; 514/318; 514/320; 514/323; 544/129; 546/168; 546/193; 546/196; 546/208; 546/209; 546/212; 546/214

(58) Field of Classification Search ............ 514/237.2, 514/314, 318, 320, 323, 326; 544/129; 546/168, 546/193, 196, 208, 209, 212, 214
See application file for complete search history.

(56) References Cited

U.S. PATENT DOCUMENTS 6,117,870 A * 9/2000 Hosoda et al. .......... 514/237.5

FOREIGN PATENT DOCUMENTS

| EP | 1 008 592 | 6/2000 |
|----|-----------|--------|
| JP | 8-92193 | 4/1996 |
| JP | 8-151394 | 6/1996 |
| JP | 10-147564 | 6/1998 |
| WO | WO 98/05336 | 2/1998 |
| WO | WO 98/08802 | 3/1998 |
| WO | WO 98/25899 | 6/1998 |
| WO | WO 98/47877 | 10/1998 |
| WO | WO 98/48799 | 11/1998 |
| WO | WO 98/49152 | 11/1998 |
| WO | WO 98/50342 | 11/1998 |
| WO | WO 98/50533 | 11/1998 |
| WO | WO 98/50534 | 11/1998 |
| WO | WO 99/11637 | 3/1999 |
| WO | WO 00/38687 | 7/2000 |
| WO | WO 00/48992 | 8/2000 |
| WO | WO 00/48993 | 8/2000 |
| WO | WO 00/49007 | 8/2000 |

OTHER PUBLICATIONS

G.J. Wells, et al., *Exp. Opin. Ther. Patents* 8(12), 1707 (1998).
S. Michaud, et al., *Exp. Opin. Ther. Patents*, 8(6), 645 (1998).
H-H Otto & T. Schirmeister, *Chem. Rev.*, 97, 133 (1997).
D. Leung et. al., *J. Med. Chem.* 43(3) 305 (2000).
Q.M. Wang, *Exp. Opin. Ther. Patents*, 8(9), 1151 (1998).
W.W. Smith, et. al., *Exp. Opin. Ther. Patents*, 9(6), 683 (1999).
W. Kim, et. al., *Exp. Opin. Ther. Patents*, 12(3), 419 (2002).
J.T. Palmer, et. al., *J. Med. Chem.*, 38, 3193 (1995).
W.R. Roush, et. al., *J. Am. Chem. Soc.*, 120, 10994 (1998).
D.S. Yamashita, et. al., *J. Am. Chem. Soc.*, 119, 11351 (1997).
S. K. Thompson, et. al., *Proc. Nacl. Acad. Sci.*, 94, 14249 (1997).
Rasnick, D. *Perspect. Drug Discov. Design*, 6, 47(1996).
M. Sato, et. al., *J. Med. Chem.*, 42, 1 (1999).
V.A. Alabaster, et. al., *J. Med. Chem.*, 30, 999 (1987).
Gregor Kopitar, et. al., *Eur. J. Biochem.*, 236, 558 (1996).

* cited by examiner

*Primary Examiner*—Celia Chang
(74) *Attorney, Agent, or Firm*—Lowe Hauptman Ham & Berner, LLP

(57) ABSTRACT

Provided are 1-phenylpiperidin-3-one derivatives and pharmaceutically acceptable salts thereof, having cysteine protease inhibitory activity, pharmaceutical compositions containing the same as an active ingredient, and processes for the preparation thereof.

10 Claims, No Drawings

# 1-PHENYLPIPERIDIN-3-ONE DERIVATIVES AND PROCESSES FOR THE PREPARATION THEREOF

BACKGROUND OF THE INVENTION

1. Field of the Invention

The present invention relates to novel 1-phenylpiperidin-3-one derivatives and pharmaceutically acceptable salts thereof having cysteine protease inhibitory activity, pharmaceutical compositions containing the same as an active ingredient, and processes for the preparation thereof.

2. Description of the Related Art

Cysteine proteases, in particular cathepsins of the papain family, participate in the normal physiological protein degradation, such as connective tissue degradation in animals, including humans. However, elevated levels of these enzymes in the body may cause various diseases. For example, it is reported that calpain protease, one of cysteine proteases, is involved in stroke and neurogdegenerative diseases, such as Alzheimer's disease [G. J. Wells, et. al., Exp. Opin. Ther. Patents, 8(12), 1707 (1998)]; cathepsin B is involved in cancer metastasis [S. Michaud, et. al., Exp. Opin. Ther. Patents, 8(6), 645 (1998)]; and cathepsin L is involved in chronic rheumatoid arthritis and osteoarthritis [H-H Otto & T. Schirmeister, Chem. Rev., 97, 133 (1997)]. International Publication Nos. WO 00/49007, WO 00/49008 and 00/48992 disclose that cathepsin S is involved in chronic obstructive pulmonary disease (COPD).

As cysteine proteases other than the papain family, caspase proteases are also known to be involved in inflammatory diseases such as osteoarthritis [D. D. Fairlie et al, J. Med. Chem. 43(3), 305 (2000)] and Rhinovirus 3C protease is involved in influenza [Q. M. Wang, Exp. Opin. Ther. Patents, 8(9), 151 (1998)].

Moreover, it is known that cathepsin K is distributed selectively in osteoblasts associated with bone resorption in a bone remodeling process and plays an important role in degradation of organic matter in bones. Accordingly, various attempts have been made to develop a novel agent for treating osteoporosis by inhibiting such proteases [W. W. Smith, et. al., Exp. Opin. Ther. Patents, 9(6), 683 (1999); W. Kim, et. al., Exp. Opin. Ther. Patent, 12(3), 419 (2002)].

For example, it has been reported that vinylsulfone group-containing peptidomimetic compounds irreversibly inhibit cysteine proteases including cathepsin K [J. T. Palmer, et. al., J. Med. Chem., 38, 3139 (1995); W. W. Roush, et. al., J. Am. Chem. Soc., 120, 10994 (1998)]. Various peptidyl or peptidomimetic compounds having 1,3-diamino-1,3-propan-2-one as a main chain have been also reported to inhibit cysteine proteases including cathepsin K [D. S. Yamashita, et. al., J. Am. Chem. Soc., 119, 11351 (1997); S. K. Thompson, et. al., Proc. Nacl. Acad. Sci., 94, 14249(1997); WO 98/08802; WO 98/48799; WO 98/49152; WO 98/50342; WO 98/50534; and WO 99/11637]. Peptidyl aldehyde (Japanese Patent Publication Nos. 8/092193, 8/151394 and 10/147,564, and WO 98/25899) and peptidyl epoxysucinamides (WO 98/47887) are proposed as irreversible cysteine protease inhibitors. WO 98/50533 proposes peptidyl 3-keto-heterocyclic derivatives, as a cathepsin K inhibitor. Further, it has been also reported that peptidyl α-ketoamides (EP 10085920); peptidyl phenylethylamines (WO 00/48993); peptidyl cycloketones (WO98/05336); and peptidyl azepines (WO 00/38687 and WO 01/34565) inhibit cysteine proteases, including cathepsin K.

However, those peptidyl compounds as known in the art readily subject to attack of proteolytic enzymes in the body, and therefore, it is difficult to develop drugs based on peptidyl compounds for treating diseases such as osteoporosis [Rasnick, D. Perspect. Drug Discov. Design, 6, 47(1996); M. Sato, et. al., J. Med. Chem., 42, 3(1999); W. W. Smith, et. al., Exp. Opin. Ther. Patents, 9(6), 683 (1999)]. Further, structural similarities in active sites of cathepsins B and L; and cathepsins K and S make it difficult to develop selective cysteine protease inhibitors each having a satisfactory selectivity to respective cathepsins, such as cathepsin B, L, K, and S [W. Kim, et. al., Exp. Opin. Ther. Patents, 12(3), 419 (2002)]. Besides, there has been a demand in the art to develop cysteine protease inhibitors having sufficient bioavailability and physicochemical stability enabling practical pharmacokinetic evaluations in oral administration.

SUMMARY OF THE INVENTION

The present invention provides a novel compound (i.e., 1-phenylpiperidin-3-one derivative) which exhibits an excellent inhibitory activity against cysteine protease, a high selective inhibition activity against cathepsin K, and a satisfactory bioavailability. Further, the present invention provides a process for preparing the 1-phenylpiperidin-3-one derivative and a pharmaceutical composition comprising the same.

In one aspect of the present invention, there is provided a 1-phenylpiperidin-3-one derivative or a pharmaceutically acceptable salt thereof.

In another aspect of the present invention, there is provided a process for preparing the 1-phenylpiperidin-3-one derivative or a pharmaceutically acceptable salt thereof, which comprises oxidizing a synthetic intermediate thereof.

In still another aspect of the present invention, there is provided an intermediate for the synthesis of the 1-phenylpiperidin-3-one derivative or a pharmaceutically acceptable salt thereof.

In still another aspect of the present invention, there is provided a process for preparing the synthetic intermediate.

In still another aspect of the present invention, there is provided a pharmaceutical composition for inhibiting cysteine proteases comprising a therapeutically effective amount of a 1-phenylpiperidin-3-one derivative or a pharmaceutically acceptable salt thereof as an active ingredient and a pharmaceutically acceptable carrier.

DETAILED DESCRIPTION OF THE INVENTION

In accordance with one aspect of the present invention, there is provided a compound of formula (I) or a pharmaceutically acceptable salt thereof:

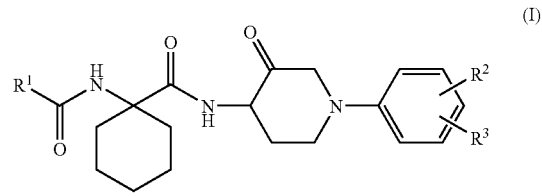

wherein:
$R^1$ is a $C_{1-6}$ alkyl group optionally substituted with phenyl, $C_{1-6}$ alkoxy, or benzyloxy; a $C_{2-6}$ alkenyl group optionally substituted with phenyl; a $C_{3-6}$ cycloalkyl group; a $C_{1-5}$ alkoxy group; a phenyl group substituted with halogen, phenyl, trifluoromethoxy, oxopyrrolidyl, mono- or di-$C_{1-4}$ alkylamino or $R^4$—$C_{1-4}$ alkoxy (wherein, $R^4$ is morpholine, pyrrolidine or piperidine); a furanyl group optionally substituted with one or more functional groups selected from the group consisting of $C_{1-6}$ alkyl, halogen, and oxopyrrolidyl; a benzofuranyl group optionally substituted with $C_{1-6}$ alkyl or $R^4$—$C_{1-4}$ alkoxy (wherein, $R^4$ is morpholine, pyrrolidine or piperidine); a thiophenyl group substituted with $C_{1-6}$ alkyl or halogen; a $C_{1-6}$ alkyl-isoxazolyl group; a pyridyl group optionally substituted with halogen; a morpholinyl group; a benzothiophenyl group; a quinolinyl group; a pyrazinyl group; a benzyloxy group; an oxopyranyl group; a $C_{1-6}$ alkyl-7H-imidazo[2,1-b]oxazolyl group; a $C_{1-6}$ alkyl-chromon-2-yl group; or a (N-t-butoxycarbonyl)piperidinyl group, and $R^2$ and $R^3$ are, each independently, hydrogen; hydroxy; nitro; halogen; cyano; a $C_{1-6}$ alkyl group optionally substituted with one or more halogen atoms; $C_{1-5}$ alkoxy; $C_{1-5}$ alkyl-thio; furyl; 1H-tetrazol-5-yl; oxazolyl; or a group selected from the formula consisting of (II), (III) and (IV):

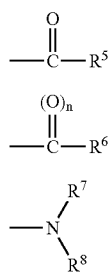

wherein, $R^5$ is hydrogen; hydroxy; $C_{1-6}$ alkyl; $C_{1-5}$ alkoxy; mono- or di-$C_{1-6}$ alkylamino; or $C_{3-6}$ cycloalkylamino, $R^6$ is $C_{1-6}$ alkyl; phenyl optionally substituted with a $C_{1-4}$ alkoxy group; benzyl optionally substituted with a $C_{1-4}$ alkoxy group, $R^7$ and $R^8$ are, each independently, hydrogen; a $C_{1-6}$ alkylcarbonyl group optionally substituted with halogen, $C_{1-4}$ alkoxy, or phenyl; $C_{2-6}$ alkenylcarbonyl; $C_{1-4}$ alkoxycarbonyl; $C_{3-6}$ cycloalkylcarbonyl; benzoyl optionally substituted with one or more halogen atoms; mono- or di-$C_{1-4}$ alkylcarbamoyl; or $C_{1-4}$ alkylsulfonyl, or bonded each ether to form a morpholine, azetidin-2-one, 3,3-dimethylazetidin-2-one, pyrrolidin-2-one, pyrrole, 2,5-dihydropyrrole, piperidin-2-one, oxazolidin-2-one, imidazolidin-2-one, imidazolidin-2,5-dione, tetrazole, 1,1-dioxoisothiazolidine, or $C_{1-6}$ alkyl-aziridin-2-one ring, and n is 0, 1, or 2.

Among the compounds of the present invention, preferred are those wherein: $R^1$ is a furanyl group optionally substituted with $C_{1-6}$ alkyl, halogen, or oxopyrrolidyl; or a benzofuranyl group optionally substituted with $C_{1-6}$ alkyl or $R^4$—$C_{1-4}$ alkoxy (wherein, $R^4$ is morpholine, pyrrolidine or piperidine) and $R^2$ and $R^3$ are, each independently, hydrogen; halogen; or a group of formula (III) or (IV).

More preferred compounds of formula (I) are listed below:

4-[N-[1-[N-(benzofuran-2-ylcarbonyl)amino]cyclohexanecarbonyl]amino]-1-(2-methanesulfonylphenyl)piperidin-3-one;

4-[N-[1-[N-(benzofuran-2-ylcarbonyl)amino]cyclohexanecarbonyl]amino]-1-(2-nitrophenyl)piperidin-3-one;

4-[N-[1-[N-(benzofuran-2-ylcarbonyl)amino]cyclohexanecarbonyl]amino]-1-(4-fluoro-2-nitrophenyl)piperidin-3-one;

4-[N-[1-[N-(benzofuran-2-ylcarbonyl)amino]cyclohexanecarbonyl]amino]-1-(5-chloro-2-nitrophenyl)piperidin-3-one;

4-[N-[1-[N-(benzofuran-2-ylcarbonyl)amino]cyclohexanecarbonyl]amino]-1-(4-methanesulfonylphenyl)piperidin-3-one;

4-[N-[1-[N-(benzofuran-2-ylcarbonyl)amino]cyclohexanecarbonyl]amino]-1-(2-acetylphenyl)piperidin-3-one;

4-[N-[1-[N-(benzofuran-2-ylcarbonyl)amino]cyclohexanecarbonyl]amino]-1-(4-cyanophenyl)piperidin-3-one;

4-[N-[1-[N-(benzofuran-2-ylcarbonyl)amino]cyclohexanecarbonyl]amino]-1-(2-cyano-3-fluorophenyl)piperidin-3-one;

4-[N-[1-[N-(benzofuran-2-ylcarbonyl)amino]cyclohexanecarbonyl]amino]-1-(2-cyano-6-fluorophenyl)piperidin-3-one;

4-[N-[1-[N-(benzofuran-2-ylcarbonyl)amino]cyclohexanecarbonyl]amino]-1-(2-cyano-5-fluorophenyl)piperidin-3-one;

4-[N-[1-[N-(benzofuran-2-ylcarbonyl)amino]cyclohexanecarbonyl]amino]-1-(3-cyano-5-fluorophenyl)piperidin-3-one;

4-[N-[1-[N-(benzofuran-2-ylcarbonyl)amino]cyclohexanecarbonyl]amino]-1-(2-ethanesulfonylphenyl)piperidin-3-one;

4-[N-[1-[N-(benzofuran-2-ylcarbonyl)amino]cyclohexanecarbonyl]amino]-1-(4-acetylphenyl)piperidin-3-one;

4-[N-[1-[N-(benzofuran-2-ylcarbonyl)amino]cyclohexanecarbonyl]amino]-1-(4-formylphenyl)piperidin-3-one;

4-[N-[1-[N-(benzofuran-2-ylcarbonyl)amino]cyclohexanecarbonyl]amino]-1-(2-formylphenyl)piperidin-3-one;

4-[N-[1-[N-(benzofuran-2-ylcarbonyl)amino]cyclohexanecarbonyl]amino]-1-(4-nitrophenyl)piperidin-3-one;

4-[N-[1-[N-(benzofuran-2-ylcarbonyl)amino]cyclohexanecarbonyl]amino]-1-(3-methyl-4-nitrophenyl)piperidin-3-one;

4-[N-[1-[N-(benzofuran-2-ylcarbonyl)amino]cyclohexanecarbonyl]amino]-1-(3-fluoro-2-formylphenyl)piperidin-3-one;

4-[N-[1-[N-(benzofuran-2-ylcarbonyl)amino]cyclohexanecarbonyl]amino]-1-(3-chloro-2-formylphenyl)piperidin-3-one;

4-[N-[1-[N-(benzofuran-2-ylcarbonyl)amino]cyclohexanecarbonyl]amino]-1-(2-formyl-4-nitrophenyl)piperidin-3-one;

4-[N-[1-[N-(benzofuran-2-ylcarbonyl)amino]cyclohexanecarbonyl]amino]-1-(2-formyl-6-fluorophenyl)piperidin-3-one;

4-[N-[1-[N-(benzofuran-2-ylcarbonyl)amino]cyclohexanecarbonyl]amino]-1-(2-fluoro-3-formylphenyl)piperidin-3-one;

4-[N-[1-[N-(benzofuran-2-ylcarbonyl)amino]cyclohexanecarbonyl]amino]-1-(2-isopropylsulfonylphenyl)piperidin-3-one;

4-[N-[1-[N-(benzofuran-2-ylcarbonyl)amino]cyclohexanecarbonyl]amino]-1-(4-fluoro-2-trifluoromethylphenyl)piperidin-3-one;

4-[N-[1-[N-(benzofuran-2-ylcarbonyl)amino]cyclohexan- ecarbonyl]amino]-1-(2-cyanophenyl)piperidin-3-one;
4-[N-[1-[N-(benzofuran-2-ylcarbonyl)amino]cyclohexan- ecarbonyl]amino]-1-[2-(4-morpholino)phenyl]piperidin- 3-one;
4-[N-[1-[N-(benzofuran-2-ylcarbonyl)amino]cyclohexan- ecarbonyl]amino]-1-(2-ethoxyphenyl)piperidin-3-one;
4-[N-[1-[N-(benzofuran-2-ylcarbonyl)amino]cyclohexan- ecarbonyl]amino]-1-(2-fluoro-4-trifluoromethylphenyl) piperidin-3-one;
4-[N-[1-[N-(benzofuran-2-ylcarbonyl)amino]cyclohexan- ecarbonyl]amino]-1-(2-chloro-4-trifluoromethylphenyl) piperidin-3-one;
4-[N-[1-[N-(benzofuran-2-ylcarbonyl)amino]cyclohexan- ecarbonyl]amino]-1-(2,4-dichlorophenyl)piperidin-3- one;
4-[N-[1-[N-(benzofuran-2-ylcarbonyl)amino]cyclohexan- ecarbonyl]amino]-1-(4-chloro-2-fluorophenyl)piperidin- 3-one;
4-[N-[1-[N-(benzofuran-2-ylcarbonyl)amino]cyclohexan- ecarbonyl]amino]-1-(2-methoxy-5-cyanophenyl)piperi- din-3-one;
4-[N-[1-[N-(benzofuran-2-ylcarbonyl)amino]cyclohexan- ecarbonyl]amino]-1-(4-cyano-2-fluorophenyl)piperidin- 3-one;
4-[N-[1-[N-(benzofuran-2-ylcarbonyl)amino]cyclohexan- ecarbonyl]amino]-1-[2-(2-furyl)phenyl]piperidin-3-one;
4-[N-[1-[N-(benzofuran-2-ylcarbonyl)amino]cyclohexan- ecarbonyl]amino]-1-(2-bromophenyl)piperidin-3-one;
4-[N-[1-[N-(benzofuran-2-ylcarbonyl)amino]cyclohexan- ecarbonyl]amino]-1-(2-methylthiophenyl)piperidin-3- one;
4-[N-[1-[N-(benzofuran-2-ylcarbonyl)amino]cyclohexan- ecarbonyl]amino]-1-[2-(tert-butoxycarbonyl)phenyl]pip- eridin-3-one;
4-[N-[1-[N-(benzofuran-2-ylcarbonyl)amino]cyclohexan- ecarbonyl]amino]-1-(2-ethoxycarbonylphenyl)piperidin- 3-one;
4-[N-[1-[N-(benzofuran-2-ylcarbonyl)amino]cyclohexan- ecarbonyl]amino]-1-(2-methoxyphenyl)piperidin-3-one;
4-[N-[1-[N-(benzofuran-2-ylcarbonyl)amino]cyclohexan- ecarbonyl]amino]-1-(4-fluoro-2-methylphenyl)piperidin- 3-one;
4-[N-[1-[N-(benzofuran-2-ylcarbonyl)amino]cyclohexan- ecarbonyl]amino]-1-(2-isopropoxyphenyl)piperidin-3- one;
4-[N-[1-[N-(benzofuran-2-ylcarbonyl)amino]cyclohexan- ecarbonyl]amino]-1-(2-ethylthiophenyl)piperidin-3-one;
4-[N-[1-[N-(benzofuran-2-ylcarbonyl)amino]cyclohexan- ecarbonyl]amino]-1-[2-(3,3-dimethylazetidin-2-one-1-yl) phenyl]piperidin-3-one;
4-[N-[1-[N-(benzofuran-2-ylcarbonyl)amino]cyclohexan- ecarbonyl]amino]-1-[2-(pyrrolidin-2-one-1-yl)phenyl]pi- peridin-3-one;
4-[N-[1-[N-(benzofuran-2-ylcarbonyl)amino]cyclohexan- ecarbonyl]amino]-1-[2-(piperidin-2-one-1-yl)phenyl]pip- eridin-3-one;
4-[N-[1-[N-(benzofuran-2-ylcarbonyl)amino]cyclohexan- ecarbonyl]amino]-1-[2-(2-oxazolidinon-1-yl)phenyl]pip- eridin-3-one;
4-[N-[1-[N-(benzofuran-2-ylcarbonyl)amino]cyclohexan- ecarbonyl]amino]-1-[2-(2-imidazolidinon-1-yl)phenyl] piperidin-3-one;
4-[N-[1-[N-(benzofuran-2-ylcarbonyl)amino]cyclohexan- ecarbonyl]amino]-1-[2-[N-(ethoxycarbonyl)amino]phe- nyl]piperidin-3-one;
4-[N-[1-[N-(benzofuran-2-ylcarbonyl)amino]cyclohexan- ecarbonyl]amino]-1-[2-[N-(methoxycarbonyl)amino] phenyl]piperidin-3-one;
4-[N-[1-[N-(benzofuran-2-ylcarbonyl)amino]cyclohexan- ecarbonyl]amino]-1-[2-[N-(4-chlorobutyryl)amino]phe- nyl]piperidin-3-one;
4-[N-[1-[N-(benzofuran-2-ylcarbonyl)amino]cyclohexan- ecarbonyl]amino]-1-[2-[N-(isobutyryl)amino]phenyl]pi- peridin-3-one;
4-[N-[1-[N-(benzofuran-2-ylcarbonyl)amino]cyclohexan- ecarbonyl]amino]-1-[2-[N-(methoxyacetyl)amino]phe- nyl]piperidin-3-one;
4-[N-[1-[N-(benzofuran-2-ylcarbonyl)amino]cyclohexan- ecarbonyl]amino]-1-[2-[N-(cyclopropanecarbonyl) amino]phenyl]piperidin-3-one;
4-[N-[1-[N-(benzofuran-2-ylcarbonyl)amino]cyclohexan- ecarbonyl]amino]-1-[2-[N-(3-phenylpropionyl)amino] phenyl]piperidin-3-one;
4-[N-[1-[N-(benzofuran-2-ylcarbonyl)amino]cyclohexan- ecarbonyl]amino]-1-[2-[N-(2-fluorobenzoyl)amino]phe- nyl]piperidin-3-one;
4-[N-[1-[N-(benzofuran-2-ylcarbonyl)amino]cyclohexan- ecarbonyl]amino]-1-[2-[N-(acetyl)amino]phenyl]piperi- din-3-one;
4-[N-[1-[N-(benzofuran-2-ylcarbonyl)amino]cyclohexan- ecarbonyl]amino]-1-[2-(2,5-dihydropyrrol-1-yl)phenyl] piperidin-3-one;
4-[N-[1-[N-(benzofuran-2-ylcarbonyl)amino]cyclohexan- ecarbonyl]amino]-1-[2-(tetrazol-1-yl)phenyl]piperidin-3- one;
4-[N-[1-[N-(benzofuran-2-ylcarbonyl)amino]cyclohexan- ecarbonyl]amino]-1-[2-(pyrrol-1-yl)-5-fluorophenyl]pip- eridin-3-one;
4-[N-[1-[N-(benzofuran-2-ylcarbonyl)amino]cyclohexan- ecarbonyl]amino]-1-[2-(pyrrol-1-yl)phenyl]piperidin-3- one;
4-[N-[1-[N-(benzofuran-2-ylcarbonyl)amino]cyclohexan- ecarbonyl]amino]-1-[2-(N,N-dimethylcarbamoyl)phenyl] piperidin-3-one;
4-[N-[1-[N-(benzofuran-2-ylcarbonyl)amino]cyclohexan- ecarbonyl]amino]-1-[2-(N-methylcarbamoyl)phenyl]pip- eridin-3-one;
4-[N-[1-[N-(benzofuran-2-ylcarbonyl)amino]cyclohexan- ecarbonyl]amino]-1-(2-carboxyphenyl)piperidin-3-one;
4-[N-[1-[N-(benzofuran-2-ylcarbonyl)amino]cyclohexan- ecarbonyl]amino]-1-(4-carboxyphenyl)piperidin-3-one;
4-[N-[1-[N-(benzofuran-2-ylcarbonyl)amino]cyclohexan- ecarbonyl]amino]-1-[2-(1,3-oxazol-5-yl)phenyl]piperi- din-3-one;
4-[N-[1-[N-(benzofuran-2-ylcarbonyl)amino]cyclohexan- ecarbonyl]amino]-1-(2-hydroxyphenyl)piperidin-3-one;
4-[N-[1-[N-(benzofuran-2-ylcarbonyl)amino]cyclohexan- ecarbonyl]amino]-1-[2-(1H-tetrazol-5-yl)phenyl]piperi- din-3-one;
4-[N-[1-[N-(benzofuran-2-ylcarbonyl)amino]cyclohexan- ecarbonyl]amino]-1-(2-methylsulfinylphenyl)piperidin- 3-one;
4-[N-[1-[N-(benzofuran-2-ylcarbonyl)amino]cyclohexan- ecarbonyl]amino]-1-(2-ethylsulfinylphenyl)piperidin-3- one;
4-[N-[1-[N-(benzofuran-2-ylcarbonyl)amino]cyclohexan- ecarbonyl]amino]-1-(2-isopropylsulfinylphenyl)piperi- din-3-one;
4-[N-[1-[N-(benzofuran-2-ylcarbonyl)amino]cyclohexan- ecarbonyl]amino]-1-[2-N-(acryloyl)aminophenyl]piperi- din-3-one;

4-[N-[1-[N-(benzofuran-2-ylcarbonyl)amino]cyclohexanecarbonyl]amino]-1-[2-(3,3-dimethylureido)phenyl]piperidin-3-one;

4-[N-[1-[N-(benzofuran-2-ylcarbonyl)amino]cyclohexanecarbonyl]amino]-1-[2-(methoxycarbonyl)phenyl]piperidin-3-one;

4-[N-[1-[N-(benzofuran-2-ylcarbonyl)amino]cyclohexanecarbonyl]amino]-1-phenylpiperidin-3-one;

4-[N-[1-[N-(benzofuran-2-ylcarbonyl)amino]cyclohexanecarbonyl]amino]-1-[2-(1,1-dioxo-isothiazolin-2-yl)phenyl]piperidin-3-one;

4-[N-[1-[N-(furan-2-ylcarbonyl)amino]cyclohexylcarbonyl]amino]-1-(2-methanesulfonylphenyl)piperidin-3-one;

4-[N-[1-[N-(furan-2-ylcarbonyl)amino]cyclohexylcarbonyl]amino]-1-(3-fluoro-2-methanesulfonyphenyl)piperidin-3-one;

4-[N-[1-[N-(furan-2-ylcarbonyl)amino]cyclohexylcarbonyl]amino]-1-(4-fluoro-2-nitrophenyl)piperidin-3-one;

4-[N-[1-[N-(furan-2-ylcarbonyl)amino]cyclohexylcarbonyl]amino]-1-(4-fluoro-2-formylphenyl)piperidin-3-one;

4-[N-[1-[N-(furan-2-ylcarbonyl)amino]cyclohexylcarbonyl]amino]-1-(2-isopropylsulfonylphenyl)piperidin-3-one;

4-[N-[1-[N-(furan-2-ylcarbonyl)amino]cyclohexanecarbonyl]amino]-1-(2-phenylsulfonylphenyl)piperidin-3-one;

4-[N-[1-[N-(furan-2-ylcarbonyl)amino]cyclohexanecarbonyl]amino]-1-(2-(4-methoxybenzylsulfonylphenyl)piperidin-3-one;

4-[N-[1-[N-(furan-2-ylcarbonyl)amino]cyclohexylcarbonyl]amino]-1-(4-fluoro-2-methanesulfonylphenyl)piperidin-3-one;

4-[N-[1-[N-(furan-2-ylcarbonyl)amino]cyclohexylcarbonyl]amino]-1-(4-methoxy-2-methanesulfonylphenyl)piperidin-3-one;

4-[N-[1-[N-(furan-2-ylcarbonyl)amino]cyclohexylcarbonyl]amino]-1-(4-fluoro-2-thiomethoxyphenyl)piperidin-3-one;

4-[N-[1-[N-(furan-2-ylcarbonyl)amino]cyclohexylcarbonyl]amino]-1-(2-cyanophenyl)piperidin-3-one;

4-[N-[1-[N-(furan-2-ylcarbonyl)amino]cyclohexylcarbonyl]amino]-1-(4-fluoro-2-methoxyacetylaminophenyl)piperidin-3-one;

4-[N-[1-[N-(furan-2-ylcarbonyl)amino]cyclohexylcarbonyl]amino]-1-(4-fluoro-2-methoxycarbonylaminophenyl)piperidin-3-one;

4-[N-[1-[N-(furan-2-ylcarbonyl)amino]cyclohexylcarbonyl]amino]-1-(4-fluoro-2-cyclopropylcarbonylaminophenyl)piperidin-3-one;

4-[N-[1-[N-(furan-2-ylcarbonyl)amino]cyclohexylcarbonyl]amino]-1-(4-fluoro-2-isobutyrylaminophenyl)piperidin-3-one;

4-[N-[1-[N-(furan-2-ylcarbonyl)amino]cyclohexylcarbonyl]amino]-1-[4-fluoro-2-(4-chlorobutyryl)aminophenyl]piperidin-3-one;

4-[N-[1-[N-(furan-2-ylcarbonyl)amino]cyclohexylcarbonyl]amino]-1-[4-fluoro-2-(3,3-dimethylazetidin-2-one-1-yl)phenyl]piperidin-3-one;

4-[N-[1-[N-(furan-2-ylcarbonyl)amino]cyclohexanecarbonyl]amino]-1-[4-fluoro-2-(3-methyl-aziridin-2-one-1-yl)phenyl]piperidin-3-one;

4-[N-[1-[N-(furan-2-ylcarbonyl)amino]cyclohexanecarbonyl]amino]-1-[4-fluoro-2-(azetidin-2-one-1-yl)phenyl]piperidin-3-one;

4-[N-[1-[N-(furan-2-ylcarbonyl)amino]cyclohexylcarbonyl]amino]-1-[4-fluoro-2-(pyrrolidin-2-one-1-yl)phenyl]piperidin-3-one;

4-[N-[1-[N-(furan-2-ylcarbonyl)amino]cyclohexanecarbonyl]amino]-1-[4-fluoro-2-(1,3-imidazolidin-2,5-dione-1-yl)phenyl]piperidin-3-one;

4-[N-[1-[N-(furan-2-ylcarbonyl)amino]cyclohexylcarbonyl]amino]-1-[4-fluoro-2-(1,1-dioxo-isothiazolidin-2-yl)phenyl]piperidin-3-one;

4-[N-[1-[N-(furan-2-ylcarbonyl)amino]cyclohexylcarbonyl]amino]-1-[4-fluoro-2-(piperidin-2-one-1-yl)phenyl]piperidin-3-one;

4-[N-[1-[N-(furan-2-ylcarbonyl)amino]cyclohexylcarbonyl]amino]-1-[4-fluoro-2-(pyrrol-1-yl)]piperidin-3-one;

4-[N-[1-[N-(furan-2-ylcarbonyl)amino]cyclohexylcarbonyl]amino]-1-[4-fluoro-2-(oxazol-4-yl)phenyl]piperidin-3-one;

4-[N-[1-[N-(furan-2-ylcarbonyl)amino]cyclohexylcarbonyl]amino]-1-[4-fluoro-2-(N-methylcarbamoyl)phenyl]piperidin-3-one;

4-[N-[1-[N-(furan-2-ylcarbonyl)amino]cyclohexylcarbonyl]amino]-1-[2-(N,N-dimethylcarbamoyl)phenyl]piperidin-3-one;

4-[N-[1-[N-(furan-2-ylcarbonyl)amino]cyclohexylcarbonyl]amino]-1-[2-(N-cyclopropylcarbamoyl)phenyl]piperidin-3-one;

4-[N-[1-[N-(5-methyl-isoxazol-3-ylcarbonyl)amino]cyclohexylcarbonyl]amino]-1-(2-aminophenyl)piperidin-3-one;

4-[N-[1-[N-(5-methyl-isoxazol-3-ylcarbonyl)amino]cyclohexylcarbonyl]amino]-1-(2-nitrophenyl)piperidin-3-one;

4-[N-[1-[N-(5-methyl-isoxazol-3-ylcarbonyl)amino]cyclohexylcarbonyl]amino]-1-(2-methanesulfonylphenyl)piperidin-3-one;

4-[N-[1-[N-(5-methyl-isoxazol-3-ylcarbonyl)amino]cyclohexylcarbonyl]amino]-1-(2-ethanesulfonylphenyl)piperidin-3-one;

4-[N-[1-[N-(5-methyl-isoxazol-3-ylcarbonyl)amino]cyclohexylcarbonyl]amino]-1-[4-fluoro-2-(3,3-dimethyl-azetidin-2-one-1-yl)phenyl]piperidin-3-one;

4-[N-[1-[N-(5-methyl-isoxazol-3-ylcarbonyl)amino]cyclohexylcarbonyl]amino]-1-[4-fluoro-2-(pyrrolidin-2-one-1-yl)phenyl]piperidin-3-one;

4-[N-[1-[N-(5-methyl-isoxazol-3-ylcarbonyl)amino]cyclohexylcarbonyl]amino]-1-[4-fluoro-2-(oxazolidin-2-one-3-yl)phenyl]piperidin-3-one;

4-[N-[1-[N-(5-methyl-isoxazol-3-ylcarbonyl)amino]cyclohexylcarbonyl]amino]-1-[4-fluoro-2-(imidazolidin-2-one-1-yl)phenyl]piperidin-3-one;

4-[N-[1-[N-(5-methyl-isoxazol-3-ylcarbonyl)amino]cyclohexylcarbonyl]amino]-1-[2-(3,3-dimethyl-azetidin-2-one-1-yl)phenyl]piperidin-3-one;

4-[N-[1-[N-(5-methyl-isoxazol-3-ylcarbonyl)amino]cyclohexylcarbonyl]amino]-1-[2-(pyrrolidin-2-one-1-yl)phenyl]piperidin-3-one;

4-[N-[1-[N-(5-chloro-thiophen-2-ylcarbonyl)amino]cyclohexylcarbonyl]amino]-1-(2-methanesulfonylphenyl)piperidin-3-one;

4-[N-[1-[N-(5-chloro-thiophen-2-ylcarbonyl)amino]cyclohexylcarbonyl]amino]-1-(2-ethanesulfonylphenyl)piperidin-3-one;

4-[N-[1-[N-(5-chloro-thiophen-2-ylcarbonyl)amino]cyclohexylcarbonyl]amino]-1-(2-isopropanesulfonylphenyl)piperidin-3-one;

4-[N-[1-[N-(5-chloro-thiophen-2-ylcarbonyl)amino]cyclohexylcarbonyl]amino]-1-(5-fluoro-2-methanesulfonylphenyl)piperidin-3-one;

4-[N-[1-[N-(5-methyl-thiophen-2-ylcarbonyl)amino]cyclohexylcarbonyl]amino]-1-(2-methanesulfonylphenyl)piperidin-3-one;

4-[N-[1-[N-(5-methyl-thiophen-2-ylcarbonyl)amino]cyclohexanecarbonyl]amino]-1-(2-isopropanesulfonylphenyl)piperidin-3-one;
4-[N-[1-[N-(5-methyl-thiophen-2-ylcarbonyl)amino]cyclohexylcarbonyl]amino]-1-(5-fluoro-2-methanesulfonylphenyl)piperidin-3-one;
4-[N-[1-[N-(3-methyl-thiophen-2-ylcarbonyl)amino]cyclohexylcarbonyl]amino]-1-(2-methanesulfonylphenyl)piperidin-3-one;
4-[N-[1-[N-(2-methyl-furan-3-ylcarbonyl)amino]cyclohexylcarbonyl]amino]-1-(2-methanesulfonylphenyl)piperidin-3-one;
4-[N-[1-[N-(5-methyl-furan-2-ylcarbonyl)amino]cyclohexylcarbonyl]amino]-1-(2-methanesulfonylphenyl)piperidin-3-one;
4-[N-[1-[N-(5-bromo-furan-2-ylcarbonyl)amino]cyclohexylcarbonyl]amino]-1-(2-methanesulfonyl-4-methoxyphenyl)piperidin-3-one;
4-[N-[1-[N-(4,5-dimethyl-furan-2-ylcarbonyl)amino]cyclohexylcarbonyl]amino]-1-(2-methanesulfonylphenyl)piperidin-3-one;
4-[N-[1-[N-(4,5-dimethyl-furan-2-ylcarbonyl)amino]cyclohexylcarbonyl]amino]-1-[2-(pyrrolidin-2-one-1-yl)phenyl]piperidin-3-one;
4-[N-[1-[N-(morpholin-4-ylcarbonyl)amino]cyclohexylcarbonyl]amino]-1-(2-methanesulfonylphenyl)piperidin-3-one;
4-[N-[1-[N-(benzothiophen-2-ylcarbonyl)amino]cyclohexylcarbonyl]amino]-1-(2-methanesulfonylphenyl)piperidin-3-one;
4-[N-[1-[N-(benzothiophen-2-ylcarbonyl)amino]cyclohexylcarbonyl]amino]-1-(2-tert-butoxycarbonylphenyl)piperidin-3-one;
4-[N-[1-[N-(benzothiophen-2-ylcarbonyl)amino]cyclohexylcarbonyl]amino]-1-(2-chloro-5-trifluoromethylphenyl)piperidin-3-one;
4-[N-[1-[N-(benzothiophen-2-ylcarbonyl)amino]cyclohexylcarbonyl]amino]-1-(4-chloro-2-fluoro-phenyl)piperidin-3-one;
4-[N-[1-[N-(benzothiophen-2-ylcarbonyl)amino]cyclohexylcarbonyl]amino]-1-(2-methylphenyl)piperidin-3-one;
4-[N-[1-[N-(3-methyl-benzofuran-2-ylcarbonyl)amino]cyclohexylcarbonyl]amino]-1-(2-methanesulfonylphenyl)piperidin-3-one;
4-[N-[1-[N-(3-methyl-benzofuran-2-ylcarbonyl)amino]cyclohexylcarbonyl]amino]-1-(5-fluoro-2-trifluoromethylphenyl)piperidin-3-one;
4-[N-[1-[N-(3-methyl-benzofuran-2-ylcarbonyl)amino]cyclohexylcarbonyl]amino]-1-(5-cyano-2-methoxyphenyl)piperidin-3-one;
4-[N-[1-[N-(quinolin-2-ylcarbonyl)amino]cyclohexylcarbonyl]amino]-1-(2-methanesulfonylphenyl)piperidin-3-one;
4-[N-[1-[N-(quinolin-2-ylcarbonyl)amino]cyclohexylcarbonyl]amino]-1-[2-(pyrrolidin-2-one-1-yl)phenyl]piperidin-3-one;
4-[N-[1-[N-(quinolin-2-ylcarbonyl)amino]cyclohexylcarbonyl]amino]-1-(2-nitrophenyl)piperidin-3-one;
4-[N-[1-[N-(pyrazin-2-ylcarbonyl)amino]cyclohexylcarbonyl]amino]-1-(2-methanesulfonylphenyl)piperidin-3-one;
4-[N-[1-[N-(pyrazin-2-ylcarbonyl)amino]cyclohexylcarbonyl]amino]-1-(2-methanesulfonylphenyl)piperidin-3-one dihydrochloride;
4-[N-[1-[N-(isonicotinylcarbonyl)amino]cyclohexylcarbonyl]amino]-1-(2-methanesulfonylphenyl)piperidin-3-one;
4-[N-[1-[N-(6-chloronicotinylcarbonyl)amino]cyclohexylcarbonyl]amino]-1-(2-methanesulfonylphenyl)piperidin-3-one;
4-[N-[1-[N-(6-chloronicotinylcarbonyl)amino]cyclohexylcarbonyl]amino]-1-(4-fluoro-2-nitrophenyl)piperidin-3-one;
4-[N-[1-[N-(pyridin-2-carbonyl)amino]cyclohexylcarbonyl]amino]-1-(2-methanesulfonylphenyl)piperidin-3-one;
4-[N-[1-[N-(pyridin-2-carbonyl)amino]cyclohexylcarbonyl]amino]-1-(2-methanesulfonylphenyl)piperidin-3-one hydrochloride;
4-[N-[1-[N-(4-fluorobenzoyl)amino]cyclohexylcarbonyl]amino]-1-(2-methanesulfonylphenyl)piperidin-3-one;
4-[N-[1-[N-(4-fluorobenzoyl)amino]cyclohexylcarbonyl]amino]-1-(4-fluoro-2-methanesulfonylphenyl)piperidin-3-one;
4-[N-[1-[N-(4-fluorobenzoyl)amino]cyclohexylcarbonyl]amino]-1-(2-methanesulfonyl-4-methoxyphenyl)piperidin-3-one;
4-[N-[1-[N-(4-fluorobenzoyl)amino]cyclohexanecarbonyl]amino]-1-(4-fluoro-2-trifluoromethylphenyl)piperidin-3-one;
4-[N-[1-[N-(4-fluorobenzoyl)amino]cyclohexanecarbonyl]amino]-1-[(2-(3-phenylpropionylamino)phenyl)piperidin-3-one;
4-[N-[1-[N-(4-fluorobenzoyl)amino]cyclohexanecarbonyl]amino]-1-[2-(cyclopropylamino)phenyl]piperidin-3-one;
4-[N-[1-[N-(4-fluorobenzoyl)amino]cyclohexanecarbonyl]amino]-1-[4-fluoro-2-(2,3,4-trifluorobenzoylamino)phenyl]piperidin-3-one;
4-[N-[1-[N-(4-biphenylcarbonyl)amino]cyclohexanecarbonyl]amino]-1-(2-methanesulfonylphenyl)piperidin-3-one;
4-[N-[1-[N-(4-trifluoromethylbenzoyl)amino]cyclohexanecarbonyl]amino]-1-(2-methanesulfonylphenyl)piperidin-3-one;
4-[N-[1-[N-(4-(2-morpholinethoxy)benzoyl)amino]cyclohexanecarbonyl]amino]-1-(2-methanesulfonylphenyl)piperidin-3-one;
4-[N-[1-[N-(4-(2-pyrrolidinethoxy)benzoyl)amino]cyclohexanecarbonyl]amino]-1-(2-methanesulfonylphenyl)piperidin-3-one;
4-[N-[1-[N-(4-(2-piperidinethoxy)benzoyl)amino]cyclohexanecarbonyl]amino]-1-(2-methanesulfonylphenyl)piperidin-3-one;
4-[N-[1-[N-(4-(2-morpholinethoxy)benzoyl)amino]cyclohexanecarbonyl]amino]-1-(2-methanesulfonylphenyl)piperidin-3-one hydrochloride;
4-[N-[1-[N-(4-(2-pyrrolidinethoxy)benzoyl)amino]cyclohexanecarbonyl]amino]-1-(2-methanesulfonylphenyl)piperidin-3-one hydrochloride;
4-[N-[1-[N-(4-(2-piperidinethoxy)benzoyl)amino]cyclohexanecarbonyl]amino]-1-(2-methanesulfonylphenyl)piperidin-3-one hydrochloride;
4-[N-[1-[N-(5-(2-morpholinethoxy)benzofuran-2-ylcarbonyl)amino]cyclohexanecarbonyl]amino]-1-(2-methanesulfonylphenyl)piperidin-3-one;
4-[N-[1-[N-(5-(2-pyrrolidinethoxy)benzofuran-2-ylcarbonyl)amino]cyclohexanecarbonyl]amino]-1-(2-methanesulfonylphenyl)piperidin-3-one;
4-[N-[1-[N-(5-(2-piperidinethoxy)benzofuran-2-ylcarbonyl)amino]cyclohexanecarbonyl]amino]-1-(2-methanesulfonylphenyl)piperidin-3-one;
4-[N-[1-[N-(5-(2-morpholinethoxy)benzofuran-2-ylcarbonyl)amino]cyclohexanecarbonyl]amino]-1-(2-methanesulfonylphenyl)piperidin-3-one hydrochloride;

4-[N-[1-[N-(5-(2-pyrrolidinethoxy)benzofuran-2-ylcarbonyl)amino]cyclohexanecarbonyl]amino]-1-(2-methanesulfonylphenyl)piperidin-3-one hydrochloride;

4-[N-[1-[N-(5-(2-piperidinethoxy)benzofuran-2-ylcarbonyl)amino]cyclohexanecarbonyl]amino]-1-(2-methanesulfonylphenyl)piperidin-3-one hydrochloride;

4-[N-[1-[N-(4-(2-oxopyrrolidine)benzoyl)amino]cyclohexanecarbonyl]amino]-1-(2-methanesulfonylphenyl)piperidin-3-one;

4-[N-[1-[N-(4-(2-oxopyrrolidine)furan-2-ylcarbonyl)amino]cyclohexanecarbonyl]amino]-1-(2-methanesulfonylphenyl)piperidin-3-one;

4-[N-[1-[N-(4-(2-morpholinethoxy)benzoyl)amino]cyclohexanecarbonyl]amino]-1-(4-fluoro-2-methanesulfonylaminophenyl)piperidin-3-one;

4-[N-[1-[N-(4-(2-morpholinethoxy)benzoyl)amino]cyclohexanecarbonyl]amino]-1-[4-fluoro-2-(pyrrolidin-2-one-1-yl)phenyl]piperidin-3-one;

4-[N-[1-[N-(4-(dimethylamino)benzoyl)amino]cyclohexanecarbonyl]amino]-1-(4-fluoro-2-methanesulfonylphenyl)piperidin-3-one;

4-[N-[1-[N-(4-(diethylamino)benzoyl)amino]cyclohexanecarbonyl]amino]-1-(4-fluoro-2-methanesulfonylphenyl)piperidin-3-one;

4-[N-[1-[N-(4-(dimethylamino)benzoyl)amino]cyclohexanecarbonyl]amino]-1-(4-fluoro-2-methanesulfonylphenyl)piperidin-3-one hydrochloride;

4-[N-[1-[N-(4-(diethylamino)benzoyl)amino]cyclohexanecarbonyl]amino]-1-(4-fluoro-2-methanesulfonylphenyl)piperidin-3-one hydrochloride;

4-[N-[1-[N-(3-phenylpropionyl)amino]cyclohexylcarbonyl]amino]-1-(2-methanesulfonylphenyl)piperidin-3-one;

4-[N-[1-[N-(2-methylcinnamoyl)amino]cyclohexanecarbonyl]amino]-1-(2-methanesulfonylphenyl)piperidin-3-one;

4-[N-[1-[N-(benzyloxycarbonyl)amino]cyclohexylcarbonyl]amino]-1-(2-acetylamino)piperidin-3-one;

4-[N-[1-[N-(benzyloxycarbonyl)amino]cyclohexylcarbonyl]amino]-1-(2-trifluoromethylphenyl)piperidin-3-one;

4-[N-[1-[N-(2-pyran-2-one-5-ylcarbonyl)amino]cyclohexanecarbonyl]amino]-1-(2-methanesulfonylphenyl)piperidin-3-one;

4-[N-[1-[N-((6-methyl)-7H-imidazo[2,1-b]oxazol-5-ylcarbonyl)amino]cyclohexanecarbonyl]amino]-1-(2-methanesulfonylphenyl)piperidin-3-one;

4-[N-[1-[N-((6-methyl)-chromon-2-ylcarbonyl)amino]cyclohexanecarbonyl]amino]-1-(2-methanesulfonylphenyl)piperidin-3-one;

4-[N-[1-[N-(isobutyryl)amino]cyclohexanecarbonyl]amino]-1-(2-methanesulfonylphenyl)piperidin-3-one;

4-[N-[1-[N-(isovaleryl)amino]cyclohexanecarbonyl]amino]-1-(2-methanesulfonylphenyl)piperidin-3-one;

4-[N-[1-[N-(3,3-dimethylacryloyl)amino]cyclohexanecarbonyl]amino]-1-(2-methanesulfonylphenyl)piperidin-3-one;

4-[N-[1-[N-(2-methoxyacetyl)amino]cyclohexanecarbonyl]amino]-1-(2-methanesulfonylphenyl)piperidin-3-one;

4-[N-[1-[N-(cyclopropanecarbonyl)amino]cyclohexanecarbonyl]amino]-1-(2-methanesulfonylphenyl)piperidin-3-one;

4-[N-[1-[N-(cyclobutanecarbonyl)amino]cyclohexanecarbonyl]amino]-1-(2-methanesulfonylphenyl)piperidin-3-one;

4-[N-[1-[N-(cyclopentanecarbonyl)amino]cyclohexanecarbonyl]amino]-1-(2-methanesulfonylphenyl)piperidin-3-one;

4-[N-[1-[N-(cyclohexanecarbonyl)amino]cyclohexanecarbonyl]amino]-1-(2-methanesulfonylphenyl)piperidin-3-one;

4-[N-[1-[N-((3-isobutyloxy)propionyl)amino]cyclohexanecarbonyl]amino]-1-(2-methanesulfonylphenyl)piperidin-3-one;

4-[N-[1-[N-((3-benzyloxy)propionyl)amino]cyclohexanecarbonyl]amino]-1-(2-methanesulfonylphenyl)piperidin-3-one;

4-[N-[1-[N-((N-t-butoxycarbonyl)piperidin-4-ylcarbonyl)amino]cyclohexanecarbonyl]amino]-1-(2-methanesulfonylphenyl)piperidin-3-one.

Furthermore, the present invention encompasses within its scope those pharmaceutically acceptable salts of the compounds of formula (I). The pharmaceutically acceptable salts which fall within the scope of the present invention include organic acid salts or inorganic acid salts, such as hydrochloride, hydrobromide, sulfate, sulfarmate, phosphate, nitrate, acetate, propionate, succinate, glycolate, stearate, malate, hydroxymalate, phenylacetate, glutamate, benzoate, salisylate, sulfanylate, 2-acetoxy-benzoate, fumarate, toluenesulfonate, methanedisulfonate, ethanedisulfonate, oxalate, or trifluoroacetate.

In accordance with another aspect of the present invention, there is provided a process for preparing the compound of formula (I) or its pharmaceutically acceptable salt, which comprises oxidizing a compound of formula (V) with an oxidizing agent, in accordance with the following Reaction Scheme 1 described below:

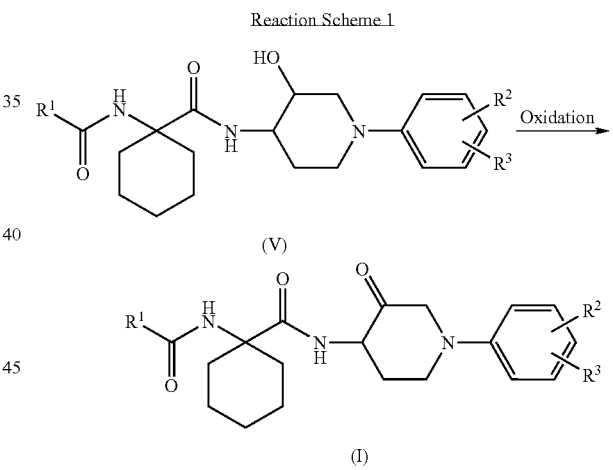

In the above Reaction Scheme 1, $R^1$, $R^2$, and $R^3$ are the same as defined above.

The oxidizing agent includes, but not limited to, a pyridine-SO$_3$ complex, oxalyl chloride-dimethylsulfoxide (Swern oxidation), and pyridinium chlorochromate (Jones oxidation).

The reaction may be performed in the presence or absence of a base. The base used includes, but not limited to, triethylamine, N,N-diisopropylethylamine and N-methylmorpholine. And, the reaction may be performed preferably in the presence of an organic solvent, including dichloromethane, tetrahydrofuran, dimethylformamide, or dimethylsulfoxide. Further, the reaction may be carried out at −78° C.~50° C.

In accordance with still another aspect of the present invention, there is provided an intermediate for the synthesis of the compound of formula (I) or a pharmaceutically acceptable salt thereof. That is, there is provided a compound of formula (V) or a pharmaceutically acceptable salt thereof:

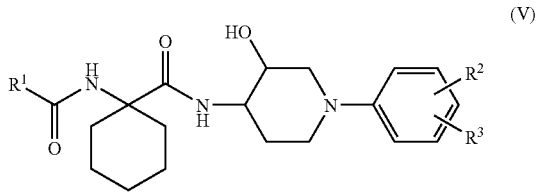

wherein, $R^1$, $R^2$, and $R^3$ are the same as defined above.

In accordance with still another aspect of the present invention, there is provided a process for preparing the synthetic intermediate, i.e., a compound of formula (V) or its pharmaceutically acceptable salt, which comprises reacting a compound of formula (VI) with a compound of formula (VII), in accordance with the following Reaction Scheme 2 described below:

Reaction Scheme 2

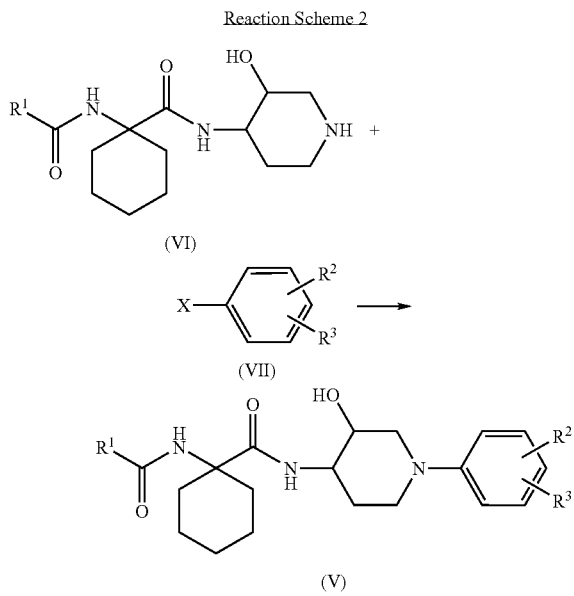

In the above Reaction Scheme 2, $R^1$, $R^2$, and $R^3$ are the same as defined above and X is halogen, nitro, $C_{1-7}$ alkylsulfonyl, or trifluorosulfonate.

In the above Reaction Shceme 2, the compound of formula (VI) may be prepared using a known method [see, e.g., J. Med. Chem. 1994, 30, 999-1014].

The reaction may be performed preferably in the presence of a base, including organic bases, such as triethylamine, N,N-diisopropylethylamine, and N-methylmorpholine; and inorganic bases, such as sodium bicarbonate, calcium carbonate, and potassium carbonate. And, the reaction may be performed preferably in the presence of an organic solvent, including tetrahydrofuran, methanol, ethanol, butanol, acetonitrile, dimethylacetamide, dimethylformamide, or dimethylsulfoxide. Further, the reaction may be carried out at 0° C.~150° C., preferably at 50° C.~120° C.

Moreover, the reaction according to Reaction Scheme 2 may be performed preferably in the presence of a palladium catalyst, such as palladium diacetate (Pd(OAc)$_2$), and tris(dibenzylideneacetone)dipalladium (Pd$_2$(dba)$_2$), to facilitate the reaction by reducing reaction time and increase the yield of product. In case of carrying out the reaction in the presence of the palladium catalyst, the process may be performed preferably in the presence of a ligand and/or a base additionally. Example of the ligand includes (S)-2,2-bis(diphenylphosphino)-1,1-binaphtyl (BINAP), 1,1'-bis(diphenylphosphino)ferrocene (dppf), and (tri-O-tolyl)phosphine (P(O-Tol)$_3$) and example of the base includes cesium carbonate (CsCO$_3$), sodium t-butoxide (t-BuONa), and potassium t-butoxide (t-BuOK). Further, in case of carrying out the reaction in the presence of the palladium catalyst, the process may be carried out in the presence of a solvent, such as benzene, toluene, dioxane, or tetrahydrofuran and at 50° C.~150° C., more preferably at 80° C.~110° C.

In accordance with still another aspect of the present invention, there is provided a pharmaceutical composition for inhibiting cysteine proteases comprising a therapeutically effective amount of a 1-phenylpiperidin-3-one derivative or a pharmaceutically acceptable salt thereof as an active ingredient and a pharmaceutically acceptable carrier.

The pharmaceutically acceptable carrier may be a conventional liquid or solid carrier and the compositions of the present invention may further include an excipient (e.g. lactose, sucrose, corn starch, etc.), lubricating agent (e.g. magnesium stearate, etc.), emulsifier, suspending agent, buffering agent and isotonic agent, sweetener and/or flavoring agent, if necessary.

The compositions of the present invention may be administered, either orally or parenterally. The dosage form for the pharmaceutical composition includes oral dosage forms such as tablets, capsules, aqueous solvents, emulsions, suspensions, etc., and paenteral dosage forms such as injections (e.g. subcutaneous, intravenous, intramuscular and intraperitoneal injections) and external application forms (e.g. transdermal preparation, ointments, etc.).

The pharmaceutical compositions of the present invention can be administered to mammals, including human, to treat osteoporosis, osteoarthritis, hypercalcemia disease, Pagets disease, rheumatoid arthritis or bone related disease by inhibiting the activity of cysteine protease superfamily. Further, the compositions may be administered to patients suffered from stroke, Alzheimers disease, chronic obstructive pulmonary disease (COPD), influenza, hypertenstion, tumor or cancer metastasis.

The pharmaceutical compositions of the present invention may be administered in a daily dose of about 0.1 μg to 1000 mg/kg body weight, in a single dose or in divided doses. However, it should be understood that the amount of the active ingredient actually administered ought to be determined considering various relevant factors including the condition to be treated, the chosen route of administration, the age and weight of the individual patient, and the severity of the patient's symptom; and, therefore, the above dose should not be intended to limit the scope of the invention in any way.

The following Examples are given for the purpose of illustration only, and are not intended to limit the scope of the invention.

PREPARATION EXAMPLE 1

Preparation of tert-butyl 4-amino-hydroxypiperidine-1-carboxylate

Step 1.
N-tert-butoxycarbonyl-1,2,3,6-tetrahydropyridine

The solution of 1,2,3,6-tetrahydropyridine (50 g, 0.60 mol) in 500 ml of dichloromethane was cooled to 0° C. and was added di-tert-butoxydicarbonate (144 g, 0.66 mol)

thereto. The reaction mixture was stirred for about 2 hours at room temperature and concentrated to give the titled compound as an oily form (110 g).

Rf=0.71 [n-Hexane/EtOAc (v/v)=3/1]

Step 2: tert-butyl 7-oxo-3-azabicyclo[4.1.0]heptane-3-carboxylate

To the solution of N-tert-butoxycarbonyl-1,2,3,6-tetrahydropyridine (110 g, 0.60 mol) obtained in Step 1 in 300 ml of dichloromethane, was added 3-chloroperbenzoic acid (m-CPBA; 311 g, 1.80 mol). The reaction mixture was stirred overnight at room temperature and filtered to remove benzoic acid produced. The resulting filtrate was washed with a saturated potassium carbonate solution, brine and distilled water. The resulting organic layer was dried and concentrated on magnesium sulfate to give the titled compound (180.6 g).

Rf=0.62 (n-Hexane/EtOAc (v/v)=3/1) $^1$H NMR (400 MHz, CDCl$_3$): δ 8.15-7.93 (m, 1H), 7.77-7.51 (d, 1H), 7.49-7.36 (q, 1H), 3.87-3.63 (m, 2H), 3.39-3.13 (m, 2H), 2.12-1.88 (m, 2H), 1.50 (s, 9H)

Step 3. tert-Butyl 4-azido-3-hydroxypiperidine-1-carboxylate

To the solution of tert-butyl 7-oxo-3-azabicyclo[4.1.0]heptane-3-carboxylate (180.6 g, 0.60 mol) obtained in Step 2 in a mixed solvent of 700 ml of methanol and 100 ml of water, were added ammonium chloride (NH$_4$Cl; 64.0 g, 1.2 mol) and sodium azide (NaN$_3$; 98.0 g, 1.5 mol). The reaction mixture was refluxed for 8 hours and evaporated under reduced pressure to remove methanol. The resulting residue was extracted with ethyl acetate and then dried on magnesium sulfate. The resulting residue was purified with column chromatography to give the titled compound (62.0 g).

Rf=0.43 (n-Hexane/EtOAc (v/v)=3/1)

Step 4. tert-Butyl 4-amino-3-hydroxypiperidine-1-carboxylate tert-Butyl 4-azido-3-hydroxypiperidine-1-carboxylate (62 g) obtained in Step 3 was dissolved in 300 ml of methanol. The mixture was hydrogenated with 10%-palladuim at room temperature under 35 psi for about 48 hours and filtered. The resulting filtrate was concentrated to give the titled compound (55 g) as a colorless and oily form.

PREPARATION EXAMPLE 2

Preparation of 1-[N-(benzofuran-2-ylcarbonyl)amino]cyclohexane carboxylic acid

Step 1. Methyl 1-[N-(benzofuran-2-ylcarbonyl)amino]-1-cyclohexanecarboxylate The solution of methyl 1-amino-1-cyclohexanecarboxylate (66.1 g, 340 mmol) and benzofuran-2-carboxyl acid (60.0 g) in 500 ml of dichloromethane was cooled to 0° C. and were added dimethylaminopyridine (DMAP, 50.0 g) and 1-(3-dimethylaminopropyl)-3-ethylcarbodiimide hydrochloride (EDC-HCl; 85.0 g) thereto. The reaction mixture was stirred for about 24 hours at room temperature and then ice water (50 g) was added thereto to stop the reaction. The organic layer was separated and concentrated to obtain a residue, which was then dissolved with 400 ml of ethyl acetate. The resulting solution was washed with 10% citric acid solution and saturated sodium bicarbonate solution, and then dried and concentrated on sodium sulfate to give the titled compound (105.0 g). The titled compound was used in the next-step without further purifications.

Step 2. 1-[N-(benzofuran-2-ylcarbonyl)amino]cyclohexanecarboxylic acid

To the solution of methyl 1-[N-(benzofuran-2-ylcarbonyl)amino]-1-cyclohexanecarboxylate (105.0 g) in 450 ml of methanol, was added 2N-sodium hydroxide solution (170 ml, 0.34 mol). The reaction mixture was refluxed for 23 hours and concentrated to obtain a residue, which was diluted with 400 ml of water and washed with 300 ml of diethyl ether. 6N-hydrochloride was added dropwise to the resulting aqueous layer to adjust the pH of the solution to pH 3. The resulting white solid was filtered and dried to give the titled compound (49.5 g).

EXAMPLE 1

Preparation of 4-[N-[1-[N-(benzofuran-2-ylcarbonyl)amino]cyclohexanecarbonyl]amino]-1-(2-methylsulfonylphenyl)piperidin-3-one Step 1.

4-[N-[1-[N-(benzofuran-2-ylcarbonyl)amino]cyclohexanecarbonyl]amino]-1-tert-butoxycarbonyl-3-piperidinol To the solution of tert-butyl 4-amino-3-hydroxypiperidine-1-carboxylate (20 g, 92 mmol) obtained in step 4 of Preparation Example 1 and 1-[N-(benzofuran-2-ylcarbonyl)amino]cyclohexanecarboxylic acid (26 g, 92 mmol) obtained in step 2 of Preparation Example 2 in 150 ml of dimethylformamide, were added hydroxybenzotriazole (HOBt; 24 g, 180 mmol) and diisopropylethylamine (DIEA; 23 g, 180 mmol). The reaction mixture was cooled to 0° C. and was added 1-(3-dimethylaminopropyl)-3-ethylcarbodiimide hydrochloride (EDC-HCl; 35 g, 180 mmol) thereto. The reaction mixture was stirred for 4 hours at room temperature, diluted with 300 ml of ethyl acetate, and washed with 10% citric acid solution, a saturated sodium bicarbonate solution and brine. The resulting organic layer was dried and concentrated on sodium sulfate. The resulting residue was purified with column chromatography to give 30 g of the titled compound.

Step 2.

4-[N-[1-[N-(benzofuran-2-ylcarbonyl)amino]cyclohexanecarbonyl]amino]-3-piperidinol hydrochloride The solution of 4-1-[N-(benzofuran-2-ylcarbonyl)amino]cyclohexanecarbonylamino-1-tert-butoxycarbonyl-3-piperidinol (30 g) obtained in Step 1 in 100 ml of 3N-hydrochloride/ethyl acetate solution was stirred for about 2 hours at room temperature and was added 100 ml of diethyl ether thereto. The resulting white solid was filtered and dried to give 25 g of the titled compound.

Step 3.

4-[N-[1-[N-(benzofuran-2-ylcarbonyl)amino]cyclohexanecarbonyl]amino]-1-(2-methylsulfonylphenyl)piperidin-3-ol To the solution of 4-[N-[1-[N-(benzofuran-2-ylcarbonyl)amino]cyclohexanecarbonyl]amino]-3-piperidinol hydrochloride (10 g, 23.7 mmol) obtained in Step 2 and 1-flourophenyl methyl sulfone (4.9 g, 28.4 mmol) in 50 ml of dimethylformamide, was added potassium carbonate (8.2 g, 59.3 mmol). The reaction mixture was stirred overnight at about 100° C., cooled to room temperature, diluted with 200 ml of ethyl acetate, and washed with brine. The resulting organic layer was dried and concentrated on sodium sulfate. The resulting residue was purified with column chromatography to give 4.9 g of the titled compound as white solid.

$^1$H-NMR (400 MHz, CDCl$_3$) δ 8.03 (m, 1H), 7.69 (d, 1H), 7.62(t, 1H), 7.51 (m, 2H), 7.42 (t, 1H), 7.31 (d, 1H), 7.25 (m, 2H), 7.05 (bs, 1H), 6.81 (s, 1H), 4.24 (bs, 1H), 3.90 (m, 1H), 3.70 (m, 1H), 3.36 (m, 2H), 3.30 (m, 1H), 3.24 (s, 3H), 2.90 (m, 1H), 2.67 (t, 1H), 2.27 (t, 2H), 2.05 (m, 3H), 1.75 (m, 3H), 1.52 (m, 3H), 1.41 (m, 1H)

Step 4.

4-[N-[1-[N-(benzofuran-2-ylcarbonyl)amino]cyclohexanecarbonyl]amino]-1-(2-methylsulonylphenyl)piperidin-3-one To the solution of 4-[N-[1-[N-(benzofuran-2-ylcarbonyl)amino]cyclohexanecarbonyl]amino]-1-(2-methylsulfonylphenyl)piperidin-3-ol (0.49 g, 0.91 mmol) obtained in Step 3 in 3 ml of dimethyl sulfoxide (DMSO), was added dropwise 0.5 ml of triethylamine. The reaction mixture was cooled to 0° C. Pyridine-SO$_3$ complex (0.5 g, 0.31 mmol) was added to the reaction mixture, which was then stirred for 2 hours, diluted with 20 ml of ethyl acetate, and washed with brine. The resulting organic layer was dried and concentrated on sodium sulfate. The resulting residue was purified with column chromatography to give 210 mg of the titled compound as white solid.

mp=219-220° C. $^1$H-NMR (400 MHz, CDCl$_3$) δ 8.07 (t, 1H), 7.68 (m, 2H), 7.55-7.26 (m, 7H), 6.73 (s, 1H), 4.72 (t, 1H), 3.77 (d, 1H), 3.65 (d, 1H), 3.61 (d, 1H), 3.17 (s, 3H), 2.68 (m, 1H), 2.33 (t, 2H), 2.05 (m, 2H), 1.78 (m, 4H), 1.42-1.22 (m, 2H) Mass (M+H)=538

EXAMPLE 2

Preparation of 4-[N-[1-[N-(benzofuran-2-ylcarbonyl)amino]cyclohexanecarbonyl]amino]-1-(2-nitrophenyl)piperidin-3-one In accordance with the same procedure as in Example 1, except that 2-fluoronitrobenzene was used instead of 1-fluorophenyl methyl sulfone in Step 3 thereof, 170 mg of the titled compound was prepared.

$^1$H-NMR (400 MHz, CDCl$_3$) δ 7.69 (d, 1H), 7.57 (m, 2H), 7.49 (m, 2H), 7.31 (m, 1H), 7.06 (t, 1H), 6.97 (d, 1H), 6.73 (s, 1H), 4.71 (m, 1H), 3.86 (q, 3H), 3.41 (t, 1H), 2.78 (m, 1H), 2.31 (broad, 2H), 2.00 (m, 3H), 1.75 (m, 2H), 1.52 (m, 2H), 1.38 (m, 1H)

EXAMPLE 3

Preparation of 4-[N-[1-[N-(benzofuran-2-ylcarbonyl)amino]cyclohexanecarbonyl]amino]-1-(4-fluoro-2-nitrophenyl)piperidin-3-one In accordance with the same procedure as in Example 1, except that 1,4-difluoro-2-nitrobenzene was used instead of 1-fluorophenyl methyl sulfone in Step 3 thereof, 250 mg of the titled compound was prepared.

$^1$H-NMR (400 MHz, CDCl$_3$) δ 7.68 (d, 1H), 7.66 (d, 1H), 7.50 (m, 4H), 7.45 (m, 3H), 6.72 (s, 1H), 4.67 (m, 1H), 3.68 (s, 2H), 3.33 (m, 2H), 2.72 (m, 1H), 2.32 (m, 2H), 2.04 (m, 3H), 1.74 (m, 4H), 1.27 (m, 2H), 1.21 (m, 1H)

EXAMPLE 4

Preparation of 4-[N-[1-[N-(benzofuran-2-ylcarbonyl)amino]cyclohexanecarbonyl]amino]-1-(5-chloro-2-nitrophenyl)piperidin-3-one In accordance with the same procedure as in Example 1, except that 2,4-dichloronirobenzene was used instead of 1-fluorophenyl methyl sulfone in Step 3 thereof, 210 mg of the titled compound was prepared.

$^1$H-NMR (400 MHz, CDCl$_3$) δ 7.75 (d, 1H), 7.72 (d, 1H), 7.67 (m, 2H), 7.07 (m, 1H), 6.96 (s, 1H), 6.93 (d, 2H), 6.87 (s, 1H), 4.72 (m, 1H), 3.72 (s, 2H), 3.46 (m, 2H), 2.53 (m, 1H), 2.25 (m, 2H), 2.02 (m, 3H), 1.76 (m, 4H), 1.43 (m, 2H), 1.13 (m, 1H)

EXAMPLE 5

Preparation of 4-[N-[1-[N-(benzofuran-2-ylcarbonyl)amino]cyclohexanecarbonyl]amino]-1-(4-methanesulfonylphenyl)piperidin-3-one In accordance with the same procedure as in Example 1, except that 4-fluorophenyl methyl sulfone was used instead of 1-fluorophenyl methyl sulfone in Step 3 thereof, 190 mg of the titled compound was prepared.

$^1$H-NMR (400 MHz, CDCl$_3$) δ 7.67 (m, 3H), 7.52 (m, 3H), 7.44 (m, 1H), 6.93 (m, 2H), 6.72 (s, 1H), 4.75 (m, 1H), 3.69 (d, 1H), 3.52 (d, 2H), 3.04 (m, 2H), 2.84 (s, 3H), 2.70 (m, 1H), 2.25 (m, 2H), 2.04 (m, 2H), 1.76 (m, 4H), 1.33 (m, 3H), 1.21(m, 1H)

EXAMPLE 6

Preparation of 4-[N-[1-[N-(benzofuran-2-ylcarbonyl)amino]cyclohexanecarbonyl]amino]-1-(2-acetylphenyl)piperidin-3-one In accordance with the same procedure as in Example 1, except that 2-fluoroacetophenone was used instead of 1-fluorophenyl methyl sulfone in Step 3 thereof, 110 mg of the titled compound was prepared.

$^1$H-NMR (400 MHz, CDCl$_3$) δ 7.68 (d, 1H), 7.66 (m, 2H), 7.53 (m, 3H), 7.08 (m, 2H), 6.72 (s, 1H), 4.83 (m, 1H), 3.69 (q, 2H), 3.31 (m, 2H), 2.68 (m, 1H), 2.53 (s, 3H), 2.29 (m, 2H), 2.04 (m, 2H), 1.71 (m, 4H), 1.27 (m, 3H), 1.25 (m, 1H)

EXAMPLE 7

Preparation of 4-[N-[1-[N-(benzofuran-2-ylcarbonyl)amino]cyclohexanecarbonyl]amino]-1-(4-cyanophenyl)piperidin-3-one In accordance with the same procedure as in Example 1, except that 4-fluorobenzonitrile was used instead of 1-fluorophenyl methyl sulfone in Step 3 thereof, 120 mg of the titled compound was prepared.

$^1$H-NMR (400 MHz, CDCl$_3$) δ 7.69 (d, 1H), 7.53 (m, 6H), 7.52 (m, 1H), 6.82 (s, 1H), 4.82 (m, 1H), 4.17 (d, 1H), 3.93 (d, 1H), 3.55 (m, 1H), 3.51 (m, 1H), 2.14 (m, 3H), 1.98 (m, 4H), 1.75 (m, 5H), 1.63 (m, 2H), 1.24 (m, 1H)

EXAMPLE 8

Preparation of 4-[N-[1-[N-(benzofuran-2-ylcarbonyl)amino]cyclohexanecarbonyl]amino]-1-(2-cyano-3-fluorophenyl)piperidin-3-one In accordance with the same procedure as in Example 1, except that 2,6-difluorobenzonitrile was used instead of 1-fluorophenyl methyl sulfone in Step 3 thereof, 170 mg of the titled compound was prepared.

$^1$H-NMR (400 MHz, CDCl$_3$) δ 7.69 (d, 1H), 7.53 (m, 6H), 6.82 (s, 1H), 4.69 (m, 1H), 4.13 (d, 1H), 3.90 (d, 1H), 3.81 (m, 1H), 3.57 (m, 1H), 2.83 (m, 1H), 2.02 (m, 2H) 1.98 (m, 4H), 1.77 (m, 4H), 1.68 (m, 2H), 1.26 (m, 1H)

EXAMPLE 9

Preparation of 4-[N-[1-[N-(benzofuran-2-ylcarbonyl)amino]cyclohexanecarbonyl]amino]-1-(2-cyano-6-fluorophenyl)piperidin-3-one In accordance with the same procedure as in Example 1, except that 2,3-difluorobenzonitrile was used instead of 1-fluorophenyl methyl sulfone in Step 3 thereof, 220 mg of the titled compound was prepared.

$^1$H-NMR (400 MHz, CDCl$_3$) δ 7.69 (d, 1H), 7.67 (m, 2H), 7.45 (m, 3H), 7.33(m, 1H), 6.74 (s, 1H), 4.87 (m, 1H), 4.03 (d, 1H), 3.82 (d, 1H), 3.73 (m, 1H), 3.52 (m, 1H), 2.87(m, 1H), 2.34 (m, 2H) 1.99 (m, 4H), 1.77 (m, 4H), 1.68 (m, 2H), 1.26 (m, 1H)

EXAMPLE 10

Preparation of 4-[N-[1-[N-(benzofuran-2-ylcarbonyl)amino]cyclohexanecarbonyl]amino]-1-(2-cyano-5-fluorophenyl)piperidin-3-one In accordance with the same procedure as in Example 1, except that 2,4-difluorobenzonitrile was used instead of 1-fluorophenyl methyl sulfone in Step 3 thereof, 210 mg of the titled compound was prepared.

$^1$H-NMR (400 MHz, CDCl$_3$) δ 7.69 (d, 1H), 7.67 (m, 2H), 7.47 (m, 3H), 7.43 (m, 1H), 6.72 (s, 1H), 4.67 (m, 1H), 4.16 (d, 1H), 3.97 (d, 1H), 3.68 (m, 1H), 3.59 (m, 1H), 2.75 (m, 1H), 2.30 (m, 2H) 1.99 (m, 4H), 1.77 (m, 4H), 1.68 (m, 2H), 1.26 (m, 1H)

EXAMPLE 11

Preparation of 4-[N-[1-[N-(benzofuran-2-ylcarbonyl)amino]cyclohexanecarbonyl]amino]-1-(3-cyano-5-fluorophenyl)piperidin-3-one In accordance with the same procedure as in Example 1, except that 3,5-difluorobenzonitrile was used instead of 1-fluorophenyl methyl sulfone in Step 3 thereof, 200 mg of the titled compound was prepared.

$^1$H-NMR (400 MHz, CDCl$_3$) δ 7.69 (d, 1H), 7.55 (m, 5H), 7.26 (m, 1H), 6.72 (m, 1H), 4.66 (m, 1H), 4.11 (d, 1H), 3.85 (d, 1H), 3.51 (m, 2H), 2.92 (m, 1H), 2.32 (m, 3H), 1.98 (m, 3H), 1.75 (m, 6H), 1.68 (m, 4H), 1.53(m, 1H)

EXAMPLE 12

Preparation of 4-[N-[1-[N-(benzofuran-2-ylcarbonyl)amino]cyclohexanecarbonyl]amino]-1-(2-ethylsulfonylphenyl)piperidin-3-one In accordance with the same procedure as in Example 1, except that 1-fluorophenyl ethyl sulfone was used instead of 1-fluorophenyl methyl sulfone in Step 3 thereof, 180 mg of the titled compound was prepared.

$^1$H-NMR (400 MHz, CDCl$_3$) δ 8.05 (d, 1H), 7.70 (m, 2H), 7.50 (m, 3H), 7.43 (m, 3H), 6.73 (s, 1H), 4.71 (m, 1H), 3.75 (d, 1H), 3.55 (d, 1H), 3.53 (d, 1H), 3.35 (m, 2H), 3.17 (t, 1H), 2.71 (m, 1H), 2.30 (m, 2H), 2.05 (m, 2H), 1.91 (m, 1H), 1.74 (m, 3H), 1.55 (m, 2H), 1.35 (m, 1H) 1.12 (t, 3H)

EXAMPLE 13

Preparation of 4-[N-[1-[N-(benzofuran-2-ylcarbonyl)amino]cyclohexanecarbonyl]amino]-1-(4-acetylphenyl)piperidin-3-one In accordance with the same procedure as in Example 1, except that 4-fluoroacetophenone was used instead of 1-fluorophenyl methyl sulfone in Step 3 thereof, 120 mg of the titled compound was prepared.

$^1$H-NMR (400 MHz, CDCl$_3$): 8.00 (d, 1H), 7.98 (d, 1H), 7.89 (m, 1H), 7.51 (m, 4H), 7.48 (m, 2H), 6.82(s, 1H), 4.87 (m, 1H), 4.21 (d, 1H), 3.95 (d, 1H), 3.64(t, 1H), 3.16 (m, 1H), 2.46 (s, 3H), 2.15 (m, 3H), 1.98 (m, 5H), 1.76 (m, 6H), 1.74 (m, 3H)

EXAMPLE 14

Preparation of 4-[N-[1-[N-(benzofuran-2-ylcarbonyl)amino]cyclohexanecarbonyl]amino]-1-(4-formylphenyl)piperidin-3-one In accordance with the same procedure as in Example 1, except that 4-fluorobenzadehyde was used instead of 1-fluorophenyl methyl sulfone in Step 3 thereof, 150 mg of the titled compound was prepared.

$^1$H-NMR (400 MHz, CDCl$_3$) δ 9.78 (s, 1H), 7.67(d, 2H), 7.74 (d, 1H), 7.68 (m, 2H), 7.47 (m, 2H), 7.31 (m, 1H), 6.86 (m, 1H), 6.74 (s, 1H), 4.70 (m, 1H), 4.22 (d, 1H), 3.99 (d, 1H), 3.95 (m, 1H), 3.60 (m, 2H), 2.87 (m, 1H), 2.28 (m, 2H), 1.98 (m, 2H), 1.75 (m, 3H), 1.52 (m, 2H)

EXAMPLE 15

Preparation of 4-[N-[1-[N-(benzofuran-2-ylcarbonyl)amino]cyclohexanecarbonyl]amino]-1-(2-formylphenyl)piperidin-3-one In accordance with the same procedure as in Example 1, except that 2-fluorobenzaldehyde was used instead of 1-fluorophenyl methyl sulfone in Step 3 thereof, 130 mg of the titled compound was prepared.

$^1$H-NMR (400 MHz, CDCl$_3$) δ 10.21 (s, 1H), 7.95 (d, 1H), 7.87 (d, 1H), 7.67 (m, 2H), 7.55 (m, 2H), 7.47 (m, 1H), 7.31 (m, 1H), 6.73 (s, 1H), 4.68 (m, 1H), 3.76 (s, 2H), 3.43 (q, 2H), 2.78 (m, 1H), 2.33 (m, 2H), 2.02 (m, 5H), 1.99 (m, 4H), 1.60 (m, 1H), 1.26 (m, 1H)

EXAMPLE 16

Preparation of 4-[N-[1-[N-(benzofuran-2-ylcarbonyl)amino]cyclohexanecarbonyl]amino]-1-(4-nitrophenyl)piperidin-3-one In accordance with the same procedure as Example 1, except that 4-fluoronitrobenzene was used instead of 1-fluorophenyl methyl sulfone in Step 3 thereof, 190 mg of the titled compound was prepared.

$^1$H-NMR (400 MHz, CDCl$_3$) δ 8.13(m, 1H), 7.68(m, 1H), 7.54(m, 2H), 7.47(m, 2H), 7.45 (m, 2H), 6.75(s, 1H), 4.78 (m, 1H), 4.24 (d, 1H), 4.03(d, 1H), 3.89(t, 1H) 2.94 (m, 1H), 2.27 (m, 3H), 1.98 (m, 5H), 1.76(m, 5H), 1.72(m, 3H), 1.52 (m, 1H)

EXAMPLE 17

Preparation of 4-[N-[1-[N-(benzofuran-2-ylcarbonyl)amino]cyclohexanecarbonyl]amino]-1-(3-methyl-4-nitrophenyl)piperidin-3-one In accordance with the same procedure as in Example 1, except that 4-fluoro-2-methyl-nitrobenzene was used instead of 1-fluorophenyl methyl sulfone in Step 3 thereof, 170 mg of the titled compound was prepared.

$^1$H-NMR (400 MHz, CDCl$_3$) δ 7.69 (d, 1H), 7.55 (d, 1H), 7.53 (m, 3H), 7.33 (m, 1H), 7.14 (m, 1H), 6.73 (m, 3H), 4.72 (m, 1H), 3.59 (d, 1H), 3.18 (s, 3H), 3.15 (m, 2H), 2.75 (m, 1H), 2.64 (s, 3H), 2.34 (m, 2H), 2.16 (m, 2H), 1.98(m, 1H), 1.79 (m, 3H), 1.72 (m, 2H), 1.52 (m, 1H)

EXAMPLE 18

Preparation of 4-[N-[1-[N-(benzofuran-2-ylcarbonyl)amino]cyclohexanecarbonyl]amino]-1-(3-fluoro-2-formylphenyl)piperidin-3-one In accordance with the same procedure as in Example 1, except that 2,6-difluorobenzaldehyde was used instead of 1-fluorophenyl methyl sulfone in Step 3 thereof, 210 mg of the titled compound was prepared.

$^1$H-NMR (400 MHz, CDCl$_3$) δ 10.33 (s, 1H), 7.94 (d, 1H), 7.61(m, 1H), 7.35 (m, 1H), 7.23 (m, 2H), 7.04 (m, 1H), 6.99 (m, 1H), 4.78 (m, 1H), 4.12 (m, 1H), 3.76 (m, 1H), 3.25 (m, 1H), 3.07 (m, 1H), 2.94 (m, 1H), 2.36 (m, 1H), 2.22 (m, 1H), 2.01 (m, 4H), 1.63 (m, 3H), 1.45 (m, 1H), 1.24 (m, 1H)

EXAMPLE 19

Preparation of 4-[N-[1-[N-(benzofuran-2-ylcarbonyl)amino]cyclohexanecarbonyl]amino]-1-(3-chloro-2-formylphenyl)piperidin-3-one In accordance with the same procedure as in Example 1, except that 2-chloro-6-fluorobenzaldehyde was used instead of 1-fluorophenyl methyl sulfone in Step 3 thereof, 200 mg of the titled compound was prepared.

$^1$H-NMR (400 MHz, CDCl$_3$) δ 10.31 (s, 1H), 7.66 (d, 1H), 7.53 (m, 1H), 7.34 (m, 1H), 7.26 (m, 2H), 6.95 (m, 1H), 6.93 (m, 1H), 4.69 (m, 1H), 4.11 (m, 1H), 3.39 (m, 2H), 3.25 (m, 1H), 2.23 (m, 1H), 2.32 (m, 1H), 2.05 (m, 1H), 2.01 (m, 4H), 1.72 (m, 3H), 1.53 (m, 1H), 1.26 (m, 1H)

EXAMPLE 20

Preparation of 4-[N-[1-[N-(benzofuran-2-ylcarbonyl)amino]cyclohexanecarbonyl]amino]-1-(2-formyl-4-nitrophenyl)piperidin-3-one In accordance with the same procedure as in Example 1, except that 2-fluoro-5-nitrobenzaldehyde was used instead of 1-fluorophenyl methyl sulfone in Step 3 thereof, 180 mg of the titled compound was prepared.

$^1$H-NMR (400 MHz, CDCl$_3$) δ 8.63 (s, 1H), 8.23 (d, 1H), 7.69 (m, 2H), 7.53 (m, 2H), 7.47 (m, 3H), 6.84 (s, 1H), 4.84 (m, 1H), 4.51 (m, 1H), 4.32 (m, 1H), 2.35 (m, 1H), 3.32 (m, 3H), 2.06 (m, 3H), 1.78 (m, 4H), 1.55 (m, 1H), 1.25 (m, 1H)

EXAMPLE 21

Preparation of 4-[N-[1-[N-(benzofuran-2-ylcarbonyl)amino]cyclohexanecarbonyl]amino]-1-(2-formyl-6-fluorophenyl)piperidin-3-one In accordance with the same procedure as in Example 1, except that 2,3-difluorobenzaldehyde was used instead of 1-fluorophenyl methyl sulfone in Step 3 thereof, 110 mg of the titled compound was prepared.

$^1$H-NMR (400 MHz, CDCl$_3$) δ 10.42 (s, 1H), 7.86 (d, 1H), 7.65 (m, 2H), 7.61 (m, 1H), 7.30 (m, 2H), 7.02 (m, 1H), 6.42 (s, 1H), 4.37 (m, 1H), 3.56 (m, 1H), 3.46 (m, 2H), 3.03 (m, 1H), 2.45 (m, 1H), 2.21 (m, 1H), 2.02 (m, 2H), 1.94 (m, 1H), 1.76 (m, 4H), 1.64 (m, 3H), 1.28 (m, 2H)

EXAMPLE 22

Preparation of 4-[N-[1-[N-(benzofuran-2-ylcarbonyl)amino]cyclohexanecarbonyl]amino]-1-(2-fluoro-3-formylphenyl)piperidin-3-one In accordance with the same procedure as in Example 1, except that 2,3-difluorobenzaldehyde was used instead of 1-fluorophenyl methyl sulfone in Step 3 thereof, 100 mg of the titled compound was prepared.

$^1$H-NMR (400 MHz, CDCl$_3$) δ 10.41(s, 1H), 7.80 (d, 1H), 7.59 (m, 1H), 7.34 (m, 1H), 7.26 (m, 2H), 7.17 (m, 1H), 6.81 (m, 1H), 4.15 (m, 1H), 4.13 (m, 1H), 3.95 (m, 1H), 3.36 (m, 2H), 3.15 (m, 1H), 3.00 (m, 1H), 2.29 (m, 3H), 2.01 (m, 5H), 1.79 (m, 4H), 1.54 (m, 3H), 1.28 (m, 2H)

EXAMPLE 23

Preparation of 4-[N-[1-[N-(benzofuran-2-ylcarbonyl)amino]cyclohexanecarbonyl]amino]-1-(2-isopropylsulfonylphenyl)piperidin-3-one In accordance with the same procedure as in Example 1, except that 1-fluorophenyl isopropyl sulfone was used instead of 1-fluorophenyl methyl sulfone in Step 3 thereof, 170 mg of the titled compound was prepared.

$^1$H-NMR (400 MHz, CDCl$_3$) δ 8.05 (d, 1H), 7.69 (d, 1H), 7.63 (t, 1H), 7.54 (d, 1H), 7.43 (m, 3H), 7.29 (m, 3H), 6.73 (s, 1H), 4.70 (m, 1H), 3.77 (m, 1H), 3.76 (d, 1H), 3.57 (d, 1H), 3.54 (m, 1H), 3.15 (t, 1H), 2.73 (m, 1H), 2.31 (t, 2H), 2.05 (t, 2H), 1.90 (m, 1H), 1.74 (m, 3H), 1.56 (m, 2H), 1.40 (m, 1H) 1.33 (d, 3H), 1.06 (d, 3H)

EXAMPLE 24

Preparation of 4-[N-[1-[N-(benzofuran-2-ylcarbonyl)amino]cyclohexanecarbonyl]amino]-1-(4-fluoro-2-trifluoromethylphenyl)piperidin-3-one Step 1.

4-[N-[1-[N-(benzofuran-2-ylcarbonyl)amino]cyclohexanecarbonyl]amino]-1-(4-fluoro-2-trifluoromethylphenyl)piperidin-3-ol To the suspension of 4-[N-[1-[N-(benzofuran-2-ylcarbonyl)amino]cyclohexanecarbonyl]amino]-3-piperidinol hydrochloride (300 mg) obtained in Step 2 of Example 1 in 5 ml of toluene, were added 1-bromo-4-fluoro-2-trifluoromethylbenzene (0.198 ml), cesium carbonate (1.42 g), (S)-2,2-bis(diphenylphospino)-1,1-binaphtyl (BINAP; 45.4 mg) and tris(dibenzylideneacetone)dipalladium (1.42 g). The reaction mixture was stirred for about 4 hours at 100° C. under nitrogen atmosphere, was diluted with 30 ml of ethyl acetate, filtered, and concentrated. The resulting residue was purified with column chromatography to give 179 mg of the titled compound.

$^1$H-NMR (400 MHz, CDCl$_3$) δ 7.80-7.00 (m, 6H), 7.70 (m, 1H), 4.80 (m, 1H), 3.80-3.60 (m, 3H), 3.30 (m, 1H), 3.00 (m, 1H), 2.69 (m, 1H), 2.33 (d, 2H), 2.01 (t, 2H), 1.80-1.68 (m, 2H), 1.43 (t, 2H), 1.35 (d, 2H)

Step 2.

4-[N-[1-[N-(benzofuran-2-ylcarbonyl)amino]cyclohexanecarbonyl]amino]-1-(4-fluoro-2-trifluoromethylphenyl)piperidin-3-one To the solution of 4-[N-[1-[N-(benzofuran-2-ylcarbonyl)amino]cyclohexanecarbonyl]amino]-1-(4-fluoro-2-trifluoromethylphenyl)piperidin-3-ol (0.15 g) obtained in Step 1 in 3 ml of dimethyl sulfoxide (DMSO), was added 0.16 ml of triethylamine. The reaction mixture was cooled to 0° C. Pyridine-SO$_3$ complex (0.15 g) was added slowly to the reaction mixture, which was then stirred for about 4 hours at room temperature, diluted with 20 ml of ethyl acetate, washed with brine, and dried and concentrated. The resulting residue was purified with column chromatography to give 84 mg of the titled compound as white solid.

$^1$H-NMR (400 MHz, CDCl$_3$) δ 7.69 (d, 1H), 7.56-7.27 (m, 8H), 6.75 (s, 1H), 4.68 (m, 1H), 8.95 (d, 1H), 3.71 (m, 2H), 3.39 (t, 1H), 2.78 (m, 1H), 2.31 (d, 2H), 2.03 (m, 2H), 1.87 (m, 1H), 1.75 (m, 3H), 1.53 (m, 2H), 1.39 (m, 1H)

EXAMPLE 25

Preparation of 4-[N-[1-[N-(benzofuran-2-ylcarbonyl)amino]cyclohexanecarbonyl]amino]-1-(2-cyanophenyl)piperidin-3-one In accordance with the same procedure as in Example 24, except that 2-bromobenzonitrile was used instead of 1-bromo-4-fluoro-2-trifluoromethylbenzene in Step 1 thereof, 160 mg of the titled compound was prepared.

$^1$H-NMR (400 MHz, CDCl$_3$) δ 7.69 (d, 1H), 7.57 (m, 2H), 7.49 (m, 2H), 7.31 (m, 1H), 7.06 (t, 1H), 6.97 (d, 1H), 6.73 (s, 1H), 4.71 (m, 1H), 3.86 (q, 3H), 3.41 (t, 1H), 2.78 (m, 1H), 2.31 (broad, 2H), 2.00 (m, 3H), 1.75 (m, 2H), 1.52 (m, 2H), 1.38 (m, 1H)

EXAMPLE 26

Preparation of 4-[N-[1-[N-(benzofuran-2-ylcarbonyl)amino]cyclohexanecarbonyl]amino]-1-[2-(4-morpholino)phenyl]piperidin-3-one In accordance with the same procedure as in Example 24, except that 2-(4-morpholino)bromobenzene was used instead of 1-bromo-4-fluoro-2-trifluoromethylbenzene in Step 1 thereof, 110 mg of the titled compound was prepared.

$^1$H-NMR (400 MHz, CDCl$_3$) δ 7.75 (d, 1H), 7.55 (d, 1H), 7.43 (m, 3H), 7.34 (t, 1H), 7.12 (m, 2H), 6.93 (m, 2H), 6.74 (s, 1H), 4.65 (m, 1H), 4.21 (d, 1H), 3.84 (m, 4H), 3.50 (d, 1H), 3.13 (m, 1H), 3.08 (m, 4H), 2.81 (m, 1H), 2.32 (d, 2H), 2.12 (t, 2H), 1.75 (m, 4H), 1.52 (m, 2H), 1.32 (m, 1H), 1.25 (m, 1H)

EXAMPLE 27

Preparation of 4-[N-[1-[N-(benzofuran-2-ylcarbonyl)amino]cyclohexanecarbonyl]amino]-1-(2-ethoxyphenyl)piperidin-3-one In accordance with the same procedure as in Example 24, except that 2-bromoethoxybenzene was used instead of 1-bromo-4-fluoro-2-trifluoromethylbenzene in Step 1 thereof, 95 mg of the titled compound was prepared.

$^1$H-NMR (400 MHz, CDCl$_3$) δ 7.75 (d, 1H), 7.65 (d, 1H), 7.52 (m, 3H), 7.39 (t, 1H), 7.04 (m, 1H), 6.85 (m, 2H), 6.74 (s, 1H), 4.64 (m, 1H), 4.05 (q, 2H), 3.97 (d, 1H), 3.65 (m, 1H), 3.58 (d, 1H), 3.21 (m, 1H), 2.72 (m, 1H), 2.29 (m, 2H), 2.07 (t, 2H), 1.81 (m, 1H), 1.65 (m, 3H), 1.52 (t, 2H), 1.35 (t, 3H), 1.32 (m, 1H)

EXAMPLE 28

Preparation of 4-[N-[1-[N-(benzofuran-2-ylcarbonyl)amino]cyclohexanecarbonyl]amino]-1-(2-fluoro-4-trifluoromethylphenyl)piperidin-3-one In accordance with the same procedure as in Example 24, except that 1-bromo-2-fluoro-4-trifluoromethylbenzene was used instead of 1-bromo-4-fluoro-2-trifluoromethylbenzene in Step 1 thereof, 95 mg of the titled compound was prepared.

$^1$H-NMR (400 MHz, CDCl$_3$) δ 7.69 (d, 1H), 7.55 (d, 1H), 7.47 (m, 3H), 7.33 (m, 2H), 7.26 (s, 1H), 6.96 (t, 1H), 6.73 (s, 1H), 4.71 (m, 1H), 8.95 (d, 1H), 3.71 (m, 2H), 3.39 (t, 1H), 2.78 (m, 1H), 2.31 (d, 2H), 2.03 (m, 2H), 1.87 (m, 1H), 1.75 (m, 3H), 1.5 (m, 1H)

EXAMPLE 29

Preparation of 4-[N-[1-[N-(benzofuran-2-ylcarbonyl)amino]cyclohexanecarbonyl]amino]-1-(2-chloro-4-trifluoromethylphenyl)piperidin-3-one In accordance with the same procedure as in Example 24, except that 1-bromo-2-chloro-4-trifluoromethylbenzene was used instead of 1-bromo-4-fluoro-2-trifluoromethylbenzene in Step 1 thereof, 120 mg of the titled compound was prepared.

$^1$H-NMR (400 MHz, CDCl$_3$) δ 7.69 (d, 1H), 7.56-7.27 (m, 8H), 6.75 (s, 1H), 4.68 (m, 1H), 8.95 (d, 1H), 3.71 (m, 2H), 3.39 (t, 1H), 2.78 (m, 1H), 2.31 (d, 2H), 2.03 (m, 2H), 1.87 (m, 1H), 1.75 (m, 3H), 1.53 (m, 2H), 1.39 (m, 1H)

EXAMPLE 30

Preparation of 4-[N-[1-[N-(benzofuran-2-ylcarbonyl)amino]cyclohexanecarbonyl]amino]-1-(2,4-dichlorophenyl)piperidin-3-one In accordance with the same procedure as in Example 24, except that 1-bromo-2,4-dichlorobenzene was used instead of 1-bromo-4-fluoro-2-trifluoromethylbenzene in Step 1 thereof, 100 mg of the titled compound was prepared.

$^1$H-NMR (400 MHz, CDCl$_3$) δ 7.69 (d, 1H), 7.56 (d, 1H), 7.49-7.45 (m, 3H), 7.35-7.31 (m, 2H), 7.19 (d, 1H), 6.93 (d, 1H), 6.74 (s, 1H), 4.69 (m, 1H), 3.74 (d, 1H), 3.71 (d, 1H), 3.69 (d, 1H), 3.19 (t, H), 2.88 (m, 1H), 2.31 (m, 2H), 2.02 (m, 2H), 1.91 (m, 1H), 1.75 (m, 2H), 1.54 (t, 2H), 1.40 (m, 1H)

EXAMPLE 31

Preparation of 4-[N-[1-[N-(benzofuran-2-ylcarbonyl)amino]cyclohexanecarbonyl]amino]-1-(4-chloro-2-fluorophenyl)piperidin-3-one In accordance with the same procedure as in Example 24, except that 1-bromo-4-chloro-2-fluorobenzene was used instead of 1-bromo-4-fluoro-2-trifluoromethylbenzene in Step 1 thereof, 80 mg of the titled compound was prepared.

$^1$H-NMR (400 MHz, CDCl$_3$) δ 7.69 (d, 1H), 7.54 (d, 1H), 7.47-7.45 (m, 3H), 7.31 (t, 1H), 7.05 (m, 2H), 6.84 (t, 1H), 6.72 (s, 1H), 4.68 (m, 1H), 3.83 (d, 1H), 3.79 (d, 1H), 3.52 (d, 1H), 3.29 (t, H), 2.78 (m, 1H), 2.31 (m, 2H), 2.02 (m, 2H), 1.91 (m, 1H), 1.75 (m, 2H), 1.54 (t, 2H), 1.40 (m, 1H)

EXAMPLE 32

Preparation of 4-[N-[1-[N-(benzofuran-2-ylcarbonyl)amino]cyclohexanecarbonyl]amino]-1-(2-methoxy-5-cyanophenyl)piperidin-3-one In accordance with the same procedure as in Example 24, except that 3-bromo-4-methoxybenzonitrile was used instead of 1-bromo-4-fluoro-2-trifluoromethylbenzene in Step 1 thereof, 50 mg of the titled compound was prepared.

$^1$H-NMR (400 MHz, CDCl$_3$) δ 7.69 (d, 1H), 7.54 (d, 1H), 7.47-7.45 (m, 3H), 7.31 (t, 1H), 7.05 (m, 2H), 6.84 (t, 1H), 6.72 (s, 1H), 4.69 (m, 1H), 3.89 (s, 3H), 3.88 (d, 1H), 3.84 (d, 1H), 3.56 (d, 1H), 3.23 (t, H), 2.78 (m, 1H), 2.31 (m, 2H), 2.02 (m, 2H), 1.91 (m, 1H), 1.75 (m, 2H), 1.54 (t, 2H), 1.40 (m, 1H)

EXAMPLE 33

Preparation of 4-[N-[1-[N-(benzofuran-2-ylcarbonyl)amino]cyclohexanecarbonyl]amino]-1-(4-cyano-2-fluorophenyl)piperidin-3-one In accordance with the same procedure as in Example 24, except that 4-bromo-3-fluorobenzonitrile was used instead of 1-bromo-4-fluoro-2-trifluoromethylbenzene in Step 1 thereof, 110 mg of the titled compound was prepared.

$^1$H-NMR (400 MHz, CDCl$_3$) δ 7.69 (d, 1H), 7.56 (d, 1H), 7.49-7.45 (m, 3H), 7.35-7.31 (m, 2H), 7.19 (d, 1H), 6.93 (d, 1H), 6.74 (s, 1H), 4.69 (m, 1H), 3.74 (d, 1H), 3.71 (d, 1H), 3.69 (d, 1H), 3.19 (t, H), 2.88 (m, 1H), 2.31 (m, 2H), 2.02 (m, 2H), 1.91 (m, 1H), 1.75 (m, 2H), 1.54 (t, 2H), 1.40 (m, 1H)

EXAMPLE 34

Preparation of 4-[N-[1-[N-(benzofuran-2-ylcarbonyl)amino]cyclohexanecarbonyl]amino]-1-[2-(2-furyl)phenyl]piperidin-3-one In accordance with the same procedure as in Example 24, except that 1-bromo-2-(2-furyl)benzene was used instead of 1-bromo-4-fluoro-2-trifluoromethylbenzene in Step 1 thereof, 75 mg of the titled compound was prepared.

$^1$H-NMR (400 MHz, CDCl$_3$) δ 7.66 (d, 1H), 7.55-7.44 (m, 5H), 7.42-7.31 (m, 4H), 7.29-7.11 (m, 2H), 7.03 (d, 1H), 6.96 (t, 1H), 6.74 (m, 2H), 4.70 (m, 1H), 3.74 (d, 1H), 3.71 (d, 1H), 3.69 (d, 1H), 3.19 (t, H), 2.88 (m, 1H), 2.31 (m, 2H), 2.02 (m, 2H), 1.40 (m, 1H)

EXAMPLE 35

Preparation of 4-[N-[1-[N-(benzofuran-2-ylcarbonyl)amino]cyclohexanecarbonyl]amino]-1-(2-bromophenyl)piperidin-3-one In accordance with the same procedure as in Example 24, except that 1,2-dibromobenzene was used instead of 1-bromo-4-fluoro-2-trifluoromethylbenzene in Step 1 thereof, 85 mg of the titled compound was prepared.

$^1$H-NMR (400 MHz, CDCl$_3$) δ 7.75 (d, 1H), 7.55 (m, 4H), 7.35 (m, 3H), 7.15 (d, 1H), 6.88 (m, 1H), 6.77 (s, 1H) 4.72 (m, 1H), 3.88 (d, 1H), 3.74 (d, 1H), 3.61 (m, 1H), 2.75 (m, 1H), 3.33 (d, 2H), 2.02 (t, 2H), 1.88 (m, 1H), 1.76 (m, 3H), 1.55 (m, 1H), 1.44 (m, 1H)

EXAMPLE 36

Preparation of 4-[N-[1-[N-(benzofuran-2-ylcarbonyl)amino]cyclohexanecarbonyl]amino]-1-(2-methylthiophenyl)piperidin-3-one In accordance with the same procedure as in Example 24, except that 2-bromothioanisole was used instead of 1-bromo-4-fluoro-2-trifluoromethylbenzene in Step 1 thereof, 65 mg of the titled compound was prepared.

$^1$H-NMR (400 MHz, CDCl$_3$) δ 7.75 (d, 1H), 7.68 (m, 4H), 7.35 (m, 2H), 7.15 (m, 4H), 6.73 (s, 1H), 4.65 (m, 1H), 3.75 (d, 1H), 3.66 (d, 1H), 3.40 (m, 1H), 3.17 (t, 1H) 2.72 (m, 1H), 2.39 (s, 3H), 2.33 (m, 2H), 2.09 (t, 2H), 1.87 (m, 1H), 1.72 (m, 3H), 1.55 (m, 1H) 1.44 (m, 1H)

EXAMPLE 37

Preparation of 4-[N-[1-[N-(benzofuran-2-ylcarbonyl)amino]cyclohexanecarbonyl]amino]-1-[2-(tert-butoxycarbonyl)phenyl]piperidin-3-one In accordance with the same procedure as in Example 24, except that tert-butyl 2-bromobenzoate was used instead of 1-bromo-4-fluoro-2-trifluoromethylbenzene in Step 1 thereof, 65 mg of the titled compound was prepared.

$^1$H-NMR (400 MHz, CDCl$_3$) δ 7.64 (m, 2H), 7.51 (d, 1H), 7.47 (m, 2H), 7.44 (m, 3H), 6.97 (d, 1H), 6.89 (m, 1H), 6.72 (s, 1H), 4.63 (m, 1H), 3.80 (d, 1H), 3.77 (d, 1H), 3.63 (m, 1H), 3.29 (m, 1H), 2.61 (m, 1H), 2.29 (d, 2H), 1.97 (m, 3H), 1.76 (m, 3H), 1.58 (s, 9H), 1.50 (m, 2H), 1.38 (m, 1H)

EXAMPLE 38

Preparation of 4-[N-[1-[N-(benzofuran-2-ylcarbonyl)amino]cyclohexanecarbonyl]amino]-1-(2-ethoxycarbonylphenyl)piperidin-3-one In accordance with the same procedure as in Example 24, except that ethyl 2-bromobenzoate was used instead of 1-bromo-4-fluoro-2-trifluoromethylbenzene in Step 1 thereof, 80 mg of the titled compound was prepared.

$^1$H-NMR (400 MHz, CDCl$_3$) δ 7.64 (m, 2H), 7.51 (d, 1H), 7.47 (m, 2H), 7.44 (m, 3H), 6.97 (d, 1H), 6.89 (m, 1H), 6.72 (s, 1H), 4.63 (m, 1H), 4.30 (q, 2H), 3.80 (d, 1H), 3.77 (d, 1H), 3.63 (m, 1H), 3.29 (m, 1H), 2.61 (m, 1H), 2.29 (d, 2H), 1.97 (m, 3H), 1.76 (m, 3H), 1.50 (m, 2H), 1.38 (m, 1H), 1.20 (t, 3H)

EXAMPLE 39

Preparation of 4-[N-[1-[N-(benzofuran-2-ylcarbonyl)amino]cyclohexanecarbonyl]amino]-1-(2-methoxyphenyl)piperidin-3-one In accordance with the same procedure as in Example 24, except that 2-bromoanisole was used instead of 1-bromo-4-fluoro-2-trifluoromethylbenzene in Step 1 thereof, 60 mg of the titled compound was prepared.

$^1$H-NMR (400 MHz, CDCl$_3$) δ 7.75 (d, 1H), 7.67 (d, 1H), 7.51 (m, 3H), 7.34 (m, 1H), 7.07 (m, 1H), 6.91 (m, 3H), 6.74 (s, 1H), 4.66 (m, 1H), 3.92 (d, 1H), 3.84 (s, 3H), 3.58 (m, 2H), 3.22 (t, 1H), 2.75 (m, 1H) 2.32 (m, 2H), 2.05 (m, 2H), 1.85 (m, 1H), 1.75 (m, 3H), 1.52 (m, 2H), 1.35 (m, 1H)

EXAMPLE 40

Preparation of 4-[N-[1-[N-(benzofuran-2-ylcarbonyl)amino]cyclohexanecarbonyl]amino]-1-(4-fluoro-2-methylphenyl)piperidin-3-one In accordance with the same procedure as in Example 24, except that 2-bromo-5-fluorotoluene was used instead of 1-bromo-4-fluoro-2-trifluoromethylbenzene in Step 1 thereof, 70 mg of the titled compound was prepared.

$^1$H-NMR (400 MHz, CDCl$_3$) δ 7.68 (d, 1H), 7.48 (m, 4H), 7.33 (m, 1H), 6.98 (m, 1H), 6.85 (m, 2H), 6.75 (s, 1H), 4.65 (m, 1H), 3.51 (s, 2H), 3.13 (d, 2H), 2.74 (m, 1H), 2.33 (m, 2H), 2.26 (s, 3H), 2.01 (m, 3H), 1.75 (m, 3H), 1.52 (t, 2H), 1.32 (m, 1H)

EXAMPLE 41

Preparation of 4-[N-[1-[N-(benzofuran-2-ylcarbonyl)amino]cyclohexanecarbonyl]amino]-1-(2-isopropoxyphenyl)piperidin-3-one In accordance with the same procedure as in Example 24, except that 1-bromo-2-isopropoxybenzene was used instead of 1-bromo-4-fluoro-2-trifluoromethylbenzene in Step 1 thereof, 55 mg of the titled compound was prepared.

$^1$H-NMR (400 MHz, CDCl$_3$) δ 7.65 (d, 1H), 7.59-7.37(m, 4H), 7.27 (t, 1H), 6.97 (m, 1H), 6.85 (m, 3H), 6.72 (s, 1H), 4.65 (m, 1H), 4.55 (m, 1H), 3.89 (d, 1H), 3.58 (m, 2H), 3.21 (t, 1H), 2.68 (m, 1H), 2.31 (m, 2H), 2.01 (m, 2H), 1.72 (m, 4H), 1.49 (m, 2H), 1.41 (m, 1H), 1.32 (dd, 6H)

EXAMPLE 42

Preparation of 4-[N-[1-[N-(benzofuran-2-ylcarbonyl)amino]cyclohexanecarbonyl]amino]-1-(2-ethylthiophenyl)piperidin-3-one In accordance with the same procedure as in Example 24, except that 1-bromo-2-ethylthiobenzene was used instead of 1-bromo-4-fluoro-2-trifluoromethylbenzene in Step 1 thereof, 40 mg of the titled compound was prepared.

$^1$H-NMR (400 MHz, CDCl$_3$) δ 7.75 (d, 1H), 7.59-7.41 (m, 4H), 7.33 (m, 1H), 7.25 (m, 3H), 7.05 (d, 1H), 6.73 (s, 1H), 4.65 (m, 1H), 3.69 (d, 1H), 3.55 (d, 1H), 3.45 (d, 1H), 3.15 (t, 1H), 2.89 (q, 2H), 2.71 (m, 1H), 2.31 (d, 2H), 2.05 (t, 2H), 1.89 (m, 1H), 1.75 (m, 3H), 1.54 (m, 2H), 1.36 (m, 1H) 1.34 (t, 3H)

EXAMPLE 43

Preparation of 4-[N-[1-[N-(benzofuran-2-ylcarbonyl)amino]cyclohexanecarbonyl]amino]-1-[2-(3,3-dimethylazetidin-2-one-1-yl)phenyl]piperidin-3-one Step 1.

4-[N-[1-[N-(benzofuran-2-ylcarbonyl)amino]cyclohexanecarbonyl]amino]-1-(2-nitrophenyl)piperidin-3-ol To the solution of 4-[N-[1-[N-(benzofuran-2-ylcarbonyl)amino]cyclohexanecarbonyl]amino]-3-piperidinol hydrochloride (6.0 g) obtained in Step 2 of Example 1 in 50 ml of ethanol, were added 3.7 ml of 2-fluoronitrobenzene and 4.8 ml of triethylamine. The reaction mixture was refluxed overnight and concentrated. The resulting residue was filtered and dried to give 7.2 g of the titled compound.

$^1$H-NMR (400 MHz, CDCl$_3$) δ 7.70 (d, 1H), 7.68-7.46 (m, 4H), 7.33 (t, 1H), 7.21-7.15 (m, 2H), 6.99 (d, 1H), 6.92 (d, 1H), 6.84 (d, 1H), 6.82 (s, 1H), 4.09 (broad, 1H), 3.81 (m, 2H), 3.67 (m, 1H), 3.31 (d, 1H), 3.15 (d, 1H), 2.66 (m, 2H), 2.28 (t, 2H), 2.02 (m, 2H), 1.76-1.55 (m, 4H), 1.48 (t, 2H), 1.28 (m, 1H)

Step 2.

4-[N-[1-[N-(benzofuran-2-ylcarbonyl)amino]cyclohexanecarbonyl]amino]-1-(2-aminophenyl)piperidin-3-ol 4-[N-[1-[N-(benzofuran-2-ylcarbonyl)amino]cyclohexanecarbonyl]amino]-1-(2-nitrophenyl)piperidin-3-ol (7.0 g)

obtained in Step 1 was dissolved in 30 ml of methanol. The solution was stirred with 10%-palladium catalyst overnight under 30 psi hydrogen atmosphere, and then filtered and concentrated to give 6.5 g of titled compound.

$^1$H-NMR (400 MHz, CDCl$_3$) δ 7.70 (d, 1H), 7.68-7.52 (m, 2H), 7.46 (m, 1H), 7.33 (m, 1H), 7.15 (d, 1H), 6.99 (d, 1H), 6.92 (d, 1H), 6.72 (s, 1H), 6.70 (m, 3H), 4.09 (broad, 1H), 3.81 (m, 2H), 3.67 (m, 1H), 3.31 (d, 1H), 3.15 (d, 1H), 2.66 (m, 2H), 2.28 (t, 2H), 2.02 (m, 2H), 1.76-1.55 (m, 4H), 1.48 (t, 2H), 1.28 (m, 1H)

Step 3.

4-[N-[1-[N-(benzofuran-2-ylcarbonyl)amino]cyclohexanecarbonyl]amino]-1-[2-(3-chloro-2,2-dimethylbutyryl)aminophenyl]piperidin-3-ol The solution of 4-[N-[1-[N-(benzofuran-2-ylcarbonyl)amino]cyclohexane carbonyl]amino]-1-(2-aminophenyl)piperidin-3-ol (4.0 g) obtained in Step 2 in 30 ml of dichloromethane was cooled to 0° C. 2.2 ml of triethylamine and 2.1 ml of 3-chloropivaloyl chloride were added dropwise to the reaction mixture, which was then stirred for about 2 hours at room temperature. 20 ml of iced water was added to the reaction mixture. The resulting organic layer was dried and concentrated on sodium sulfate. The resulting residue was crystallized with ethyl acetate to give 4.1 g of the titled compound.

Step 4.

4-[N-[1-[N-(benzofuran-2-ylcarbonyl)amino]cyclohexanecarbonyl]amino]-1-[2-(3,3-dimethylazetidin-2-one-1-yl)phenyl]piperidin-3-ol The solution of 4-[N-[1-[N-(benzofuran-2-ylcarbonyl)amino]cyclohexanecarbonyl]amino]-1-[2-(3-chloro-2,2-dimethylbutyryl)aminophenyl]piperidin-3-ol (4.1 g) obtained in Step 3 in 50 ml of dimethylformamide was cooled to 0° C. Sodium hydride (NaH, 60%; 640 mg) was added to the reaction mixture, which was then stirred overnight at 50° C., diluted with ethyl acetate, washed with a brine, and then dried and concentrated on sodium sulfate. The resulting residue was purified with column chromatography to give 2.1 g of the titled compound.

$^1$H-NMR (400 MHz, CDCl$_3$) δ 7.72 (t, 2H), 7.54 (m, 3H), 7.33 (t, 1H), 7.07 (m, 4H), 6.77 (s, 1H), 4.22 (d, 1H), 3.81 (m, 1H), 3.73 (m, 2H), 3.66 (d, 1H), 3.56 (d, 1H), 3.37 (d, 1H), 3.11 (d, 1H), 2.71 (m, 2H), 2.28 (m, 2H), 2.06 (m, 2H), 1.78 (m, 4H), 1.38 (m, 2H), 1.23 (d, 6H)

Step 5.

4-[N-[1-[N-(benzofuran-2-ylcarbonyl)amino]cyclohexanecarbonyl]amino]-1-[2-(3,3-dimethylazetidin-2-one-1-yl)phenyl]piperidin-3-one To the solution of 4-[N-[1-[N-(benzofuran-2-ylcarbonyl)amino]cyclohexanecarbonyl]amino]-1-[2-(3,3-dimethylazetidin-2-one-1-yl)phenyl]piperidin-3-ol (0.14 g) obtained in Step 4 in 3 ml of dimethylsulfoxide (DMSO), was added 0.16 ml of triethylamine. The reaction mixture was cooled to 0° C. Pyridine-SO$_3$ complex (0.15 g) was added slowly to the reaction mixture, which was stirred for about 10 hours at room temperature. The reaction mixture was diluted with 20 ml of ethyl acetate, washed with brine. The resulting organic layer was dried and concentrated on sodium sulfate. The resulting residue was filtered and dried to give 120 mg of the titled compound as white color.

$^1$H-NMR (400 MHz, CDCl$_3$) δ 7.87 (d, 1H), 7.70 (d, 1H), 7.56 (d, 1H), 7.50-7.46 (m, 3H), 7.33 (d, 1H), 7.11 (t, 3H), 6.74 (s, 1H), 4.67 (t, 1H), 3.62 (t, 2H), 3.46 (t, 2H), 2.69 (m, 1H), 2.33 (d, 2H), 2.01 (t, 2H), 1.80-1.68 (m, 2H), 1.43 (t, 2H), 1.35 (d, 6H)

EXAMPLE 44

Preparation of 4-[N-[1-[N-(benzofuran-2-ylcarbonyl)amino]cyclohexanecarbonyl]amino]-1-[2-(pyrrolidin-2-one-1-yl)phenyl]piperidin-3-one In accordance with the same procedure as in Example 43, except that 4-chlorobutyryl chloride was used instead of 3-chloropivaloyl chloride in Step 3 thereof, 105 mg of the titled compound was prepared.

$^1$H-NMR (400 MHz, CDCl$_3$) δ 7.68 (d, 1H), 7.54 (d, 1H), 7.50-7.36 (m, 3H), 7.32 (t, 1H), 7.25-7.17 (m, 4H), 7.11 (t, 1H), 7.08 (d, 1H), 6.72 (s, 1H), 4.65 (m, 1H), 3.73 (q, 1H), 3.66 (m, 1H), 3.63 (d, 1H), 3.55 (d, 1H), 3.42 (d, 1H), 3.28 (t, 1H), 2.78 (m, 1H), 2.57 (m, 2H), 2.30 (d, 2H), 2.13 (m, 2H), 2.01 (t, 2H), 1.76 (m, 4H), 1.48 (t, 2H), 1.24 (m, 1H) Mass (M+H)=543

EXAMPLE 45

Preparation of 4-[N-[1-[N-(benzofuran-2-ylcarbonyl)amino]cyclohexanecarbonyl]amino]-1-[2-(piperidin-2-one-1-yl)phenyl]piperidin-3-one In accordance with the same procedure as in Example 43, except that 5-chlorovaleryl chloride was used instead of 3-chloropivaloyl chloride in Step 3 thereof, 90 mg of the titled compound was prepared.

$^1$H-NMR (400 MHz, CDCl$_3$) δ 7.68 (d, 1H), 7.54 (d, 1H), 7.50-7.36 (m, 3H), 7.32 (t, 1H), 7.25-7.17 (m, 4H), 7.11 (t, 1H), 7.08 (d, 1H), 6.72 (s, 1H), 4.65 (m, 1H), 3.73 (q, 1H), 3.66 (m, 1H), 3.63 (d, 1H), 3.55 (d, 1H), 3.42 (d, 1H), 3.28 (t, 1H), 2.78 (m, 1H), 2.57 (m, 2H), 2.30 (d, 2H), 2.13 (m, 2H), 2.01 (t, 2H), 1.76 (m, 4H), 1.48 (t, 2H), 1.10-1.30 (m, 3H)

EXAMPLE 46

Preparation of 4-[N-[1-[N-(benzofuran-2-ylcarbonyl)amino]cyclohexanecarbonyl]amino]-1-[2-(2-oxazolidinon-1-yl)phenyl]piperidin-3-one In accordance with the same procedure as in Example 43, except that 2-chloroethyl chloroformate was used instead of 3-chloropivaloyl chloride in Step 3 thereof, 75 mg of the titled compound was prepared.

$^1$H-NMR (400 MHz, CDCl$_3$) δ 7.70 (d, 1H), 7.68 (m, 4H), 7.33 (m, 2H), 7.26 (m, 1H), 7.16 (m, 1H), 6.72 (s, 1H), 4.70 (m, 1H), 4.50 (m, 2H), 4.01 (q, 1H), 3.92 (q, 1H), 3.72 (d, 1H), 3.69 (d, 1H), 3.36 (m, 1H), 3.15 (m, 1H), 2.74 (m, 1H), 2.31 (m, 2H), 2.01 (m, 2H), 1.78 (m, 4H)

EXAMPLE 47

Preparation of 4-[N-[1-[N-(benzofuran-2-ylcarbonyl)amino]cyclohexanecarbonyl]amino]-1-[2-(2-imidazolidinon-1-yl)phenyl]piperidin-3-one In accordance with the same procedure as in Example 43, except that 2-chloroethyl isocyanate was used instead of 3-chloropivaloyl chloride in Step 3 thereof, 80 mg of the titled compound was prepared.

$^1$H-NMR (400 MHz, CDCl$_3$) δ 7.69 (d, 1H), 7.60 (d, 1H), 7.50 (m, 2H), 7.34 (m, 2H), 7.31 (m, 1H), 7.03 (m, 1H), 7.01 (m, 1H), 6.74 (s, 1H), 4.93 (s, 1H), 4.66 (m, 1H), 3.86 (m, 2H), 3.50 (m, 4H), 3.15 (m, 1H), 2.76 (m, 1H), 2.33 (m, 2H), 2.00 (m, 2H), 1.77 (m, 4H), 1.52 (m, 2H), 1.20 (m, 1H)

EXAMPLE 48

Preparation of 4-[N-[1-[N-(benzofuran-2-ylcarbonyl)amino]cyclohexanecarbonyl]amino]-1-[2-[N-(ethoxycarbonyl)amino]phenyl]piperidin-3-one Step 1.

4-[N-[1-[N-(benzofuran-2-ylcarbonyl)amino]cyclohexanecarbonyl]amino]-1-[2-[N-(ethoxycarbonyl)amino]phenyl]piperidin-3-ol The solution of 4-[N-[1-[N-(benzofuran-2-ylcarbonyl)amino]cyclohexane carbonyl]amino]-1-(2-aminophenyl)piperidin-3-one (0.9 g) obtained in Step 2 of Example 43 in 20 ml of dichloromethane was cooled to 0° C. 0.54 ml of triethylamine and 0.37 ml of ethyl chloroformate were added to the reaction mixture, which was then stirred for about 3 hours at room temperature. 20 ml of ice water was added to the reaction mixture. The resulting organic layer was dried and concentrated on sodium sulfate. The resulting residue was purified with column chromatography to give 600 mg of the titled compound.

$^1$H-NMR (400 MHz, CDCl$_3$) δ 8.12 (d, 1H), 7.75 (d, 1H), 7.57 (m, 2H), 7.50 (m, 1H), 7.13 (m, 1H), 7.11 (m, 2H), 7.02 (m, 1H), 6.86 (s, 1H), 4.25 (s, 1H), 4.20 (q, 2H), 3.85 (m, 1H), 3.62 (m, 1H), 3.39 (m, 1H), 3.04 (m, 1H), 2.73 (m, 2H), 2.24 (m, 2H), 2.09 (m, 2H), 1.96 (m, 4H), 1.73 (m, 3H), 1.66 (m, 2H), 1.25 (m, 1H), 1.23 (t, 3H)

Step 2.

4-[N-[1-[N-(benzofuran-2-ylcarbonyl)amino]cyclohexanecarbonyl]amino]-1-[2-[N-(ethoxycarbonyl)amino]phenyl]piperidin-3-one To the solution of 4-[N-[1-[N-(benzofuran-2-ylcarbonyl)amino]cyclohexanecarbonyl]amino]-1-[2-[N-(ethoxycarbonyl)amino]phenyl]piperidin-3-ol (600 mg, 1.1 mmol) in 10 ml of dimethylsulfoxide (DMSOI), was added 0.46 ml of triethylamine (3.3 mmol). The reaction mixture was cooled to 0° C. Pyridine-SO$_3$ complex (0.51 g, 3.3 mmol) was added to the reaction mixture, which was then stirred for about 2 hours at room temperature. The reaction mixture was diluted with 20 ml of ethyl acetate, washed with brine. The resulting organic layer was dried and concentrated on sodium sulfate. The resulting residue was filtered and dried to give 320 mg of the titled compound as white color.

$^1$H-NMR (400 MHz, CDCl$_3$) δ 8.12 (d, 1H), 7.57 (d, 1H), 7.55 (m, 3H), 7.54 (m, 1H), 7.50 (m, 1H), 7.12 (m, 2H), 6.86 (s, 1H), 4.65 (m, 1H), 4.20 (q, 2H), 3.54 (d, 1H), 3.33 (d, 1H), 3.12 (m, 2H), 2.76 (m, 1H), 2.25 (m, 2H), 2.03 (m, 2H), 1.89 (m, 1H), 1.68 (m, 3H), 1.45 (m, 2H), 1.30 (m, 1H), 1.26 (t, 3H)

EXAMPLE 49

Preparation of 4-[N-[1-[N-(benzofuran-2-ylcarbonyl)amino]cyclohexanecarbonyl]amino]-1-[2-[N-(methoxycarbonyl)amino]phenyl]piperidin-3-one In accordance with the same procedure as in Example 48, except that methyl chloroformate was used instead of ethyl chloroformate in Step 1 thereof, 305 mg of the titled compound was prepared.

$^1$H-NMR (400 MHz, CDCl$_3$) δ 8.11 (d, 1H), 7.69(d, 1H), 7.54 (m, 3H), 7.52 (m, 1H), 7.33 (m, 1H), 7.31 (m, 2H), 7.03 (m, 1H), 6.76 (s, 1H), 4.66 (m, 1H), 3.75 (s, 3H), 3.58 (m, 5H), 1.76 (m, 2H), 1.32 (m, 1H)

EXAMPLE 50

Preparation of 4-[N-[1-[N-(benzofuran-2-ylcarbonyl)amino]cyclohexanecarbonyl]amino]-1-[2-[N-(4-chlorobutyryl)amino]phenyl]piperidin-3-one In accordance with the same procedure as in Example 48, except that 4-chlorobutyryl chloride was used instead of ethyl chloroformate in Step 1 thereof, 290 mg of the titled compound was prepared.

$^1$H-NMR (400 MHz, CDCl$_3$) δ 7.69 (d, 1H), 7.56 (d, 1H), 7.49-7.45 (m, 3H), 7.35-7.31 (m, 2H), 7.19 (d, 1H), 7.10 (d, 1H), 6.93 (d, 1H), 6.73 (s, 1H), 4.69 (m, 1H), 3.66 (m, 2H), 3.58 (d, 1H), 3.49 (d, 1H), 3.23 (d, 1H), 3.09 (t, H), 2.55 (m, 2H), 2.48 (t, 2H), 2.31 (m, 2H), 2.12 (m, 2H), 2.02 (m, 2H), 1.91 (m, 1H), 1.75 (m, 2H), 1.54 (t, 2H), 1.40 (m, 1H)

EXAMPLE 51

Preparation of 4-[N-[1-[N-(benzofuran-2-ylcarbonyl)amino]cyclohexanecarbonyl]amino]-1-[2-[N-(isobutyryl)amino]phenyl]piperidin-3-one In accordance with the same procedure as in Example 48, except that isobutyryl chloride was used instead of ethyl chloroformate in Step 1 thereof, 330 mg of the titled compound was prepared.

$^1$H-NMR (400 MHz, CDCl$_3$) δ 8.20 (d, 1H), 7.66 (d, 1H), 7.46-7.43 (m, 3H), 7.32-7.28 (m, 2H), 7.11-7.05 (m, 1H), 6.77 (d, 1H), 4.75 (m, 1H), 3.80-3.76 (m, 1H), 3.74 (m, 1H), 3.67-3.63 (m, 2H), 3.30-3.25 (m, 1H), 3.17-3.14 (m, 1H), 2.87-2.65 (m, 2H), 2.60-2.54 (m, 2H), 2.19-2.05 (m, 2H), 1:77-1.71 (m, 2H), 1.57-1.41 (m, 1H), 1.42-1.30 (m, 1H), 1.20-1.12 (m, 7H)

EXAMPLE 52

Preparation of 4-[N-[1-[N-(benzofuran-2-ylcarbonyl)amino]cyclohexanecarbonyl]amino]-1-[2-[N-(methoxyacetyl)amino]phenyl]piperidin-3-one In accordance with the same procedure as in Example 48, except that methoxyacetyl chloride was used instead of ethyl chloroformate in Step 1 thereof, 250 mg of the titled compound was prepared.

$^1$H-NMR (400 MHz, CDCl$_3$) δ 7.68 (d, 1H), 7.55-7.43 (m, 3H), 7.35-7.30 (m, 2H), 7.14-7.02 (m, 1H), 6.80(m, 1H), 4.81-4.75 (m, 1H), 3.80-3.76 (m, 1H), 3.67-3.63 (m, 2H), 3.48 (s, 3H), 3.45-3.25 (m, 3H), 3.17-3.14 (m, 1H), 2.78-2.72 (m, 1H), 2.55-2.50 (m, 2H), 2.36-2.30 (m, 1H), 2.23-2.12 (m, 2H), 1.77-1.71 (m, 2H), 1.57-1.41 (m, 1H), 1.30-1.25 (m, 1H)

EXAMPLE 53

Preparation of 4-[N-[1-[N-(benzofuran-2-ylcarbonyl)amino]cyclohexanecarbonyl]amino]-1-[2-[N-(cyclopropanecarbonyl)amino]phenyl]piperidin-3-one In accordance with the same procedure as in Example 48, except that cyclopropanecarbonyl chloride was used instead of ethyl chloroformate in Step 1 thereof, 150 mg of the titled compound was prepared.

$^1$H-NMR (400 MHz, CDCl$_3$) δ 7.70 (d, 1H), 7.50-7.40 (m, 3H), 7.35-7.05 (m, 3H), 6.85 (m, 1H), 4.78-4.75 (m, 1H), 3.80-3.76 (m, 1H), 3.76-3.70 (m, 1H), 3.65-3.60 (m, 2H), 3.30-3.25 (m, 1H), 3.17-3.14 (m, 1H), 2.78-2.72 (m, 1H), 2.57-2.51 (m, 2H), 2.40-2.28 (m, 2H), 2.20-2.00 (m, 3H), 1.98-1.62 (m, 4H), 1.57-1.41 (m, 3H), 1.30-1.20 (m, 1H)

EXAMPLE 54

Preparation of 4-[N-[1-[N-(benzofuran-2-ylcarbonyl)amino]cyclohexanecarbonyl]amino]-1-[2-[N-(3-phenylpropionyl)amino]phenyl]piperidin-3-one In accordance with the same procedure as in Example 48, except that 3-phenylpropionyl chloride was used instead of ethyl chloroformate in Step 1 thereof, 220 mg of the titled compound was prepared.

$^1$H-NMR (400 MHz, CDCl$_3$) δ 8.34 (d, 1H), 8.02 (s, 1H), 7.68 (d, 1H), 7.53 (d, 2H), 7.45 (m, 2H), 7.31 (m, 2H), 7.23 (m, 1H), 7.08 (m, 4H), 7.08 (m, 2H), 7.06 (m, 2H), 6.75 (s, 1H), 4.65 (m, 1H), 3.53 (d, 1H), 3.41 (d, 1H), 3.04 (m, 2H), 3.00 (m, 1H), 2.71 (m, 2H), 2.30 (m, 2H), 2.03 (m, 2H), 1.72 (m, 4H), 1.68 (m, 2H), 1.27 (m, 1H)

EXAMPLE 55

Preparation of 4-[N-[1-[N-(benzofuran-2-ylcarbonyl)amino]cyclohexanecarbonyl]amino]-1-[2-[N-(2-fluorobenzoyl)amino]phenyl]piperidin-3-one In accordance with the same procedure as in Example 48, except that 2-fluorobenzoyl chloride was used instead of ethyl chloroformate in Step 1 thereof, 220 mg of the titled compound was prepared.

$^1$H-NMR (400 MHz, CDCl$_3$) δ 9.91 (d, 1H), 8.63 (d, 1H), 8.18 (t, 1H), 7.79 (t, 1H), 7.43 (m, 1H), 7.21 (m, 4H), 7.20 (m, 4H), 7.04 (m, 2H), 6.68 (s, 1H) 5.27 (m, 1H), 4.13 (d, 1H), 3.31 (m, 1H), 3.00 (m, 2H), 2.87 (m, 1H), 2.34 (m, 2H), 2.02 (m, 1H), 2.00 (m, 4H), 1.67 (m, 1H), 1.64 (m, 3H), 1.22 (m, 1H)

EXAMPLE 56

Preparation of 4-[N-[1-[N-(benzofuran-2-ylcarbonyl)amino]cyclohexanecarbonyl]amino]-1-[2-[N-(acetyl)amino]phenyl]piperidin-3-one In accordance with the same procedure as in Example 48, except that acetyl chloride was used instead of ethyl chloroformate in Step 1 thereof, 190 mg of the titled compound was prepared.

$^1$H-NMR (400 MHz, CDCl$_3$) δ 8.31 (d, 1H), 7.70 (d, 1H), 7.56 (m, 1H), 7.54 (m, 2H), 7.33 (m, 1H), 7.15 (m, 2H), 7.23 (m, 1H), 7.08 (m, 4H), 7.08 (m, 2H), 7.06 (m, 3H), 6.65 (s, 1H), 4.99 (m, 1H), 4.37 (m, 1H), 3.16 (m, 1H), 2.81 (m, 1H), 2.79 (m, 2H), 2.27 (m, 3H), 2.25 (s, 3H), 2.00 (m, 2H), 1.74 (m, 4H), 1.67 (m, 2H), 1.31 (m, 1H)

EXAMPLE 57

Preparation of 4-[N-[1-[N-(benzofuran-2-ylcarbonyl)amino]cyclohexanecarbonyl]amino]-1-[2-[N-(2,5-dihydropyrrol-1-yl)amino]phenyl]piperidin-3-one Step 1.

4-[N-[1-[N-(benzofuran-2-ylcarbonyl)amino]cyclohexanecarbonyl]amino]-1-[2-[N-(2,5-dihydropyrrol-1-yl)amino]phenyl]piperidin-3-ol To the solution of cis-2-buten-1,4-diol diacetate (1.15 g) in 30 ml of dichloromethane, was added the solution of 4-[N-[1-[N-(benzofuran-2-ylcarbonyl)amino]cyclohexanecarbonyl]amino]-1-(2-aminophenyl)piperidin-3-ol (1.5 g) obtained in Step 2 of Example 43 in 20 ml of dimethylformamide. 0.44 ml of triethylamine was added to the reaction mixture, which was then stirred overnight at room temperature. 20 ml of ice water was added to the reaction mixture. The resulting organic layer was dried and concentrated on sodium sulfate. The resulting residue was purified with column chromatography to give 0.7 g of the titled compound.

$^1$H-NMR (400 MHz, CDCl$_3$) δ 7.80-7.00 (m, 6H), 7.7 (m, 1H), 6.17 (t, 2H), 4.8 (m, 1H), 3.78 (s, 2H), 3.67 (s, 2H), 3.45 (m, 3H), 3.30 (m, 1H), 3.00 (m, 1H), 2.69 (m, 1H), 2.33 (d, 2H), 2.01 (t, 2H), 1.80-1.68 (m, 2H), 1.43 (t, 2H), 1.26 (d, 2H)

Step 2.

4-[N-[1-[N-(benzofuran-2-ylcarbonyl)amino]cyclohexanecarbonyl]amino]-1-[2-[N-(2,5-dihydropyrrol-1-yl)amino]phenyl]piperidin-3-one To the solution of 4-[N-[1-[N-(benzofuran-2-ylcarbonyl)amino]cyclohexanecarbonyl]amino]-1-[2-[N-(2,5-dihydropyrrol-1-yl)amino]phenyl]piperidin-3-ol (0.7 g) obtained in Step 1 in 6 ml of dimethylsulfoxide (DMSO), was added 0.8 ml of triethylamine. The reaction mixture was cooled to 0° C. Pyridine-SO$_3$ complex (0.75 g) was added slowly to the reaction mixture, which was then stirred for about 2 hours at room temperature. The reaction mixture was diluted with 50 ml of ethyl acetate and washed with brine. The resulting organic layer was dried and concentrated on sodium sulfate. The resulting residue was filtered and dried to give 0.6 g of the titled compound as white color.

$^1$H-NMR (400 MHz, CDCl$_3$) δ 7.70 (d, 1H), 7.54 (d, 1H), 7.49-7.40 (m, 2H), 7.32-7.22 (m, 4H), 7.09 (t, 1H), 7.01 (d, 1H), 4.58 (m, 1H), 3.73-3.70 (m, 1H), 3.57-3.54 (m, 1H), 3.49-3.45 (m, 4H), 2.91-2.85 (m, 2H), 2.50(m, 1H), 2.32-2.28 (m, 2H), 1.98 (t, 2H), 1.77-1.55 (m, 7H), 1.35 (t, 1H)

EXAMPLE 58

Preparation of 4-[N-[1-[N-(benzofuran-2-ylcarbonyl)amino]cyclohexanecarbonyl]amino]-1-[2-(tetrazol-1-yl)phenyl]piperidin-3-one Step 1.

4-[N-[1-[N-(benzofuran-2-ylcarbonyl)amino]cyclohexanecarbonyl]amino]-1-[2-(tetrazol-1-yl)phenyl]piperidin-3-ol The mixture of 4-[N-[1-[N-(benzofuran-2-ylcarbonyl)amino]cyclohexanecarbonyl]amino]-1-(2-aminophenyl)piperidin-3-one (2 g, 4 mmol) obtained in Step 2 of Example 43, sodium azide (NaN$_3$; 409 mg, 6.2 mmol) and triethyl orthoformate (1.1 ml, 6.7 mmol) was refluxed in 10 ml of acetic acid for about 4 hours. The reaction mixture was cooled to room temperature. 10 ml of ice water was added to the reaction mixture, which was then stirred for about 48 hours. The resulting residue was filtered and dried to give 0.6 g of the titled compound.

$^1$H-NMR (400 MHz, CDCl$_3$) δ 9.39 (s, 1H), 7.62 (d, 1H), 7.43 (m, 3H), 7.22 (m, 2H), 7.19 (m, 3H), 7.11 (m, 2H), 4.26(s, 1H), 3.87 (m, 1H), 3.65 (m, 1H), 3.21 (m, 1H), 2.66 (m, 1H), 2.45 (m, 2H), 2.21 (m, 2H), 2.05 (m, 3H), 1.74 (m, 4H), 1.54 (m, 2H), 1.23 (m, 1H)

Step 2.

4-[N-[1-[N-(benzofuran-2-ylcarbonyl)amino]cyclohexanecarbonyl]amino]-1-[2-(tetrazol-1-yl)phenyl]piperidin-3-one To the solution of 4-[N-[1-[N-(benzofuran-2-ylcarbonyl)amino]cyclohexanecarbonyl]amino]-1-[2-(tetrazol-1-yl)phenyl]piperidin-3-ol (0.6 g) obtained in Step 1 in 10 ml of dimethylsulfoxide, was added 0.48 ml of triethylamine (3.4 mmol). The reaction mixture was cooled to 0° C. Pyridine-SO$_3$ complex (0.54 g, 3.4 mmol) was added to the reaction mixture, which was then stirred for about 2 hours at room temperature. The reaction mixture was diluted with 50 ml of ethyl acetate and washed with brine. The resulting organic layer was dried and concentrated on sodium sulfate. The resulting residue was filtered and dried to give 0.4 g of the titled compound.

$^1$H-NMR (400 MHz, CDCl$_3$) δ 9.08 (s, 1H), 7.67 (d, 1H), 7.53 (m, 2H), 7.49 (m, 1H), 7.33 (m, 2H), 7.25 (d, 2H), 6.76 (s, 1H), 4.56 (m, 1H), 3.60 (d, 1H), 3.48 (d, 1H), 3.05 (t, 1H) 2.94 (m, 1H), 2.35 (m, 1H), 2.29 (m, 2H), 1.97 (m, 2H), 1.75 (m, 4H), 1.52 (m, 3H), 1.49 (m, 1H)

EXAMPLE 59

Preparation of 4-[N-[1-[N-(benzofuran-2-ylcarbonyl)amino]cyclohexanecarbonyl]amino]-1-[2-(pyrrol-1-yl)-5-fluorophenyl]piperidin-3-one Step 1.

4-[N-[1-[N-(benzofuran-2-ylcarbonyl)amino]cyclohexanecarbonyl]amino]-1-(2-amino-5-fluorophenyl)piperidin-3-ol To the solution of 4-[N-[1-[N-(benzofuran-2-ylcarbonyl)amino]cyclohexanecarbonyl]amino]-3-piperidinol hydrochloride (6.0 g) obtained in Step 2 of Example 1 in 50 ml of ethanol, were added 3.7 ml 2,5-difluoronitrobenzene and 4.8 ml triethylamine. The reaction mixture was refluxed overnight and concentrated. The resulting residue was filtered and dried to give 7.2 g of the titled compound.

Step 2.

4-[N-[1-[N-(benzofuran-2-ylcarbonyl)amino]cyclohexanecarbonyl]amino]-1-[2-(pyrrol-1-yl)-5-fluoro phenyl]piperidin-3-ol The mixture of 4-[N-[1-[N-(benzofuran-2-ylcarbonyl)amino]cyclohexanecarbonyl]amino]-1-(2-amino-5-fluorophenyl)piperidin-3-ol (2 g) obtained in Step 1 and 0.96 ml of 2,5-dimethoxytetrahydrofuran was refluxed for 1 hour and concentrated under reduced pressure. The resulting residue was diluted with 70 ml of dichloromethane, washed with a saturated sodium bicarbonate solution and brine. The resulting organic layer was dried and concentrated on sodium sulfate. The resulting residue was purified with column chromatography to give 1.8 g of the titled compound as white color.

Step 3.

4-[N-[1-[N-(benzofuran-2-ylcarbonyl)amino]cyclohexanecarbonyl]amino]-1-[2-(pyrrol-1-yl)-5-fluorophenyl]piperidin-3-one To the solution 4-[N-[1-[N-(benzofuran-2-ylcarbonyl)amino]cyclohexanecarbonyl]amino]-1-[2-(pyrrol-1-yl)-5-fluorophenyl]piperidin-3-ol (1.8 g) obtained in Step 1 in 10 ml of dimethylsulfoxide, was added 2 ml of triethylamine. The reaction mixture was cooled to 0° C. Pyridine-SO$_3$ complex (1.8 g) was added to the reaction mixture, which was then stirred for about 2 hours at room temperature. The reaction mixture was diluted with 50 ml of ethyl acetate, washed with brine. The resulting organic layer was dried and concentrated on sodium sulfate. The resulting residue was purified with column chromatography to give 1.5 g of the titled compound.

$^1$H-NMR (400 MHz, CDCl$_3$) δ 7.70 (d, 1H), 7.54 (d, 1H), 7.49 (q, 2H), 7.32 (d, 1H), 7.29 (m, 1H), 7.17 (m, 1H), 6.85 (d, 1H), 6.69 (t, 1H), 6.27 (s, 1), 4.58 (t, 1H), 3.44 (q, 2H), 2.87 (m, 2H), 2.31 (m, 1H), 2.28 (d, 2H), 1.98 (m, 3H), 1.60-1.22 (m, 7H)

EXAMPLE 60

Preparation of 4-[N-[1-[N-(benzofuran-2-ylcarbonyl)amino]cyclohexanecarbonyl]amino]-1-[2-(pyrrol-1-yl)phenyl]piperidin-3-one In accordance with the same procedure as in Example 59, except that 4-[N-[1-[N-(benzofuran-2-ylcarbonyl)amino]cyclohexanecarbonyl]amino]-1-(2-aminophenyl)piperidin-3-ol obtained in Step 2 of Example 43 was used instead of 4-[N-[1-[N-(benzofuran-2-ylcarbonyl)amino]cyclohexanecarbonyl]amino]-1-(2-amino-5-fluorophenyl)piperidin-3-ol in Step 1 of Example 59, 1.3 g of the titled compound was prepared.

$^1$H-NMR (400 MHz, CDCl$_3$) δ 7.86 (d, 1H), 7.67 (d, 1H), 7.53 (m, 2H), 7.45 (m, 2H), 7.24 (m, 2H), 7.01 (m, 1H), 6.99 (m, 1H), 6.27 (s, 1H), 4.59 (m, 1H), 3.48 (m, 2H), 2.99 (m, 2H), 2.50 (m, 1H), 2.25 (m, 2H), 1.91 (m, 4H), 1.42 (m, 4H)

EXAMPLE 61

Preparation of 4-[N-[1-[N-(benzofuran-2-ylcarbonyl)amino]cyclohexanecarbonyl]amino]-1-[2-(N,N-dimethylcarbamoyl)phenyl]piperidin-3-one Step 1.

4-[N-[1-[N-(benzofuran-2-ylcarbonyl)amino]cyclohexanecarbonyl]amino]-1-(2-formylphenyl)piperidin-3-ol In accordance with the same procedure as in Step 3 of Example 1, except that 2-fluorobenzaldehyde was used instead of 1-fluorophenyl methyl sulfone, 5.3 g of the titled compound was prepared.

Step 2. 4-[N-[1-[N-(benzofuran-2-ylcarbonyl) amino]cyclohexanecarbonyl]amino]-1-[2-(N,N-dimethylcarbamoyl)phenyl]piperidin-3-ol To the solution of 4-[N-[1-[N-(benzofuran-2-ylcarbonyl) amino]cyclohexanecarbonyl]amino]-1-(2-formylphenyl)piperidin-3-ol (4.0 g) obtained in Step 1 and sodium hydrogen phosphate ($NaH_3PO_4$, 340 mg) in the mixed solvent of 20 ml of acetonitrile and 6 ml of water, were added 1.0 ml of 35%-hydrogen peroxide solution and 30 ml of sodium hypochlorite solution ($NaClO_4$) at 10° C. The reaction mixture was stirred for about 1 hour at room temperature. Sodium sulfite (1.0 g) was added to the reaction mixture, which was then acidified with 10%-hydrochloride solution. The resulting solid was filtered and dried to give 3.6 g of a solid. The solution of the resulting solid (2.5 g), dimethyamine hydrochloride (1.0 g) and benzotriazol-1-yloxytripyrrolidinophosphonium hexaphosphate (PyBOP, 3.1 g) in 30 ml of dichloromethane was cooled to 0° C. Diisopropylethylamine (DIEA, 1.0 g) was added to the reaction mixture, which was then stirred for about 4 hours at room temperature. 30 ml of water was added to the reaction mixture. The resulting organic layer was dried and concentrated on sodium sulfate. The resulting residue was purified with column chromatography to give 1.5 g of the titled compound.

$^1$H-NMR (400 MHz, $CDCl_3$) δ 7.69 (d, 1H), 7.57 (m, 2H), 7.49 (m, 2H), 7.31 (m, 1H), 7.06 (t, 1H), 6.97 (d, 1H), 6.73 (s, 1H), 3.78 (m, 1H), 3.64 (m, 2H), 3.41 (m, 2H), 3.01 (s, 3H), 2.78 (m, 4H), 2.31 (broad, 2H), 2.00 (m, 3H), 1.75 (m, 2H), 1.52 (m, 2H), 1.38 (m, 1H)

Step 3.

4-[N-[1-[N-(benzofuran-2-ylcarbonyl)amino]cyclohexanecarbonyl]amino]-1-[2-(N,N-dimethylcarbamoyl)phenyl]piperidin-3-one To the solution of 4-[N-[1-[N-(benzofuran-2-ylcarbonyl) amino]cyclohexanecarbonyl]amino]-1-[2-(N,N-dimethylcarbamoyl)phenyl]piperidin-3-ol (1.8 g) obtained in Step 2 in 10 ml of dimethylsulfoxide (DMSO), was added 2 ml of triethylamine. The reaction mixture was cooled to 0° C. Pyridine-$SO_3$ complex (1.8 g) was added slowly to the reaction mixture, which was then stirred for about 2 hours at room temperature. The reaction mixture was diluted with 50 ml of ethyl acetate, washed with brine. The resulting organic layer was dried and concentrated on sodium sulfate. The resulting residue was purified with column chromatography to give 1.2 g of the titled compound.

$^1$H-NMR (400 MHz, $CDCl_3$) δ 7.69 (d, 1H), 7.56-7.45 (m, 4H), 7.34-7.23 (m, 3H), 7.07 (s, 1H), 6.97 (t, 1H), 6.64 (s, 1H), 4.63 (s, 1H), 3.79-3.29 (m, 4H), 3.07 (s, 1H), 2.77 (s, 3H), 2.64 (s, 1H), 2.30 (d, 2H), 2.01 (t, 2H), 1.75-1.69 (m, 5H), 1.43 (d, 2H), 1.22 (m, 2H)

EXAMPLE 62

Preparation of 4-[N-[1-[N-(benzofuran-2-ylcarbonyl)amino]cyclohexanecarbonyl]amino]-1-[2-(N-methylcarbamoyl)phenyl]piperidin-3-one In accordance with the same procedure as in Example 61, except methylamine was used instead of dimethylamine hydrochloride in Step 1 thereof, 1.05 g of the titled compound was prepared.

$^1$H-NMR (400 MHz, $CDCl_3$) δ 8.56 (broad, 1H), 8.05 (d, 1H), 7.70 (d, 1H), 7.54 (d, 1H), 7.49-7.22 (m, 7H), 7.12 (t, 1H), 6.75 (s, 1H), 4.62 (t, 1H), 3.72 (m, 1H), 3.66 (s, 2H), 3.27 (q, 2H), 2.96 (s, 3H), 2.78 (m, 2H), 2.31 (d, 2H), 1.99 (t, 2H), 1.78 (m, 5H), 1.55 (m, 2H), 1.22 (m, 2H)

EXAMPLE 63

Preparation of 4-[N-[1-[N-(benzofuran-2-ylcarbonyl)amino]cyclohexanecarbonyl]amino]-1-(2-carboxyphenyl)piperidin-3-one To the solution of 4-[N-[1-[N-(benzofuran-2-ylcarbonyl) amino]cyclohexanecarbonyl]amino]-1-(2-formylphenyl)piperidin-3-one (300 mg, 0.62 mmol) obtained in Example 15 and sodium hydrogen phosphate (22 mg, $NaH_3PO_4$) in the mixed solvent of 1 ml of acetonitrile and 0.5 ml of water, was added 35%-hydrogen peroxide solution (0.1 ml) and 3 ml of sodium hypochlorite solution ($NaClO_4$; 78 mg) at 10° C. The reaction mixture was stirred for about 1 hour at room temperature. Sodium sulfite (1.0 g) was added to the reaction mixture, which was then acidified with 10%-hydrochloride solution. The resulting solid was filtered and dried to give 150 mg of the titled compound.

$^1$H-NMR (400 MHz, $CDCl_3$) δ 7.55-6.74 (m, 9H), 4.63 (m, 1H), 3.73-3.59 (m, 4H), 3.51-3.45 (m, 2H), 2.78 (m, 2H), 2.31 (d, 2H), 1.99 (t, 2H), 1.78 (m, 5H), 1.55 (m, 2H), 1.22 (m, 2H)

EXAMPLE 64

Preparation of 4-[N-[1-[N-(benzofuran-2-ylcarbonyl)amino]cyclohexanecarbonyl]amino]-1-(4-carboxyphenyl)piperidin-3-one In accordance with the same procedure as in Example 63, except 4-[N-[1-[N-(benzofuran-2-ylcarbonyl)amino]cyclohexanecarbonyl]amino]-1-(4-formylphenyl)piperidin-3-one obtained in Example 14 was used instead of 4-[N-[1-[N-(benzofuran-2-ylcarbonyl)amino]cyclohexanecarbonyl] amino]-1-(2-formylphenyl)piperidin-3-one, 130 mg of the titled compound was prepared.

$^1$H-NMR (400 MHz, $CDCl_3$) δ 8.04 (d, 1H), 7.67 (d, 1H), 7.50 (m, 3H), 7.28 (m, 3H), 6.95 (s, 1H), 4.57 (m, 1H), 4.55-3.90 (m, 4H), 2.27 (m, 2H), 2.20 (m, 2H), 1.98 (m, 2H), 1.55 (m, 2H), 1.20 (m, 1H)

EXAMPLE 65

Preparation of 4-[N-[1-[N-(benzofuran-2-ylcarbonyl)amino]cyclohexanecarbonyl]amino]-1-[2-(1,3-oxazol-5-yl)phenyl]piperidin-3-one Step 1.

4-[N-[1-[N-(benzofuran-2-ylcarbonyl)amino]cyclohexanecarbonyl]amino]-1-[2-(1,3-oxazol-5-yl)phenyl]piperidin-3-ol The mixture of 4-[N-[1-[N-(benzofuran-2-ylcarbonyl) amino]cyclohexanecarbonyl]amino]-1-(2-formylphenyl)piperidin-3-ol (3 g, 6 mmol) obtained in Step 1 of Example 61, photassium carbonate (2 g, 20 mmol) and p-toluenesulfonylmethyl isocyanate (TosMIC; 1.8 g, 9 mmol) was refluxed in 500 ml of methanol for about 2 hours. 150 ml of water was added to the concentrated reaction mixture, which was then extracted with dichloromethane. The resulting organic layer was dried and concentrated on sodium sulfate. The resulting residue was purified with column chromatography to give 3.2 g of the titled compound.

¹H-NMR (400 MHz, CDCl₃) δ 7.89 (s, 1H), 7.71 (m, 3H), 7.54 (m, 1H), 7.32 (m, 1H), 7.26 (m, 1H), 7.22 (m, 2H), 6.88 (m, 1H), 6.82 (s, 1H), 4.16 (s, 1H), 3.85 (m, 1H), 3.69 (m, 1H), 3.34 (m, 1H), 3.06 (m, 1H), 2.73 (m, 2H), 2.28 (m, 2H), 2.00 (m, 3H), 1.79 (m, 4H), 1.54 (m, 2H), 1.32 (m, 1H)

Step 2.

4-[N-[1-[N-(benzofuran-2-ylcarbonyl)amino]cyclohexanecarbonyl]amino]-1-[2-(1,3-oxazol-5-yl)phenyl]piperidin-3-one To the solution of 4-[N-[1-[N-(benzofuran-2-ylcarbonyl)amino]cyclohexanecarbonyl]amino]-1-[2-(1,3-oxazol-5-yl)phenyl]piperidin-3-ol (3.36 g, 6 mmol) obtained in Step 1 in 20 ml of dimethyl sulfoxide (DMSO), was added 2.7 ml of triethylamine (19 mmol). The reaction mixture was cooled to 0° C. Pyridine-SO₃ complex (3.04 g, 19 mmol) was added to the reaction mixture, which was then stirred for about 2 hours at room temperature. The reaction mixture was diluted with 100 ml of ethyl acetate, washed with brine. The resulting organic layer was dried and concentrated on sodium sulfate. The resulting residue was purified with column chromatography to give 1.67 g of the titled compound.

¹H-NMR (400 MHz, CDCl₃) δ 7.75 (s, 1H), 7.89 (d, 1H), 7.75 (d, 1H), 7.60 (m, 3H), 7.41 (m, 2H), 7.33 (m, 2H), 7.19 (m, 2H), 6.73 (s, 1H), 4.65 (m, 1H), 3.65 (q, 2H), 3.26 (m, 2H), 3.70 (m, 1H), 2.36 (m, 2H), 2.02 (m, 2H), 1.79 (m, 4H), 1.55 (m, 2H)

EXAMPLE 66

Preparation of 4-[N-[1-[N-(benzofuran-2-ylcarbonyl)amino]cyclohexanecarbonyl]amino]-1-(2-hydroxyphenyl)piperidin-3-one Step 1.

4-[N-[1-[N-(benzofuran-2-ylcarbonyl)amino]cyclohexanecarbonyl]amino]-1-(2-hydroxyphenyl)piperidin-3-ol To the solution of 4-[N-[1-[N-(benzofuran-2-ylcarbonyl)amino]cyclohexanecarbonyl]amino]-1-(2-formylphenyl)piperidin-3-ol (1.38 g, 2.8 mmol) obtained in Step 1 of Example 61 in 50 ml of chloroform, was added 486 mg of m-chloroperbenzoic acid (5.6 mmol). The reaction mixture was stirred for about 2 hours at room temperature. The resulting organic layer was washed with the solutions of sulfurous acid and sodium bicarbonate, dried on sodium sulfate. The resulting ester residue was dissolved in 100 ml of methanol and was added a drop of concentrated hydrochloride thereto. The reaction mixture was stirred for about 1 hour, was added sodium bicarbonate (0.5 g) thereto. The reaction mixture was concentrated. The resulting residue was purified with column chromatography to give 1.0 g of the titled compound.

Step 2.

4-[N-[1-[N-(benzofuran-2-ylcarbonyl)amino]cyclohexanecarbonyl]amino]-1-(2-hydroxyphenyl)phenyl]piperidin-3-one The solution of 4-[N-[1-[N-(benzofuran-2-ylcarbonyl)amino]cyclohexanecarbonyl]amino]-1-(2-hydroxyphenyl)piperidin-3-ol (200 mg, 0.41 mmol) obtained in Step 1 in 10 ml of dimethyl sulfoxide (DMSO) was cooled to 0° C. and was added 199 mg of pyridine-SO₃ complex (1.25 mmol) thereto. The reaction mixture was stirred for about 2 hours at room temperature, diluted with 100 ml of ethyl acetate, and washed with brine. The resulting organic layer was dried and concentrated on sodium sulfate. The resulting residue was purified with column chromatography to give 120 mg of the titled compound.

¹H-NMR (400 MHz, CDCl₃) δ 7.68 (d, 1H), 7.54 (d, 1H), 7.53 (m, 6H), 7.42 (m, 1H), 7.01 (m, 1H), 6.86 (d, 1H), 4.81 (m, 1H), 3.91 (t, 1H), 3.45 (m, 2H), 2.92 (m, 1H), 2.35 (m, 3H) 2.2.04 (m, 3H), 2.35 (m, 2H), 2.07 (m, 2H), 1.65 (m, 4H), 1.52 (m, 2H), 1.35 (m, 1H)

EXAMPLE 67

Preparation of 4-[N-[1-[N-(benzofuran-2-ylcarbonyl)amino]cyclohexanecarbonyl]amino]-1-[2-(1H-tetrazol-5-yl)phenyl]piperidin-3-one Step 1.

4-[N-[1-[N-(benzofuran-2-ylcarbonyl)amino]cyclohexanecarbonyl]amino]-1-(2-cyanophenyl)piperidine-3-ol In accordance with the same procedure as in Step 3 of Example 1, except that 2-fluorobenzonitrile was used instead of 1-fluorophenyl methyl sulfone, 2.5 g of the titled compound was prepared.

Step 2.

4-[N-[1-[N-(benzofuran-2-ylcarbonyl)amino]cyclohexanecarbonyl]amino]-1-[2-(1H-tetrazol-5-yl)phenyl]piperidin-3-ol To the solution of 4-[N-[1-[N-(benzofuran-2-ylcarbonyl)amino]cyclohexanecarbonyl]amino]-1-(2-cyanophenyl)piperidin-3-ol (700 mg, 1.43 mmol) obtained in Step 1 in 20 ml of dimethylformamide, were added ammonium chloride (769 mg) and sodium azide (934 mg). The reaction mixture was stirred for about 12 hours at 120° C. 20 ml of water was added to the reaction mixture, which was then acidified with a concentrated hydrochloride solution. The resulting solid was filtered and dissolved in dichloromethane. The resulting residue was purified with column chromatography to give 120 mg of the titled compound.

Step 3.

4-[N-[1-[N-(benzofuran-2-ylcarbonyl)amino]cyclohexanecarbonyl]amino]-1-[2-(1H-tetrazol-5-yl)phenyl]piperidin-3-one To the solution of 4-[N-[1-[N-(benzofuran-2-ylcarbonyl)amino]cyclohexanecarbonyl]amino]-1-[2-(1H-tetrazol-5-yl)phenyl]piperidin-3-ol (120 mg, 0.22 mmol) obtained in Step 2 in 5 ml of dimethyl sulfoxide (DMSO), was added 0.093 ml of triethylamine (0.66 mmol). The reaction mixture was cooled to 0° C. Pyridine-SO₃ complex (103 mg, 0.66 mmol) was added to the reaction mixture, which was then stirred for about 2 hours at room temperature. The reaction mixture was diluted with 100 ml of ethyl acetate, washed with brine. The resulting organic layer was dried on sodium sulfate. The resulting residue was purified with column chromatography to give 50 mg of the titled compound.

¹H-NMR (400 MHz, CDCl₃) δ 7.75-7.64 (m, 4H), 7.53-7.44 (m, 9H), 7.42 (d, 1H), 7.35-7.26 (m, 2H), 6.74 (s, 1H), 4.56 (m, 1H), 4.00 (q, 1H), 3.86 (q, 1H), 2.89 (m, 1H), 2.34 (m, 2H), 2.24-2.18 (m, 3H), 2.02 (m, 2H), 1.91 (m, 1H), 1.75 (m, 2H), 1.54 (t, 2H), 1.40 (m, 1H)

EXAMPLE 68

Preparation of 4-[N-[1-[N-(benzofuran-2-ylcarbonyl)amino]cyclohexanecarbonyl]amino]-1-(2-methylsulfinylphenyl)phenyl]piperidin-3-one The solution of 4-[N-[1-[N-(benzofuran-2-ylcarbonyl)amino]cyclohexanecarbonyl]amino]-1-(2-methylthiophenyl)piperidin-3-one (68 mg, 0.13 mmol) obtained in Example 36 in 2 ml of dichloromethane was cooled to −78° C. 30 mg of 70% 3-chloroperbenzoic acid was added to the reaction mixture, which was then stirred for about 1 hour at room temperature. The resulting organic layer was washed with a saturated sodium bicarbonate solution, dried and concentrated on sodium sulfate. The resulting residue was purified with column chromatography to give 30 mg of the titled compound.

Rf=0.1 (CH₂Cl₂/ether=1:1) ¹H-NMR (400 MHz, CDCl₃) δ 7.92 (d, 1H), 7.69 (d, 1H), 7.42 (m, 6H), 7.29 (m, 1H), 7.15 (m, 1H), 6.78 (d, 1H), 4.65 (m, 1H), 3.75 (t, 1H), 3.45 (m, 2H), 3.22 (m, 1H), 2.75 (s, 1H) 2.71 (s, 3H), 2.35 (m, 2H), 2.07 (m, 2H), 1.65 (m, 4H), 1.52 (m, 2H), 1.35 (m, 1H)

EXAMPLE 69

Preparation of 4-[N-[1-[N-(benzofuran-2-ylcarbonyl)amino]cyclohexanecarbonyl]amino]-1-(2-ethylsulfinylphenyl)phenyl]piperidin-3-one The solution of 4-[N-[1-[N-(benzofuran-2-ylcarbonyl)amino]cyclohexanecarbonyl]amino]-1-(2-ethylthiophenyl)piperidin-3-one (38 mg) obtained in Example 42 was cooled to −78° C. 70% 3-chloroperbenzoic acid (20 mg) was added to the reaction mixture, which was then stirred for about 1 hour at room temperature. The resulting organic layer was washed with a saturated sodium bicarbonate solution, dried and concentrated on sodium sulfate. The resulting residue was purified with column chromatography to give 22 mg of the titled compound.

¹H-NMR (400 MHz, CDCl₃) δ 7.87 (d, 1H), 7.74 (d, 1H), 7.53 (m, 6H), 7.33 (m, 3H), 7.15 (dd, 1H), 6.73 (d, 1H), 4.65 (m, 1H), 3.69 (d, 1H), 3.55 (d, 1H), 3.45 (d, 1H), 3.15 (t, 1H), 2.89 (q, 2H), 2.71 (m, 1H), 2.31 (d, 2H), 2.05 (t, 2H), 1.89 (m, 1H), 1.75 (m, 3H), 1.54 (m, 2H), 1.36 (m, 1H) 1.34 (t, 3H)

EXAMPLE 70

Preparation of 4-[N-[1-[N-(benzofuran-2-ylcarbonyl)amino]cyclohexanecarbonyl]amino]-1-(2-isopropylsulfinylphenyl)piperidin-3-one Step 1.

4-[N-[1-[N-(benzofuran-2-ylcarbonyl)amino]cyclohexanecarbonyl]amino]-1-(2-isopropylthiophenyl)piperidin-3-ol In accordance with the same procedure as in Step 1 of Example 24, except that 1-bromo-2-isopropylthiobenzene was used instead of 1-bromo-4-fluoro-2-trifluoromethylbenzene, 66 mg of the titled compound was prepared.

Step 2.

4-[N-[1-[N-(benzofuran-2-ylcarbonyl)amino]cyclohexanecarbonyl]amino]-1-(2-isopropylsulfinylphenyl)piperidin-3-one To the solution of 4-[N-[1-[N-(benzofuran-2-ylcarbonyl)amino]cyclohexanecarbonyl]amino]-1-(2-isopropylthiophenyl)piperidin-3-ol (60 mg) obtained in Step 1 in 5 ml of dimethyl sulfoxide (DMSO), was added 0.093 ml of triethylamine (0.66 mmol). The reaction mixture was cooled to 0° C. Pyridine-SO₃ complex (103 mg, 0.66 mmol) was added to the reaction mixture, which was then stirred for about 2 hours at room temperature. The reaction mixture was diluted with 100 ml of ethyl acetate, washed with brine. The resulting organic layer was dried on sodium sulfate. The resulting residue was purified with column chromatography to give 50 mg of the titled compound.

¹H-NMR (400 MHz, CDCl₃) δ 7.70 (d, 1H), 7.60-7.40 (m, 4H), 7.33 (m, 1H), 7.25 (m, 2H), 7.15 (m, 1H), 7.05 (m, 1H), 6.98 (d, 1H), 6.73 (s, 1H), 4.66 (m, 1H), 3.71 (d, 1H), 3.61 (d, 1H), 3.51 (m, 1H), 3.43 (m, 1H), 3.15 (t, 1H), 2.71 (m, 1H), 2.33 (d, 2H), 1.98 (t, 2H), 1.85 (m, 1H), 1.72 (m, 3H), 1.55 (d, 3H), 1.53 (m, 2H), 1.35 (m, 1H), 1.26 (d, 3H)

EXAMPLE 71

Preparation of 4-[N-[1-[N-(benzofuran-2-ylcarbonyl)amino]cyclohexanecarbonyl]amino]-1-[2-N-(acryloyl)aminophenyl]piperidin-3-one In accordance with the same procedure as in Example 48, except acryloyl chloride was used instead of ethyl chloroformate in Step 1 thereof, 254 mg of the titled compound was prepared.

¹H-NMR (400 MHz, CDCl₃) δ 8.30 (s, 1H), 7.62 (d, 1H), 7.40-7.50(m, 3H), 6.41 (d, 1H), 5.83 (d, 1H), 4.70 (m, 1H), 3.64 (dd, 2H), 2.00-1.30 (m, 10H)

EXAMPLE 72

Preparation of 4-[N-[1-[N-(benzofuran-2-ylcarbonyl)amino]cyclohexanecarbonyl]amino]-1-[2-(3,3-dimethylureido)phenyl]piperidin-3-one In accordance with the same procedure as in Example 48, except dimethylcarbamoyl chloride was used instead of ethyl chloroformate in Step 1 thereof, 220 mg of the titled compound was prepared.

¹H-NMR (400 MHz, CDCl₃) δ 8.10 (d, 1H), 7.60-7.50 (m, 4H), 7.52-7.10 (m, 5H), 6.72 (s, 1H), 4.70 (m, 1H), 3.80-3.12 (m, 3H), 2.22-1.90 (m, 2H), 1.90-1.32 (m, 11H)

EXAMPLE 73

Preparation of 4-[N-[1-[N-(benzofuran-2-ylcarbonyl)amino]cyclohexanecarbonyl]amino]-1-[2-(methoxycarbonyl)phenyl]piperidin-3-one In accordance with the same procedure as in Example 24, except methyl 2-bromobenzoate was used instead of 1-bromo-4-fluoro-2-trifluoromethyl benzene in Step 1 thereof, 70 mg of the titled compound was prepared.

¹H-NMR (400 MHz, CDCl₃) δ 7.80 (m, 2H), 7.62 (m, 1H), 7.40-7.20 (m, 4H), 6.72 (s, 1H), 4.73 (m, 1H), 3.80 (s, 3H), 2.63 (m, 1H), 2.00-1.32 (m, 10H)

EXAMPLE 74

Preparation of 4-[N-[1-[N-(benzofuran-2-ylcarbonyl)amino]cyclohexanecarbonyl]amino]-1-phenylpiperidin-3-one In accordance with the same procedure as in Example 24, except methyl bromobenzene was used instead of 1-bromo-4-fluoro-2-trifluoromethyl benzene in Step 1 thereof, 35 mg of the titled compound was prepared.

¹H-NMR (400 MHz, CDCl₃) δ 7.57 (m, 6H), 7.31 (m, 2H), 6.89 (m, 1H), 6.45 (s, 1H), 7.05 (d, 1H), 6.73 (s, 1H), 4.66 (m, 1H), 4.22 (m, 1H), 4.05 (d, 1H), 3.75 (d, 1H), 3.53 (m, 1H), 3.44 (m, 1H), 2.75 (m, 1H), 2.31 (d, 1H), 2.05 (t, 2H), 1.89 (m, 1H), 1.75 (m, 3H), 1.54 (m, 2H), 1.36 (m, 1H)

EXAMPLE 75

Preparation of 4-[N-[1-[N-(benzofuran-2-ylcarbonyl)amino]cyclohexanecarbonyl]amino]-1-[2-(1,1-dioxo-isothiazolin-2-yl)phenyl)]piperidin-3-one In accordance with the same procedure as in Example 43, except 3-chloropropanesulfonyl chloride was used instead of 3-chloropivaloyl chloride in Step 3 thereof, 65 mg of the titled compound was prepared.

¹H-NMR (400 MHz, CDCl₃): 7.78 (d, 1H), 7.69 (m, 2H), 7.56 (m, 2H), 7.46 (m, 1H), 7.25 (m, 1H), 7.05(m, 2H), 6.71 (s, 1H), 4.65 (m, 1H), 3.94 (d, 1H), 3.85 (m, 1H), 3.58 (m, 1H), 3.51 (m, 1H), 3.26(m, 3H), 2.76 (m, 1H), 2.48 (m, 2H), 2.33 (m, 2H), 2.04 (m, 3H), 1.78 (m, 4H), 1.53 (m, 3H) 1.26 (m, 1H)

EXAMPLE 76

Preparation of 4-[N-[1-[N-(furan-2-ylcarbonyl)amino]cyclohexanecarbonyl]amino]-1-(2-methanesulfonylphenyl)piperidin-3-one Step 1. Methyl 1-[N-(furan-2-ylcarbonyl)amino]cyclohexanecarbonylate The solution of methyl 1-amino-1-cyclohexanecarboxylate (11.3 g, 58.5 mmol) and 2-furan-carbonylic acid (5.0 g) in 100 ml of dimethylformamide was cooled to 0° C. To the reaction mixture, were added diisopropylethiylamine (29 ml, 175.5 mmol), 1-hydroxybenzotriazole hydrate (9.1 g, 67.5 mmol) and 1-(3-dimethylaminopropyl)-3-ethylcarbodiimide hydrochloride (EDC-HCl; 12.9 g, 67.5 mmol). The reaction mixture was stirred for 24 hours at room temperature. 50 g of ice water was added to the reaction mixture to stop the reaction. The reaction mixture was diluted with 200 ml of ethyl acetate, washed with 10% citric acid solution and a saturated sodium bicarbonate solution, and then dried and concentrated on sodium sulfate to give 9.6 g of the titled compound. The titled compound was used in the next-step without further purifications Step 2. 1-[N-(furan-2-ylcarbonyl)amino]cyclohexanecarboxylic acid To the solution of methyl 1-[N-(furan-2-ylcarbonyl)amino]-1-cyclohexanecarboxylate (9.6 g) obtained in Step 1 in 100 ml of methanol, was added 2N-sodium hydroxide solution (50 ml). The reaction mixture was refluxed for 3 hours and concentrated. The resulting residue was diluted with 150 ml of water and washed with 100 ml of diethyl ether. 6N-hydrochloride was added dropwise to the resulting aqueous layer to adjust the pH of the solution to pH 3. The resulting white solid was filtered and dried to give the titled compound (6.1 g).

¹H-NMR (400 MHz, CDCl₃) δ 2.15 (d, 2H), 1.97 (t, 2H), 1.70 (m, 3H), 1.49-1.37 (m, 3H)

Step 3.

4-[N-[1-[N-(furan-2-ylcarbonyl)amino]cyclohexanecarbonyl]amino]-1-tert-butoxycarbonyl-3-piperidinol To the solution of tert-butyl 4-amino-3-hydroxypiperidin-1-carboxylate (20 g, 92 mmol) obtained in step 4 of Preparation Example 1 and 1-[N-(furan-2-ylcarbonyl)amino]cyclohexanecarboxylic acid (5.0 g) obtained in Step 2 in 70 ml of dimethylformamide, were added hydroxybenzotriazole (HOBt; 3.1 g, 23.1 mmol) and diisopropylethylamine (DIEA; 9.0 ml, 53.4 mmol). The reaction mixture was cooled to 0° C. and was added 1-(3-dimethylaminopropyl)-3-ethylcarbodiimide hydrochloride (EDC-HCl; 5.1 g, 26.7 mmol) thereto. The reaction mixture was stirred for 4 hours at room temperature. The reaction mixture was diluted with 200 ml of ethyl acetate, washed with 10% citric acid solution, a saturated sodium bicarbonate solution and brine. The resulting organic layer was dried and concentrated on sodium sulfate. The resulting residue was purified with column chromatography to give 4.3 g of the titled compound.

Step 4.

4-[N-[1-[N-(furan-2-ylcarbonyl)amino]cyclohexanecarbonyl]amino]-3-piperidinol hydrochloride The solution of 4-{1-[N-(furan-2-ylcarbonyl)amino]cyclohexane carbonyl}amino-1-tert-butoxycarbonyl-3-piperidinol (30 g) obtained in Step 3 in 100 ml of 3N-hydrochloride/ethyl acetate was stirred for about 2 hours at room temperature. 100 ml of diethyl ether was added to the reaction mixture, and then the resulting white solid was filtered and dried to give 3.6 g of the titled compound.

¹H-NMR (400 MHz, CDCl₃) δ 7.84 (d, 1H), 7.61 (s, 1H), 7.31 (d, 1H), 7.16 (d, 1H), 6.63 (s, 1H), 3.38 (m, 1H), 3.14 (m, 1H), 2.88 (d, 1H), 2.73 (d, 1H), 2.33 (t, 1H), 2.15 (m, 2H), 1.73 (m, 3H), 1.41 (m, 2H), 1.31 (m, 1H)

Step 5.

4-[N-[1-[N-(furan-2-ylcarbonyl)amino]cyclohexanecarbonyl]amino]-1-(2-methanesulfonylphenyl)piperidin-3-ol To the solution of 4-[N-[1-[N-(furan-2-ylcarbonyl)amino]cyclohexanecarbonyl]amino]-3-piperidinol hydrochloride (600 mg, 1.55 mmol) obtained in Step 4 and 1-flourophenyl methyl sulfone (272 g, 1.55 mmol) in 30 ml of dimethylformamide, was added potassium carbonate (500 mg). The reaction mixture was stirred overnight at about 100° C. and cooled to room temperature. The reaction mixture was diluted with 200 ml of ethyl acetate and washed with brine. The resulting organic layer was dried and concentrated on sodium sulfate. The resulting residue was purified with column chromatography to give 390 mg of the titled compound as white solid.

$^1$H-NMR (400 MHz, CDCl$_3$) δ 7.78 (d, 1H), 7.50 (s, 1H), 7.43 (m, 1H), 7.31 (m, 1H), 7.13 (m, 2H), 6.55 (m, 2H), 3.88 (m, 1H), 3.69 (m, 1H), 3.27 (m, 5H), 2.81 (m, 1H), 2.67 (t, 1H), 2.22 (t, 2H), 1.99 (m, 3H), 1.70 (m, 4H), 1.48-1.29 (m, 3H)

Step 6.

4-[N-[1-[N-(furan-2-ylcarbonyl)amino]cyclohexanecarbonyl]amino]-1-(2-methanesulonylphenyl)piperidin-3-one To the solution of 4-[N-[1-[N-(furan-2-ylcarbonyl)amino]cyclohexanecarbonyl]amino]-1-(2-methanesulfonylphenyl)piperidin-3-ol (0.39 g, 0.77 mmol) obtained in Step 5 in 3 ml of dimethylsulfoxide (DMSO), was added 0.4 ml of triethylamine. The reaction mixture was cooled to 0° C. Pyridine-SO$_3$ complex (0.4 g, 2.51 mmol) was added to the reaction mixture, which was then stirred for 2 hours. The reaction mixture was diluted with 20 ml of ethyl acetate, washed with brine. The resulting organic layer was dried and concentrated on sodium sulfate. The resulting residue was purified with column chromatography to give 155 mg of the titled compound as white solid.

$^1$H-NMR (400 MHz, CDCl$_3$) δ 8.1 (d, 1H), 7.6 (m, 2H), 6.5 (m, 1H), 6.4 (s, 1H), 4.7 (m, 1H), 3.7 (dd, 2H), 3.2 (s, 3H), 2.4 (m, 2H), 1.4-2.0 (m, 10H)

EXAMPLE 77

Preparation of 4-[N-[1-[N-(furan-2-ylcarbonyl)amino]cyclohexanecarbonyl]amino]-1-(3-fluoro-2-methylsulfonylphenyl)piperidin-3-one In accordance with the same procedure as in Example 76, except that 2,6-difluorophenyl methyl sulfone was used instead of 1-fluorophenyl methyl sulfone in Step 5 thereof, 230 mg of the titled compound was prepared.

$^1$H-NMR (400 MHz, CDCl$_3$) δ7.48 (m, 1H), 7.46 (m, 2H), 7.13 (d, 1H), 7.06 (m, 2H), 6.53 (d, 1H), 6.44 (s, 1H), 4.68 (m, 1H), 3.73 (m, 2H), 3.68 (d, 1H), 3.25 (s, 3H), 2.66 (m, 1H), 2.24 (d, 2H), 2.00 (t, 3H), 1.75 (m, 3H), 1.63 (m, 2H), 1.47 (m, 1H)

EXAMPLE 78

Preparation of 4-[N-[1-[N-(furan-2-ylcarbonyl)amino]cyclohexanecarbonyl]amino]-1-(4-fluoro-2-nitrophenyl)piperidin-3-one In accordance with the same procedure as in Example 76, except that 2,5-difluoronitrobenzene was used instead of 1-fluorophenyl methyl sulfone in Step 5 thereof, 170 mg of the titled compound was prepared.

$^1$H-NMR (400 MHz, CDCl$_3$) δ 7.50-7.22 (m, 5H), 6.55 (d, 1H), 6.32 (s, 1H), 4.70 (m, 1H), 3.86, (q, 3H), 3.41 (t, 1H), 2.78 (m, 1H), 2.31 (broad, 2H), 2.00 (m, 3H), 1.75 (m, 2H), 1.52 (m, 2H), 1.38 (m, 1H)

EXAMPLE 79

Preparation of 4-[N-[1-[N-(furan-2-ylcarbonyl)amino]cyclohexanecarbonyl]amino]-1-(4-fluoro-2-formylphenyl)piperidin-3-one In accordance with the same procedure as in Example 76, except that 2,5-difluorobenzaldehyde was used instead of 1-fluorophenyl methyl sulfone in Step 5 thereof, 190 mg of the titled compound was prepared.

$^1$H-NMR (400 MHz, CDCl$_3$) δ 10.32 (s, 1H), 7.77 (d, 1H), 7.52-7.42 (m, 2H), 7.15 (m, 2H), 6.53 (s, 1H), 4.65 (m, 1H), 3.58 (m, 2H), 3.34 (m, 1H), 3.14 (t, 1H), 2.70 (m, 1H), 2.38 (s, 3H), 2.23(m, 2H), 1.94 (m, 2H), 1.73-1.51 (m, 5H), 1.43-1.21 (m, 3H)

EXAMPLE 80

Preparation of 4-[N-[1-[N-(furan-2-ylcarbonyl)amino]cyclohexanecarbonyl]amino]-1-(2-isopropylsulfonylphenyl)piperidin-3-one In accordance with the same procedure as in Example 76, except that 1-fluorophenyl isopropyl sulfone was used instead of 1-fluorophenyl methyl sulfone in Step 5 thereof, 173 mg of the titled compound was prepared.

$^1$H-NMR (400 MHz, CDCl$_3$) δ 8.06 (d, 1H), 7.49 (t, 1H), 7.38 (m, 2H), 7.26 (m0, 2H), 7.15 (d, 1H), 6.53 (m, 1H), 6.44 (s, 1H), 6.65 (m, 1H), 3.80 (m, 2H), 3.74 (d, 2H), 3.15 (t, 1H), 2.67 (m, 1H), 2.17 (m, 2H), 1.98 (m, 3H), 1.72 (d, 3H), 1.50 (m, 2H), 1.47 (m, 2H), 1.31 (m, 1H), 1.29 (d, 3H), 1.09 (d, 3H)

EXAMPLE 81

Preparation of 4-[N-[1-[N-(furan-2-ylcarbonyl)amino]cyclohexanecarbonyl]amino]-1-(2-phenylsulfonylphenyl)piperidin-3-one In accordance with the same procedure as in Example 76, except that 2-fluorophenyl sulfone was used instead of 1-fluorophenyl methyl sulfone in Step 5 thereof, 150 mg of the titled compound was prepared.

$^1$H-NMR (400 MHz, CDCl$_3$): 7.63 (m, 1H), 7.50-7.15 (m, 10H), 6.71 (s, 1H), 4.38 (m, 1H), 3.67 (d, 1H), 3.46 (d, 1H), 3.34 (m, 1H), 3.21 (t, 1H), 2.63 (m, 1H), 2.26 (m, 2H), 1.94 (t, 2H), 1.71 (m, 3H), 1.47 (m, 3H), 1.26 (m, 3H)

EXAMPLE 82

Preparation of 4-[N-[1-[N-(furan-2-ylcarbonyl)amino]cyclohexanecarbonyl]amino]-1-(4-methoxybenzylsulfonylphenyl)piperidin-3-one In accordance with the same procedure as in Example 76, except that 2-fluorophenyl-(4-methoxy)benzyl sulfone was used instead of 1-fluorophenyl methyl sulfone in Step 5 thereof, 76 mg of the titled compound was prepared.

$^1$H-NMR (400 MHz, CDCl$_3$): 7.63 (m, 1H), 7.50-7.15 (m, 10H), 6.71 (s, 1H), 4.75 (m, 1H), 4.38 (m, 1H), 3.71 (s, 3H), 3.67 (d, 1H), 3.46 (d, 1H), 3.34 (m, 1H), 3.21 (t, 1H), 2.63 (m, 4H), 2.26 (m, 2H), 1.94 (t, 2H), 1.71 (m, 3H), 1.47 (m, 3H), 1.26 (m, 3H)

EXAMPLE 83

Preparation of 4-[N-[1-[N-(furan-2-ylcarbonyl)amino]cyclohexanecarbonyl]amino]-1-(4-fluoro-2-methylsulfonylphenyl)piperidin-3-one In accordance with the same procedure as in Example 76, except that 2,5-difluorophenyl methyl sulfone was used instead of 1-fluorophenyl methyl sulfone in Step 5 thereof, 150 mg of the titled compound was prepared.

$^1$H-NMR (400 MHz, CDCl$_3$) δ 7.8 (m, 1H), 7.52 (m, 2H), 7.41 (m, 2H), 7.15 (s, 1H), 6.52 (s, 1H), 6.40 (s, 1H), 4.62 (s, 1H), 3.21 (s, 3H), 2.18-1.31 (m, 12H)

EXAMPLE 84

Preparation of 4-[N-[1-[N-(furan-2-ylcarbonyl)amino]cyclohexanecarbonyl]amino]-1-(4-methoxy-2-methylsulfonylphenyl)piperidin-3-one In accordance with the same procedure as in Example 76, except that 2-fluoro-5-methoxyphenyl methyl sulfone was used instead of 1-fluorophenyl methyl sulfone in Step 5 thereof, 135 mg of the titled compound was prepared.

$^1$H-NMR (400 MHz, CDCl$_3$) δ 7.83 (m, 1H), 7.52 (m, 2H), 7.41 (m, 2H), 7.18 (s, 1H), 6.54 (s, 1H), 6.38 (s, 1H), 4.65 (s, 1H), 3.85 (s, 3H), 3.21 (s, 3H), 2.2-1.15 (m, 12H)

EXAMPLE 85

Preparation of 4-[N-[1-[N-(furan-2-ylcarbonyl)amino]cyclohexanecarbonyl]amino]-1-(4-fluoro-2-thiomethoxyphenyl)piperidin-3-one Step 1.

4-[N-[1-[N-(furan-2-ylcarbonyl)amino]cyclohexanecarbonyl]amino]-1-(4-fluoro-2-thiomethoxyphenyl)piperidin-3-ol To the suspension of 4-[N-[1-[N-(furan-2-ylcarbonyl)amino]cyclohexanecarbonyl]amino]-3-piperidinol hydrochloride (300 mg) obtained in Step 4 of Example 76 in 5 ml of toluene, were added 1-bromo-4-fluoro-2-thiomethoxybenzene (250 mg), cesium carbonate (1.72 g), (S)-2,2-bis(diphenylphosphino)-1,1-binaphtyl (BINAP; 150 mg) and tris(dibenzylideneacetone)dipalladium (122 mg). The reaction mixture was stirred for about 8 hours at 100° C. under nitrogen atmosphere. The reaction mixture was diluted with 30 ml of ethyl acetate, filtered and concentrated. The resulting residue was purified with column chromatography to give 179 mg of the titled compound.

$^1$H-NMR (400 MHz, CDCl$_3$) δ7.52 (m, 2H), 7.23 (m, 3H), 6.87 (d, 1H), 6.53 (d, 2H), 3.81 (m, 1H), 3.62 (m, 1H), 3.38 (m, 1H), 3.19 (m, 1H), 2.70 (m, 1H), 2.35 (s, 3H), 2.23(m, 2H), 1.94 (m, 2H), 1.73-1.51 (m, 5H), 1.43-1.21 (m, 3H)

Step 2.

4-[N-[1-[N-(benzofuran-2-ylcarbonyl)amino]cyclohexanecarbonyl]amino]-1-(4-fluoro-2-thiomethoxyphenyl)piperidin-3-one To the solution of 4-[N-[1-[N-(benzofuran-2-ylcarbonyl)amino]cyclohexanecarbonyl]amino]-1-(4-fluoro-2-thiomethoxyphenyl)piperidin-3-ol (0.15 g) obtained in Step 1 in 3 ml of dimethyl sulfoxide (DMSO), was added 0.16 ml of triethylamine. The reaction mixture was cooled to 0° C. Pyridine-SO$_3$ complex (0.15 g) was added to the reaction mixture, which was then stirred for about 4 hours at room temperature. The reaction mixture was diluted with 20 ml of ethyl acetate and washed with brine. The resulting organic layer was dried and concentrated. The resulting residue was purified with column chromatography to give 84 mg of the titled compound as white solid.

$^1$H-NMR (400 MHz, CDCl$_3$) δ 7.52 (s, 1H), 7.48 (d, 1H), 7.15 (d, 1H), 6.99 (m, 1H), 6.77 (m, 2H), 6.52 (m, 1H), 6.45 (s, 1H), 4.67 (m, 1H), 3.64 (d, 1H), 3.56 (d, 1H), 3.45 (m, 1H), 3.13 (m, 1H), 2.67 (m, 1H), 2.35 (s, 3H), 2.23 (m, 2H), 2.00 (m, 2H), 1.97 (m, 1H), 1.73 (m, 6H), 1.51 (m, 2H), 1.44 (m, 1H)

EXAMPLE 86

Preparation of 4-[N-[1-[N-(furan-2-ylcarbonyl)amino]cyclohexanecarbonyl]amino]-1-(2-cyanophenyl)piperidin-3-one In accordance with the same procedure as in Example 83, except that 2-bromobenzonitrile was used instead of 1-bromo-4-fluoro-2-thiomethoxy benzene in Step 1 thereof, 160 mg of the titled compound was prepared.

$^1$H-NMR (400 MHz, CDCl$_3$) δ 7.50 (d, 1H), 7.48 (m, 3H), 7.25 (m, 1H), 7.23 (d, 1H), 7.14 (t, 1H), 6.98 (d, 1H), 6.53 (q, 1H), 6.44 (s, 1H), 4.68 (m, 1H), 3.89 (dt, 3H), 3.41 (t, 1H), 2.75 (m, 1H), 2.27 (m, 2H), 2.00-1.94 (m, 3H), 1.73-1.69 (m, 3H), 1.43-1.21 (m, 3H)

EXAMPLE 87

Preparation of 4-[N-[1-[N-(furan-2-ylcarbonyl)amino]cyclohexanecarbonyl]amino]-1-(4-fluoro-2-methoxyacetylaminophenyl)piperidin-3-one Step 1.

4-[N-[1-[N-(furan-2-ylcarbonyl)amino]cyclohexanecarbonyl]amino]-1-(4-fluoro-2-nitrophenyl)piperidin-3-ol To the solution of 4-[N-[1-[N-(furan-2-ylcarbonyl)amino]cyclohexanecarbonyl]amino]-3-piperidinol hydrochloride (6.0 g) obtained in Step 4 of Example 76 in 50 ml of ethanol, were added 2,5-difluoronitrobenzene (3.7 ml) and triethylamine (4.8 ml). The reaction mixture was refluxed overnight and concentrated. The resulting yellow solid was filtered and dried to give 7.2 g of the titled compound.

$^1$H-NMR (400 MHz, CDCl$_3$) δ 7.52 (s, 1H), 7.48 (d, 1H), 7.15 (d, 1H), 6.99 (m, 1H), 6.77 (m, 2H), 6.52 (m, 1H), 6.45 (s, 1H), 4.67 (m, 1H), 3.64 (d, 1H), 3.56 (d, 1H), 3.45 (m, 1H), 3.13 (m, 1H), 2.77 (m, 2H), 2.23 (m, 2H), 2.00 (m, 2H), 1.97 (m, 1H), 1.73 (m, 6H), 1.51 (m, 2H), 1.44 (m, 1H)

Step 2.

4-[N-[1-[N-(furan-2-ylcarbonyl)amino]cyclohexanecarbonyl]amino]-1-(4-fluoro-2-aminophenyl)piperidine-3-ol To the solution of 4-[N-[1-[N-(furan-2-ylcarbonyl)amino]cyclohexanecarbonyl]amino]-1-(4-fluoro-2-nitrophenyl)piperidin-3-ol (7.0 g, 14.7 mmol) obtained in Step 1 in 70 ml of ethanol, was added tin (II) chloride hydrate (1.13 mg, 44.2 mmol). The reaction mixture was refluxed for about 4 hours at 80° C., and then cooled to room temperature and concentrated. The resulting residue was diluted with 100 ml of ethyl acetate, alkalized with 29% aqueous ammonia solution (pH 8), and then the resulting white solid was filtered out. 100 ml of distilled water was added to the resulting filtrate. The resulting organic layer was dried and concentrated on sodium sulfate to give the titled compound (5.1 g).

$^1$H-NMR (400 MHz, CDCl$_3$) δ 7.50 (d, 1H), 7.15 (d, 1H), 7.08 (d, 1H), 6.93 (m, 1H), 6.55 (q, H), 6.49 (s, 1H), 6.38 (m, 2H), 4.10 (broad, 2H), 3.81 (m, 1H), 3.65 (m, 1H), 3.24 (d, 1H), 3.01 (d, 1H), 2.64 (m, 2H), 2.23 (m, 2H), 2.00 (m, 3H), 1.75 (m, 4H), 1.46-1.27 (m, 3H)

4-[N-[1-[N-(furan-2-ylcarbonyl)amino]cyclohexanecarbonyl]amino]-1-(4-fluoro-2-methoxyacetylaminophenyl)piperidin-3-ol The solution of 4-[N-[1-[N-(furan-2-ylcarbonyl)amino]cyclohexanecarbonyl]amino]-1-(4-fluoro-2-aminophenyl)piperidin-3-ol (1.0 g, 2.24 mmol) obtained in Step 2 in 30 ml of tetrahydrofuran was cooled to 0° C. Sodium carbonate (350 mg, 3.36 mmol) and methoxyacetyl chloride (0.53 mg, 5.82 mmol) was added to the reaction mixture, which was then stirred for 4 hours. 20 ml of ice water was added to the reaction mixture, which was then concentrated and extracted with 50 ml of ethyl acetate. The resulting organic layer was dried and concentrated on sodium sulfate. The resulting residue was crystallized with ethyl acetate to give 1.1 g of the titled compound.

Step 4.

4-[N-[1-[N-(furan-2-ylcarbonyl)amino]cyclohexanecarbonyl]amino]-1-(4-fluoro-2-methoxyacetylaminophenyl)piperidin-3-one To the solution of 4-[N-[1-[N-(benzofuran-2-ylcarbonyl)amino]cyclohexanecarbonyl]amino]-1-(4-fluoro-2-methoxyacetylaminophenyl)piperidin-3-ol (1.1 g) obtained in Step 3 in 5 ml of dimethyl sulfoxide, was added dropwise 1.2 ml of triethylamine. The reaction mixture was cooled to 0° C. Pyridine-SO$_3$ complex (0.9 g) was added to the reaction mixture, which was then stirred for about 4 hours at room temperature. The reaction mixture was diluted with 20 ml of ethyl acetate and washed with brine. The resulting organic layer was dried and concentrated on sodium sulfate. The resulting residue was purified with column chromatography to give 820 mg of the titled compound.

$^1$H-NMR (400 MHz, CDCl$_3$) δ 9.42 (s, 1H), 8.25 (d, 1H), 7.58 (d, 1H), 7.49 (s, 1H), 7.11 (m, 2H), 6.79 (m, 1H), 6.54 (d, 1H), 6.44 (s, 1H), 4.69 (m, 1H), 4.00 (s, 2H), 3.63 (d, 1H), 3.45 (m, 4H), 3.17 (m, 2H), 2.78 (m, 1H), 2.31 (broad, 2H), 2.00 (m, 3H), 1.75 (m, 2H), 1.52 (m, 2H), 1.38 (m, 1H)

EXAMPLE 88

Preparation of 4-[N-[1-[N-(furan-2-ylcarbonyl)amino]cyclohexanecarbonyl]amino]-1-(4-fluoro-2-methoxycarbonylaminophenyl)piperidin-3-one In accordance with the same procedure as in Example 87, except that methylchloroformate was used instead of methoxyacetyl chloride in Step 3 thereof, 671 mg of the titled compound was prepared.

$^1$H-NMR (400 MHz, CDCl$_3$) δ 7.91 (d, 1H), 7.71 (s, 1H), 7.50 (m, 2H), 7.16 (m, 2H), 6.77 (m, 1H), 6.55 (d, 1H), 6.45 (s, 1H), 4.66 (m, 1H), 3.78 (s, 3H), 3.53 (d, 1H), 3.43 (d, 1H), 3.19 (t, 1H), 3.07 (d, 1H), 2.78 (m, 1H), 2.26 (m, 2H), 2.00 (m, 3H), 1.75 (m, 2H), 1.48 (m, 2H), 1.21 (m, 1H)

EXAMPLE 89

Preparation of 4-[N-[1-[N-(furan-2-ylcarbonyl)amino]cyclohexanecarbonyl]amino]-1-(4-fluoro-2-cyclopropylcarbonylaminophenyl)piperidin-3-one In accordance with the same procedure as in Example 87, except that cyclopropylcarbonyl chloride was used instead of methoxyacetyl chloride in Step 3 thereof, 670 mg of the titled compound was prepared.

$^1$H-NMR (400 MHz, CDCl$_3$) δ 8.51 (s, 1H), 8.19 (d, 1H), 7.62 (d, 1H), 7.50 (s, 1H), 7.15 (m, 2H), 6.74 (m, 1H), 6.55 (d, 1H), 6.44 (s, 1H), 4.65 (m, 1H), 3.58 (d, 1H), 3.48 (d, 1H), 3.23 (t, 1H), 3.07 (d, 1H), 2.80 (m, 1H), 2.31 (broad, 2H), 2.00 (m, 3H), 1.75 (m, 2H), 1.52 (m, 2H), 1.38 (m, 1H), 1.09 (q, 3H), 0.88 (q, 3H)

EXAMPLE 90

Preparation of 4-[N-[1-[N-(furan-2-ylcarbonyl)amino]cyclohexanecarbonyl]amino]-1-(4-fluoro-2-isobutyrylaminophenyl)piperidin-3-one In accordance with the same procedure as in Example 87, except that isobutyryl chloride was used instead of methoxyacetyl chloride in Step 3 thereof, 522 mg of the titled compound was prepared.

$^1$H-NMR (400 MHz, CDCl$_3$) δ 8.36 (s, 1H), 8.23 (dd, 1H), 7.59 (d, 1H), 7.50 (s, 1H), 7.15 (m, 2H), 6.75 (m, 1H), 6.55 (d, 1H), 6.45 (s, 1H), 4.65 (m, 1H), 3.55 (d, 1H), 3.46 (d, 1H), 3.25 (t, 1H), 3.07 (d, 1H), 2.80 (m, 1H), 2.31 (broad, 2H), 2.00 (m, 3H), 1.75 (m, 2H), 1.52 (m, 2H), 1.38 (m, 1H), 1.21 (m, 6H)

EXAMPLE 91

Preparation of 4-[N-[1-[N-(furan-2-ylcarbonyl)amino]cyclohexanecarbonyl]amino]-1-[4-fluoro-2-(4-chlorobutyryl)aminophenyl]piperidin-3-one In accordance with the same procedure as in Example 87, except that chlorobutyryl chloride was used instead of methoxyacetyl chloride in Step 3 thereof, 750 mg of the titled compound was prepared.

$^1$H-NMR (400 MHz, CDCl$_3$) δ 8.42 (s, 1H), 8.17 (d, 1H), 7.547(s, 1H), 7.31 (s, 1H), 7.12 (m, 2H), 6.75 (m, 1H), 6.55 (d, 1H), 6.45 (s, 1H), 4.92 (m, 1H), 3.55 (d, 1H), 3.46 (d, 1H), 3.25 (t, 1H), 3.07 (d, 1H), 2.80-2.52 (m, 5H), 2.44 (m, 2H), 2.31 (m, 2H), 2.00 (m, 3H), 1.88-1.58 (m, 4H), 1.52-1.22 (m, 5H)

EXAMPLE 92

Preparation of 4-[N-[1-[N-(furan-2-ylcarbonyl)amino]cyclohexanecarbonyl]amino]-1-[4-fluoro-2-(3,3-dimethylazetidin-2-one-1-yl)phenyl]piperidin-3-one Step 1.

4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol In accordance with the same procedure as in Step 3 of Example 87, except that 3-chloropivaloyl chloride was used instead of methoxyacetyl chloride, 1.1 g of the titled compound was prepared.

Step 2.

4-[N-[1-[N-(furan-2-ylcarbonyl)amino]cyclohexanecarbonyl]amino]-1-[4-fluoro-2-(3,3-dimethylazetidin-2-one-1-yl)phenyl]piperidin-3-ol The solution of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol (1.1 g) obtained in Step 1 in 40 ml of dichloromethane was cooled to 0° C. and was added sodium tert-butoxide (NaOtBu, 600 mg) thereto. The reaction mixture was stirred overnight at room temperature, diluted with dichloromethane, and washed with brine. The resulting organic layer was dried and concentrated on sodium sulfate. The resulting residue was purified with column chromatography to give 762 mg of the titled compound.

Step 3.

4-[N-[1-[N-(furan-2-ylcarbonyl)amino]cyclohexanecarbonyl]amino]-1-[4-fluoro-2-(3,3-dimethylazetidin-2-one-1-yl)phenyl]piperidin-3-one To the solution of 4-[N-[1-[N-(furan-2-ylcarbonyl)amino]cyclohexane carbonyl]amino]-1-[4-fluoro-2-(3,3-dimethylazetidin-2-one-1-yl)phenyl]piperidin-3-ol (0.5 g) obtained in Step 2 in 10 ml of dimethylsulfoxide, was added 0.5 ml of triethylamine. The reaction mixture was cooled to 0° C. Pyridine-SO$_3$ complex (0.45 g) was added to the reaction mixture, which was then stirred for about 4 hours at room temperature. The reaction mixture was diluted with 20 ml of ethyl acetate and washed with brine. The resulting organic layer was dried and concentrated on sodium sulfate. The resulting residue was filtered and dried to give 340 mg of the titled compound.
$^1$H-NMR (400 MHz, CDCl$_3$) δ 7.81 (d, 1H), 7.50 (s, 2H), 7.15 (m, 2H), 6.88 (m, 1H), 6.54 (q, 1H), 6.45 (s, 1H), 6.63 (m, 1H), 3.78 (d, 1H), 3.67 (d, 1H), 3.55 (d, 1H), 3.27 (t, 1H), 3.19 (d, 1H), 2.78 (m, 1H), 2.26 (t, 2H), 1.97 (t, 2H), 1.73 (m, 4H), 1.48 (m, 2H), 1.36-1.21 (m, 7H)

EXAMPLE 93

Preparation of 4-[N-[1-[N-(furan-2-ylcarbonyl)amino]cyclohexanecarbonyl]amino]-1-[4-fluoro-2-(3-methylaziridin-2-one-1-yl)phenyl]piperidin-3-one In accordance with the same procedure as in Example 92, except that 2-chloropropionyl chloride was used instead of 3-chloropivaloyl chloride in Step 1 thereof, 750 mg of the titled compound was prepared.
$^1$H-NMR (400 MHz, CDCl$_3$) δ 9.69 (s, 1H), 8.60 (d, 1H), 7.49 (s, 2H), 7.14 (d, 2H), 6.81 (m, 1H), 6.54 (s, 1H), 6.48 (s, 1H), 4.67 (m, 1H), 4.54 (m, 1H), 3.65 (d, 1H), 3.59 (m, 1H), 3.44 (m, 1H), 2.76 (m, 1H), 2.21 (m, 2H), 1.95 (m, 2H), 1.81 (s, 3H), 1.71 (m, 4H), 1.44 (m, 2H), 1.36 (m, 1H)

EXAMPLE 94

Preparation of 4-[N-[1-[N-(furan-2-ylcarbonyl)amino]cyclohexanecarbonyl]amino]-1-[4-fluoro-2-(azetidin-2-one-1-yl)phenyl]piperidin-3-one In accordance with the same procedure as in Example 92, except that 3-chloropropionyl chloride was used instead of 3-chloropivaloyl chloride in Step 1 thereof, 750 mg of the titled compound was prepared.

$^1$H-NMR (400 MHz, CDCl$_3$) δ 8.44 (d, 1H), 8.32 (d, 1H), 7.52 (s, 2H), 7.14 (d, 2H), 6.81 (m, 1H), 6.54 (s, 1H), 6.48 (s, 1H), 4.60 (m, 1H), 3.65 (d, 1H), 3.59 (m, 1H), 3.44 (m, 1H), 3.00 (m, 2H), 2.76 (m, 1H), 2.21 (m, 2H), 2.01 (m, 2H), 1.95 (m, 2H), 1.71 (m, 4H), 1.44 (m, 2H), 1.36 (m, 1H)

EXAMPLE 95

Preparation of 4-[N-[1-[N-(furan-2-ylcarbonyl)amino]cyclohexanecarbonyl]amino]-1-[4-fluoro-2-(pyrrolidin-2-one-1-yl)phenyl]piperidin-3-one In accordance with the same procedure as in Example 92, except that 4-chlorobutyryl chloride was used instead of 3-chloropivaloyl chloride in Step 1 thereof, 230 mg of the titled compound was prepared.
$^1$H-NMR (400 MHz, CDCl$_3$) δ 7.49 (m, 1H), 7.26 (m, 2H), 7.03 (m, 3H), 6.53 (m, 1H), 6.43 (s, 1H), 4.64 (m, 1H), 3.80 (m, 1H), 3.70 (m, 1H), 3.55 (d, 1H), 3.47 (d, 1H), 3.23 (m, 2H), 2.57 (m, 1H), 2.55 (d, 2H), 2.26 (m, 2H), 2.15 (m, 2H), 1.96 (m, 3H), 1.59 (m, 2H), 1.48 (m, 1H)

EXAMPLE 96

Preparation of 4-[N-[1-[N-(furan-2-ylcarbonyl)amino]cyclohexanecarbonyl]amino]-1-[4-fluoro-2-(1,3-imidazolidin-2,5-dione-1-yl)phenyl]piperidin-3-one Step 1.

4-[N-[1-[N-(furan-2-ylcarbonyl)amino]cyclohexanecarbonyl]amino]-1-[4-fluoro-2-(ethoxycarbonylmethylcarbamoyl)aminophenyl]piperidin-3-ol In accordance with the same procedure as in Step 3 of Example 87, except that ethyl isocyanatoacetate was used instead of methoxyacetyl chloride, 400 mg of the titled compound was prepared.

Step 2.

4-[N-[1-[N-(furan-2-ylcarbonyl)amino]cyclohexanecarbonyl]amino]-1-[4-fluoro-2-(1,3-imidazolidin-2,5-dione-1-yl)aminophenyl]piperidin-3-ol To the solution of 4-[N-[1-[N-(furan-2-ylcarbonyl)amino]cyclohexane carbonyl]amino]-1-[4-fluoro-2-(ethoxycarbonylmethylcarbamoyl)aminophenyl]piperidin-3-ol (1.1 g) obtained in Step 1 in 10 ml of ethanol, was added 5 ml of hydrochloride solution. The reaction mixture was refluxed for about 6 hours, diluted with ethyl acetate (20 ml), and washed with brine. The resulting organic layer was dried and concentrated on sodium sulfate. The resulting residue was filtered and dried to give 140 mg of the titled compound as white color.

Step 3.

4-[N-[1-[N-(furan-2-ylcarbonyl)amino]cyclohexanecarbonyl]amino]-1-[4-fluoro-2-(1,3-imidazolidin-2,5-dione-1-yl)aminophenyl]piperidin-3-one To the solution of 4-[N-[1-[N-(furan-2-ylcarbonyl)amino]cyclohexane carbonyl]amino]-1-[4-fluoro-2-(1,3-imidazolidin-2,5-dione-1-yl)aminophenyl]piperidin-3-ol (140 mg) obtained in Step 2 in 10 ml of dimethylsulfoxide, was added 0.2 ml of triethylamine. The reaction mixture was cooled to 0° C. Pyridine-SO$_3$ complex (0.2 g) was added slowly to the reaction mixture, which was then stirred for about 4 hours at room temperature. The reaction mixture was diluted with 20 ml of ethyl acetate and washed with brine. The resulting organic layer was dried and concentrated on sodium sulfate. The resulting residue was filtered and dried to give 83 mg of the titled compound as white color.

$^1$H-NMR (400 MHz, CDCl$_3$) δ 7.96 (d, 1H), 7.85 (s, 1H), 7.66 (m, 1H), 7.55 (m, 1H), 7.53 (s, 2H), 7.13 (d, 1H), 6.99 (s, 1H), 6.61 (m, 1H), 6.59 (s, 1H), 6.43 (s, 1H), 4.78 (m, 1H), 4.26 (d, 2H), 4.01 (m, 2H), 3.83 (m, 2H), 3.11 (d, 1H), 2.98 (m, 1H), 2.76 (m, 1H), 2.21 (m, 2H), 1.95 (m, 2H), 1.71 (m, 4H), 1.44 (m, 2H), 1.36 (m, 1H)

EXAMPLE 97

Preparation of 4-[N-[1-[N-(furan-2-ylcarbonyl) amino]cyclohexanecarbonyl]amino]-1-[4-fluoro-2-(1,1-dioxo-isothiazolidin-1-yl)phenyl]piperidin-3-one In accordance with the same procedure as in Example 92, except that 3-chloropropanesulfonyl chloride was used instead of 3-chloropivaloyl chloride in Step 1 thereof, 80 mg of the titled compound was prepared.

$^1$H-NMR (400 MHz, CDCl$_3$) δ 8.27 (s, 1H), 8.18 (d, 1H), 7.62 (d, 1H), 7.50 (s, 1H), 7.15 (m, 2H), 6.76 (m, 1H), 6.55 (d, 1H), 6.46 (s, 1H), 4.62 (m, 1H), 3.56 (d, 1H), 3.45 (d, 1H), 3.23 (t, 1H), 3.00 (m, 1H), 2.78 (m, 1H), 2.27 (m, 4H), 1.98 (m, 2H), 1.73 (m, 6H), 1.48 (m, 2H), 1.38 (m, 1H)

EXAMPLE 98

Preparation of 4-[N-[1-[N-(furan-2-ylcarbonyl) amino]cyclohexanecarbonyl]amino]-1-[4-fluoro-2-(piperidin-2-one-1-yl)phenyl]piperidin-3-one In accordance with the same procedure as in Example 92, except that 5-chlorovaleryl chloride was used instead of 3-chloropivaloyl chloride in Step 1 thereof, 130 mg of the titled compound was prepared.

$^1$H-NMR (400 MHz, CDCl$_3$) δ 7.50 (s, 2H), 7.29 (m, 2H), 7.00 (m, 1H), 6.92 (d, 1H), 6.54 (d, 1H), 6.47 (s, 1H), 4.63 (m, 1H), 3.67 (m, 2H), 3.52-3.27 (m, 4H), 2.96 (s, 1H), 2.88 (s, 1H), 2.55 (m, 2H), 2.26 (m, 2H), 2.00 (m, 2H), 1.98-1.75 (m, 6H), 1.66 (m, 4H), 1.44-1.25 (m, 4H)

EXAMPLE 99

Preparation of 4-[N-[1-[N-(furan-2-ylcarbonyl) amino]cyclohexanecarbonyl]amino]-1-[4-fluoro-2-(pyrrol-1-yl)phenyl]piperidin-3-one Step 1.

4-[N-[1-[N-(furan-2-ylcarbonyl)amino]cyclohexanecarbonyl]amino]-1-[4-fluoro-2-(pyrrol-1-yl)phenyl]piperidin-3-ol The mixture of 4-[N-[1-[N-(furan-2-ylcarbonyl)amino] cyclohexanecarbonyl]amino]-1-(4-fluoro-2-aminophenyl) piperidin-3-ol (3.0 g) obtained in Step 2 of Example 87 and 2,5-dimethoxytetrahydrofuran (0.96 ml) was refluxed in 80 ml of acetic acid for 1 hour. The reaction mixture was concentrated under reduced pressure. The resulting residue was diluted with 70 ml of dichloromethane and washed with a saturated sodium bicarbonate and brine. The resulting organic layer was dried and concentrated on sodium sulfate. The resulting residue was purified with column chromatography to give 1.8 g of the titled compound as white color.

$^1$H-NMR (400 MHz, CDCl$_3$) δ 7.50 (s, 2H), 7.29 (m, 2H), 7.00 (m, 1H), 6.92 (d, 1H), 6.54 (d, 1H), 6.47 (s, 1H), 6.26 (s, 2H), 4.00 (broad, 1H), 3.71 (m, 2H), 3.51 (m, 1H), 3.19 (d, 1H), 2.78 (s, 1H), 2.55 (m, 2H), 2.26 (m, 2H), 2.00 (m, 2H), 1.98-1.75 (m, 6H), 1.66 (m, 4H), 1.44-1.25 (m, 4H)

Step 2.

4-[N-[1-[N-(furan-2-ylcarbonyl)amino]cyclohexanecarbonyl]amino]-1-[4-fluoro-2-(pyrrol-1-yl)phenyl] piperidin-3-one To the solution of 4-[N-[1-[N-(furan-2-ylcarbonyl)amino] cyclohexane carbonyl]amino]-1-[4-fluoro-2-(pyrrol-1-yl) phenyl]piperidin-3-ol (1.8 g) obtained in Step 1 in 10 ml of dimethylsulfoxide, was added 2 ml of triethylamine. The reaction mixture was cooled to 0° C. Pyridine-SO$_3$ complex (1.8 g) was added to the reaction mixture, which was then stirred for about 2 hours at room temperature. The reaction mixture was diluted with 50 ml of ethyl acetate and washed with brine. The resulting organic layer was dried and concentrated on sodium sulfate. The resulting residue was filtered and dried to give 1.5 g of the titled compound as white color.

$^1$H-NMR (400 MHz, CDCl$_3$) δ 7.48 (s, 1H), 7.38 (d, 1H), 7.14 (d, 1H), 6.95 (m, 5H), 6.41 (d, 1H), 6.38 (s, 1H), 6.29 (q, 2H), 4.57 (m, 1H), 3.43 (s, 2H), 2.93-2.85 (m, 2H), 2.51 (m, 1H), 2.23 (d, 2H), 1.95 (t, 2H), 1.76-1.53 (m, 4H), 1.52-1.22 (m, 3H)

EXAMPLE 100

Preparation of 4-[N-[1-[N-(furan-2-ylcarbonyl) amino]cyclohexanecarbonyl]amino]-1-[4-fluoro-2-(oxazol-4-yl)phenyl]piperidin-3-one Step 1.

4-[N-[1-[N-(furan-2-ylcarbonyl)amino]cyclohexanecarbonyl]amino]-1-[4-fluoro-2-(oxazol-4-yl)phenyl]piperidin-3-ol The mixture of 4-[N-[1-[N-(furan-2-ylcarbonyl)amino] cyclohexanecarbonyl]amino]-1-(4-fluoro-2-formylhenyl)piperidin-3-ol (3.0 g, 6 mmol) obtained in Example 79, potassium carbonate (2 g, 20 mmol) and p-toluenesulfonylmethyl isocyanate (TosMIC; 1.8 g, 9 mmol) was refluxed in 500 ml of methanol for about 2 hours. The reaction mixture was concentrated, added water thereto, and extracted with dichloromethane. The resulting organic layer was dried and concentrated on sodium sulfate. The resulting residue was purified with column chromatography to give 3.2 g of the titled compound.

Step 2.

4-[N-[1-[N-(furan-2-ylcarbonyl)amino]cyclohexanecarbonyl]amino]-1-[4-fluoro-2-(oxazol-4-yl)phenyl]piperidin-3-ol To the solution of 4-[N-[1-[N-(furan-2-ylcarbonyl)amino] cyclohexanecarbonyl]amino]-1-[4-fluoro-2-(oxazol-4-yl) phenyl]piperidin-3-ol (1.8 g) obtained in Step 1 in 20 ml of dimethylsulfoxide, was added 2.7 ml of triethylamine (19 mmol). The reaction mixture was cooled to 0° C. Pyridine-SO₃ complex (3.04 g, 19 mmol) was added to the reaction mixture, which was then stirred for about 2 hours at room temperature. The reaction mixture was diluted with 100 ml of ethyl acetate and washed with brine. The resulting organic layer was dried and concentrated on sodium sulfate. The resulting residue was purified with column chromatography to give 1.67 g of the titled compound.

$^1$H-NMR (400 MHz, CDCl₃) δ 7.91 (s, 1H), 7.65 (s, 1H), 7.48 (m, 3H), 7.22 (m, 2H), 7.00 (m, 1H), 6.54 (d, 2H), 4.67 (m, 1H), 3.56 (s, 2H), 3.22 (m, 2H), 2.78 (m, 1H), 2.29 (d, 2H), 1.98 (m, 2H), 1.84-1.62 (m, 5H), 1.43-1.19 (m, 3H)

EXAMPLE 101

Preparation of 4-[N-[1-[N-(furan-2-ylcarbonyl) amino]cyclohexanecarbonyl]amino]-1-[4-fluoro-2-(N-methylcarbamoyl)phenyl]piperidin-3-one Step 1.

4-[N-[1-[N-(furan-2-ylcarbonyl)amino]cyclohexanecarbonyl]amino]-1-[4-fluoro-2-(N-methylcarbamoyl)phenyl]piperidin-3-ol To the solution of 4-[N-[1-[N-(furan-2-ylcarbonyl)amino] cyclohexanecarbonyl]amino]-1-(4-fluoro-2-formylhenyl)piperidin-3-ol (4.0 g, 6 mmol) obtained in Example 79 and potassium bicarbonate (NaH₃PO₄; 340 mg) in the mixed solvent of 20 ml of acetonitrile and 6 ml of distilled water, was 35%-hydrogen peroxide solution (1.0 ml) and sodium hypochlorite (NaClO₄; 1.2 g) at 10° C. The reaction mixture was stirred for about 1 hour at room temperature, added sodium sulfite (1.0 g) thereto, and acidified with 10%-hydrochloride solution. The resulting solid was filtered and dried to give 3.6 g of a solid. The resulting solid (2.5 g), monomethylamine hydrochloride (1.0 g) and benzotriazole-1-yloxytripyrrolidinophosphonium hexaphosphate (PyBOP; 800 mg) were dissolved in 30 ml of dichloromethane (MC; 30 ml), cooled to 0° C. Diisopropylethylamine (DIEA; 1.0 g) was added to the reaction mixture, which was then stirred for about 4 hours. Water was added to the reaction mixture. The resulting organic layer was dried and concentrated on sodium sulfate. The resulting residue was purified with column chromatography to give 1.5 g of the titled compound.

$^1$H-NMR (400 MHz, CDCl₃) δ 10.25 (broad, 1H), 7.89 (d, 1H), 7.51 (s, 1H), 7.22-7.16 (m, 4H), 6.56 (m, 2H), 4.15 (m, 2H), 3.91-3.79 (m, 2H), 3.35 (d, 1H), 3.21 (d, 1H), 2.98 (s, 3H), 2.76 (m, 2H), 2.23 (m, 2H), 2.00 (m, 4H), 1.70 (m, 4H), 1.40-1.20 (m, 3H)

Step 2.

4-[N-[1-[N-(furan-2-ylcarbonyl)amino]cyclohexanecarbonyl]amino]-1-[4-fluoro-2-(N-methylcarbamoyl)phenyl]piperidin-3-ol To the solution of 4-[N-[1-[N-(furan-2-ylcarbonyl)amino] cyclohexane carbonyl]amino]-1-[4-fluoro-2-(N-methylcarbamoyl)phenyl]piperidin-3-ol (1.8 g) obtained in Step 1 in 10 ml of dimethyl sulfoxide, was added 2 ml of triethylamine. The reaction mixture was cooled to 0° C. Pyridine-SO₃ complex (1.8 g) was added slowly to the reaction mixture, which was then stirred for about 2 hours at room temperature. The reaction mixture was diluted with 50 ml of ethyl acetate and washed with brine. The resulting organic layer was dried and concentrated on sodium sulfate. The resulting residue was purified with column chromatography to give 1.2 g of the titled compound.

$^1$H-NMR (400 MHz, CDCl₃) δ 8.86 (d, 1H), 7.85 (d, 1H), 7.62 (d, 1H), 7.50 (s, 1H), 7.16 (m, 3H), 6.55 (d, 1H), 6.46 (s, 1H), 4.56 (d, 1H), 3.62 (s, 2H), 3.26 (d, 2H), 2.97 (s, 3H), 2.78 (m, 1H), 2.68 (s, 1H), 2.27(m, 2H), 1.70 (t, 3H), 1.43-1.21 (m, 3H)

EXAMPLE 102

Preparation of 4-[N-[1-[N-(furan-2-ylcarbonyl) amino]cyclohexanecarbonyl]amino]-1-[2-(N,N-dimethylcarbamoyl)phenyl]piperidin-3-one In accordance with the same procedure as in Example 101, except that dimethylamine was used instead of monomethylamine hydrochloride in Step 1 thereof, 1.05 g of the titled compound was prepared.

$^1$H-NMR (400 MHz, CDCl₃) δ 7.49 (m, 2H), 7.13 (s, 1H), 6.99 (m, 3H), 6.54 (q, 1H), 6.43 (s, 1H), 4.61 (m, 1H), 3.73 (m, 1H), 3.53 (m, 2H), 3.07 (s, 3H), 2.75 (s, 3H), 2.58 (broad, 1H), 2.24 (m, 2H), 1.96 (m, 2H), 1.72 (m, 4H), 1.47-1.24 (m, 3H)

EXAMPLE 103

Preparation of 4-[N-[1-[N-(furan-2-ylcarbonyl) amino]cyclohexanecarbonyl]amino]-1-[2-(N-cyclopropylcarbamoyl)phenyl]piperidin-3-one In accordance with the same procedure as in Example 101, except that cyclopropylamine was used instead of monomethylamine hydrochloride in Step 1 thereof, 240 mg of the titled compound was prepared.

$^1$H-NMR (400 MHz, CDCl₃) δ 9.11 (s, 1H), 7.88 (d, 1H), 7.62 (d, 1H), 7.50 (d, 1H), 7.13 (m, 3H), 6.55 (d, 1H), 6.47 (s, 1H), 4.67 (m, 1H), 3.58 (m, 2H), 3.26 (m, 2H), 2.99 (m, 1H), 2.87 (m, 1H), 2.78 (m, 1H), 2.25 (m, 2H), 1.99 (m, 2H), 1.50 (m, 4H), 1.42-1.23 (m, 3H), 0.88 (m, 2H), 0.55 (m, 2H)

EXAMPLE 104

Preparation of 4-[N-[1-[N-(5-methyl-isoxazol-3-ylcarbonyl)amino]cyclohexanecarbonyl]amino]-1-(2-aminophenyl)piperidin-3-one Step 1.

4-[N-[1-[N-(5-methyl-isoxazol-3-ylcarbonyl)amino] cyclohexanecarbonyl]amino]-1-(2-aminophenyl) piperidin-3-ol In accordance with the same procedure as in Step 2 of Example 87, except that 4-[N-[1-[N-(5-methyl-isoxazol-3-ylcarbonyl)amino]cyclohexanecarbonyl]amino]-1-(4-fluoro-2-nitrophenyl)piperidin-3-ol was used instead of 4-[N-[1-[N-(furan-2-ylcarbonyl)amino]cyclohexanecarbonyl]amino]-1-(4-fluoro-2-nitrophenyl)piperidin-3-ol, 1.1 g of the titled compound was prepared.

Step 2.

4-[N-[1-[N-(5-methyl-isoxazol-3-ylcarbonyl)amino]
cyclohexanecarbonyl]amino]-1-(2-aminophenyl)
piperidin-3-one To the solution of 4-[N-[1-[N-(5-methyl-isoxazol-3-ylcarbonyl)amino]cyclohexanecarbonyl]amino]-1-(2-aminophenyl)piperidin-3-ol (1.1 g) obtained in Step 1 in 5 ml of dimethyl sulfoxide, was added 1.2 ml of triethylamine. The reaction mixture was cooled to 0° C. Pyridine-SO$_3$ complex (0.9 g) was added to the reaction mixture, which was then stirred for about 4 hours at room temperature. The reaction mixture was diluted with 20 ml of ethyl acetate and washed with brine. The resulting organic layer was dried and concentrated on sodium sulfate. The resulting residue was filtered and dried to give 820 mg of the titled compound as white color.
$^1$H-NMR (400 MHz, CDCl$_3$) δ 7.11 (m, 1H), 6.88 (m, 1H), 6.56 (d, 1H), 6.48 (s, 1H), 6.34 (m, 1H), 6.21 (s, 1H), 4.59 (s, 1H), 4.22 (m, 1H), 3.16 (m, 4H), 2.80 (d, 1H), 2.52 (s, 3H), 2.23 (d, 1H), 2.00-1.78 (m, 4H), 1.68 (m, 2H), 1.42-1.21 (m, 3H)

EXAMPLE 105

Preparation of 4-[N-[1-[N-(5-methyl-isoxazol-3-ylcarbonyl)amino]cyclohexanecarbonyl]amino]-1-(2-nitrophenyl)piperidin-3-one In accordance with the same procedure as in Example 76, except that 1-[N-(5-methyl-isoxazol-3-ylcarbonyl)amino]cyclohexanecarboxylic acid was used instead of 1-[N-(furan-2-ylcarbonyl)amino]cyclohexanecarboxylic acid in Step 3 thereof, and 1-fluoronitrobenzene was used instead of 1-fluorophenyl methyl sulfone in Step 5 thereof, 330 mg of the titled compound was prepared.
$^1$H-NMR (400 MHz, CDCl$_3$) δ 8.10 (d, 1H), 7.66 (t, 1H), 7.42 (m, 2H), 7.32 (d, 1H), 6.93 (s, 1H), 6.44 (s, 1H), 4.70 (m, 1H), 3.86, (q, 3H), 3.41 (t, 1H), 2.78 (m, 1H), 2.50 (s, 3H), 2.31 (broad, 2H), 2.00 (m, 3H), 1.75 (m, 2H), 1.52 (m, 2H), 1.38 (m, 1H)

EXAMPLE 106

Preparation of 4-[N-[1-[N-(5-methyl-isoxazol-3-ylcarbonyl)amino]cyclohexanecarbonyl]amino]-1-(2-methanesulfonylphenyl)piperidin-3-one In accordance with the same procedure as in Example 76, except that 1-[N-(5-methyl-isoxazol-3-ylcarbonyl)amino]cyclohexanecarboxylic acid was used instead of 1-[N-(furan-2-ylcarbonyl)amino]cyclohexanecarboxylic acid in Step 3 thereof, 870 mg of the titled compound was prepared.
$^1$H-NMR (400 MHz, CDCl$_3$) δ 8.10 (d, 1H), 7.66 (t, 1H), 7.42 (m, 2H), 7.32 (d, 1H), 6.93 (s, 1H), 6.44 (s, 1H), 4.71 (m, 1H), 3.78 (d, 1H), 3.65 (d, 1H), 3.51 (d, 1H), 3.18 (s, 3H), 2.69 (m, 1H), 2.50 (s, 3H), 2.20 (t, 2H), 1.98 (m, 3H), 1.60 (m, 2H), 1.47 (m, 2H), 1.38(m, 1H)

EXAMPLE 107

Preparation of 4-[N-[1-[N-(5-methyl-isoxazol-3-ylcarbonyl)amino]cyclohexanecarbonyl]amino]-1-(2-ethanesulfonylphenyl)piperidin-3-one In accordance with the same procedure as in Example 76, except that 1-[N-(5-methyl-isoxazol-3-ylcarbonyl)amino] cyclohexanecarboxylic acid was used instead of 1-[N-(furan-2-ylcarbonyl)amino]cyclohexanecarboxylic acid in Step 3 thereof, and 1-fluorophenyl ethyl sulfone was used instead of 1-fluorophenyl methyl sulfone in Step 5 thereof, 330 mg of the titled compound was prepared.
$^1$H-NMR (400 MHz, CDCl$_3$) δ 8.07 (d, 1H), 7.65 (t, 1H), 7.39 (m, 2H), 7.31 (d, 1H), 6.93 (s, 1H), 6.44 (s, 1H), 4.70 (m, 1H), 3.77 (d, 1H), 3.61 (d, 1H), 3.57 (d, 1H), 3.39 (m, 2H), 3.11 (t, 1H), 2.78 (m, 1H), 2.50 (s, 3H), 2.24 (t, 2H), 2.00 (t, 2H), 1.89 (m, 1H), 1.70 (m, 2H), 1.47 (m, 2H), 1.31 (m, 1H), 1.10 (t, 3H)

EXAMPLE 108

Preparation of 4-[N-[1-[N-(5-methyl-isoxazol-3-ylcarbonyl)amino]cyclohexanecarbonyl]amino]-1-[4-fluoro-2-(3,3-dimethyl-azetidin-2-one-1-yl)phenyl]piperidin-3-one In accordance with the same procedure as in Example 92, except that 4-[N-[1-[N-(5-methyl-isoxazol-3-ylcarbonyl)amino]cyclohexanecarbonyl]amino]-1-[4-fluoro-2-(3-chloro-2,2-dimethylpropionyl)aminophenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 240 mg of the titled compound was prepared.
$^1$H-NMR (400 MHz, CDCl$_3$) δ7.80 (d, 1H), 7.34 (d, 1H), 7.10 (m, 1H), 6.95 (s, 1H), 6.80 (m, 1H), 6.43 (s, 1H), 4.63 (m, 1H), 3.67 (d, 1H), 3.55 (m, 2H), 3.50 (d, 1H), 3.43 (t, 1H), 3.21 (d, 1H), 2.78 (m, 1H), 2.50 (s, 3H), 2.24 (t, 2H), 1.96 (t, 2H), 1.74-1.69 (m, 4H), 1.43-1.20 (m, 10H)

EXAMPLE 109

Preparation of 4-[N-[1-[N-(5-methyl-isoxazol-3-ylcarbonyl)amino]cyclohexanecarbonyl]amino]-1-[4-fluoro-2-(pyrrolidin-2-one-1-yl)phenyl]piperidin-3-one In accordance with the same procedure as in Example 92, except that 4-[N-[1-[N-(5-methyl-isoxazol-3-ylcarbonyl)amino]cyclohexanecarbonyl]amino]-1-[4-fluoro-2-(4-chlorobutyryl)aminophenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 130 mg of the titled compound was prepared.
$^1$H-NMR (400 MHz, CDCl$_3$) δ 7.34 (d, 1H), 7.09-6.90 (m, 4H), 6.43 (s, 1H), 4.62 (m, 1H), 3.81 (m, 1H), 3.70 (m, 1H), 3.55 (q, 2H), 3.23 (m, 2H), 2.78 (m, 1H), 2.62-2.50 (m, 7H), 2.23 (m, 5H), 1.94 (t, 2H), 1.70-1.58 (m, 4H), 1.40-1.21 (m, 3H)

EXAMPLE 110

Preparation of 4-[N-[1-[N-(5-methyl-isoxazol-3-ylcarbonyl)amino]cyclohexanecarbonyl]amino]-1-[4-fluoro-2-(oxazolidin-2-one-3-yl)phenyl]piperidin-3-one In accordance with the same procedure as in Example 92, except that 4-[N-[1-[N-(5-methyl-isoxazol-3-ylcarbonyl)amino]cyclohexanecarbonyl]amino]-1-[4-fluoro-2-(2-chloro-ethoxycarbonyl)aminophenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 130 mg of the titled compound was prepared.

$^1$H-NMR (400 MHz, CDCl$_3$) δ 7.06 (s, 1H), 6.88 (q, 1H), 6.54 (d, 1H), 6.47 (s, 1H), 6.32 (t, 1H), 6.20 (d, 1H), 5.62 (s, 1H), 4.53 (s, 1H), 4.22 (m, 1H), 3.16 (m, 3H), 2.84 (d, 1H), 2.52 (s, 3H), 2.23 (d, 2H), 2.11-1.83 (m, 3H), 1.64-1.52 (m, 4H), 1.48-1.27 (m, 6H)

EXAMPLE 111

Preparation of 4-[N-[1-[N-(5-methyl-isoxazol-3-ylcarbonyl)amino]cyclohexanecarbonyl]amino]-1-[4-fluoro-2-(imidazolidin-2-one-1-yl)phenyl]piperidin-3-one In accordance with the same procedure as in Example 92, except that 4-[N-[1-[N-(5-methyl-isoxazol-3-ylcarbonyl)amino]cyclohexanecarbonyl]amino]-1-[4-fluoro-2-(2-chloroethylcarbamoylamino)phenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 79 mg of the titled compound was prepared.

$^1$H-NMR (400 MHz, CDCl$_3$) δ 7.14 (d, 1H), 7.03-6.91 (m, 3H), 6.43 (s, 1H), 4.69 (m, 1H), 3.93-3.51 (m, 8H), 3.43 (m, 1H), 3.21 (t, 1H), 2.78 (m, 1H), 2.50 (s, 3H), 2.23 (m, 2H), 1.96 (m, 2H), 1.73 (m, 2H), 1.46-1.26 (m, 3H)

EXAMPLE 112

Preparation of 4-[N-[1-[N-(5-methyl-isoxazol-3-ylcarbonyl)amino]cyclohexanecarbonyl]amino]-1-[2-(3,3-dimethyl-azetidin-2-one-1-yl)phenyl]piperidin-3-one In accordance with the same procedure as in Example 92, except that 4-[N-[1-[N-(5-methyl-isoxazol-3-ylcarbonyl)amino]cyclohexanecarbonyl]amino]-1-[2-(3-chloro-2,2-dimethylpropionyl)aminophenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 373 mg of the titled compound was prepared.

$^1$H-NMR (400 MHz, CDCl$_3$) δ 9.62 (s, 1H), 7.87 (f, 1H), 7.11 (q, 3H), 6.87 (m, 2H), 6.41 (s, 1H), 4.98 (m, 1H), 4.11 (m, 2H), 3.69 (m, 2H), 3.31 (d, 1H), 3.14 (d, 1H), 2.78 (m, 1H), 2.50 (s, 3H), 2.17 (m, 3H), 1.88 (q, 2H), 1.67 (m, 5H), 1.45-1.26 (m, 12H)

EXAMPLE 113

Preparation of 4-[N-[1-[N-(5-methyl-isoxazol-3-ylcarbonyl)amino]cyclohexanecarbonyl]amino]-1-[2-(pyrrolidin-2-one-1-yl)phenyl]piperidin-3-one In accordance with the same procedure as in Example 92, except that 4-[N-[1-[N-(5-methyl-isoxazol-3-ylcarbonyl)amino]cyclohexanecarbonyl]amino]-1-[2-(4-chlorobutyrylamino)phenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 373 mg of the titled compound was prepared.

$^1$H-NMR (400 MHz, CDCl$_3$) δ 7.33 (m, 3H), 7.15 (m, 2H), 6.94 (s, 1H), 6.43 (s, 1H), 4.65 (m, 1H), 3.80 (m, 1H), 3.66 (m, 2H), 3.55 (d, 1H), 3.41 (d, 1H), 3.23 (t, 1H), 2.78 (m, 1H), 2.54 (m, 2H), 2.50 (s, 1H), 2.23 (m, 6H), 1.96 (t, 2H), 1.66 (m, 4H), 1.45-1.21 (m, 3H)

EXAMPLE 114

Preparation of 4-[N-[1-[N-(5-chloro-thiophen-2-ylcarbonyl)amino]cyclohexanecarbonyl]amino]-1-(2-methanesulfonylphenyl)piperidin-3-one In accordance with the same procedure as in Example 76, except that 1-[N-(5-chloro-thiophen-2-ylcarbonyl)amino]cyclohexanecarboxylic acid was used instead of 1-[N-(furan-2-ylcarbonyl)amino]cyclohexanecarboxylic acid in Step 3 thereof, 1.1 g of the titled compound was prepared.

$^1$H-NMR (400 MHz, CDCl$_3$) δ 8.08 (d, 1H), 7.65 (t, 1H), 7.45 (m, 3H), 7.32 (d, 1H), 6.92 (d, 1H), 5.95 (s, 1H), 4.67 (m, 1H), 3.77 (d, 1H), 3.65 (d, 1H), 3.55 (m, 1H), 3.19 (m, 1H), 3.18 (s, 3H), 2.69 (m, 1H), 2.24 (d, 2H), 2.00 (m, 3H), 1.65 (m, 3H), 1.45 (m, 3H)

EXAMPLE 115

Preparation of 4-[N-[1-[N-(5-chloro-thiophen-2-ylcarbonyl)amino]cyclohexanecarbonyl]amino]-1-(2-ethanesulfonylphenyl)piperidin-3-one In accordance with the same procedure as in Example 76, except that 1-[N-(5-chloro-thiophen-2-ylcarbonyl)amino]cyclohexanecarboxylic acid was used instead of 1-[N-(furan-2-ylcarbonyl)amino]cyclohexanecarboxylic acid in Step 3 thereof, and 1-fluorophenyl ethyl sulfone was used instead of 1-fluorophenyl methyl sulfone in Step 5 thereof, 450 mg of the titled compound was prepared.

$^1$H-NMR (400 MHz, CDCl$_3$) δ 8.06 (d, 1H), 7.65 (t, 1H), 7.45 (m, 4H), 6.92 (d, 1H), 5.96 (d, 1H), 4.66 (m, 1H), 3.77 (d, 1H), 3.63 (d, 1H), 3.53 (m, 1H), 3.32 (m, 2H), 3.17 (m, 1H), 2.69 (m, 1H), 2.23 (d, 2H), 1.97 (m, 3H), 1.65 (m, 3H), 1.45 (m, 3H), 1.12 (t, 3H)

EXAMPLE 116

Preparation of 4-[N-[1-[N-(5-chloro-thiophen-2-ylcarbonyl)amino]cyclohexanecarbonyl]amino]-1-(2-isopropanesulfonylphenyl)piperidin-3-one In accordance with the same procedure as in Example 76, except that 1-[N-(5-chloro-thiophen-2-ylcarbonyl)amino]cyclohexanecarboxylic acid was used instead of 1-[N-(furan-2-ylcarbonyl)amino]cyclohexanecarboxylic acid in Step 3 thereof, and 1-fluorophenyl isopropane sulfone was used instead of 1-fluorophenyl methyl sulfone in Step 5 thereof, 560 mg of the titled compound was prepared.

$^1$H-NMR (400 MHz, CDCl$_3$) δ 8.05 (d, 1H), 7.65 (t, 1H), 7.45 (m, 3H), 7.32 (d, 1H), 6.92 (d, 1H), 5.99 (s, 1H), 4.66 (m, 1H), 3.79 (m, 1H), 3.77 (d, 1H), 3.59 (d, 1H), 3.53 (m, 1H), 3.14 (m, 1H), 2.69 (m, 1H), 2.24 (d, 2H), 1.89 (m, 3H), 1.70 (m, 3H), 1.43 (m, 3H), 1.30 (d, 3H), 1.08 (d, 3H)

EXAMPLE 117

Preparation of 4-[N-[1-[N-(5-chloro-thiophen-2-ylcarbonyl)amino]cyclohexanecarbonyl]amino]-1-(5-fluoro-2-methanesulfonylphenyl)piperidin-3-one In accordance with the same procedure as in Example 76, except that 1-[N-(5-chloro-thiophen-2-ylcarbonyl)amino]

cyclohexanecarboxylic acid was used instead of 1-[N-(furan-2-ylcarbonyl)amino]cyclohexanecarboxylic acid in Step 3 thereof, and 2,4-difluorophenyl methane sulfone was used instead of 1-fluorophenyl methyl sulfone in Step 5 thereof, 210 mg of the titled compound was prepared.

$^1$H-NMR (400 MHz, CDCl$_3$) δ7.80 (m, 1H), 7.35 (m, 5H), 6.93 (d, 1H), 5.93(s, 1H), 4.66 (m, 1H), 3.77 (d, 1H), 3.65 (d, 1H), 3.52 (m, 1H), 3.19 (s, 3H), 3.18 (m, 1H), 2.69 (m, 1H), 2.24 (d, 2H), 2.00 (m, 3H), 1.70 (m, 3H), 1.42 (m, 3H)

EXAMPLE 118

Preparation of 4-[N-[1-[N-(5-methyl-thiophen-2-ylcarbonyl)amino]cyclohexanecarbonyl]amino]-1-(2-methanesulfonylphenyl)piperidin-3-one In accordance with the same procedure as in Example 76, except that 1-[N-(5-methyl-thiophen-2-ylcarbonyl)amino] cyclohexanecarboxylic acid was used instead of 1-[N-(furan-2-ylcarbonyl)amino]cyclohexanecarboxylic acid in Step 3 thereof, 562 mg of the titled compound was prepared.

$^1$H-NMR (400 MHz, CDCl$_3$) δ 8.08 (d, 1H), 7.60 (m, 2H), 7.40 (m, 4H), 6.76 (d, 1H), 6.01 (s, 1H), 4.68 (m, 1H), 3.77 (d, 1H), 3.65 (d, 1H), 3.55 (m, 1H), 3.19 (m, 1H), 3.18 (s, 3H), 2.69 (m, 1H), 2.52 (s, 3H), 2.24 (d, 2H), 1.95 (m, 3H), 1.70 (m, 3H), 1.45 (m, 3H)

EXAMPLE 119

Preparation of 4-[N-[1-[N-(5-methyl-thiophen-2-ylcarbonyl)amino]cyclohexanecarbonyl]amino]-1-(2-isopropanesulfonylphenyl)piperidin-3-one In accordance with the same procedure as in Example 76, except that 1-[N-(5-methyl-thiophen-2-ylcarbonyl)amino] cyclohexanecarboxylic acid was used instead of 1-[N-(furan-2-ylcarbonyl)amino]cyclohexanecarboxylic acid in Step 3 thereof, and 1-fluorophenyl isopropane sulfone was used instead of 1-fluorophenyl methyl sulfone in Step 5 thereof, 110 mg of the titled compound was prepared.

$^1$H-NMR (400 MHz, CDCl$_3$) δ 8.21 (m, 1H), 7.55 (m, 2H), 7.33 (m, 3H), 6.79 (d, 1H), 5.92 (s, 1H), 4.66 (m, 1H), 3.79 (m, 1H), 3.77 (d, 1H), 3.59 (d, 1H), 3.53 (m, 1H), 3.17 (m, 1H), 2.69 (m, 1H), 2.53 (s, 3H), 2.24 (m, 2H), 1.89 (m, 3H), 1.70 (m, 3H), 1.43 (m, 3H), 1.30 (d, 3H), 1.08 (d, 3H)

EXAMPLE 120

Preparation of 4-[N-[1-[N-(5-methyl-thiophen-2-ylcarbonyl)amino]cyclohexanecarbonyl]amino]-1-(5-fluoro-2-methanesulfonylphenyl)piperidin-3-one In accordance with the same procedure as in Example 76, except that 1-[N-(5-methyl-thiophen-2-ylcarbonyl)amino] cyclohexanecarboxylic acid was used instead of 1-[N-(furan-2-ylcarbonyl)amino]cyclohexanecarboxylic acid in Step 3 thereof, and 2,4-difluorophenyl methane sulfone was used instead of 1-fluorophenyl methyl sulfone in Step 5 thereof, 222 mg of the titled compound was prepared.

$^1$H-NMR (400 MHz, CDCl$_3$) δ 7.55 (m, 1H), 7.45 (m, 1H), 7.35 (m, 3H), 7.15 (m, 1H), 6.75 (d, 1H), 5.95 (s, 1H), 4.68 (m, 1H), 3.75 (d, 1H), 3.63 (d, 1H), 3.52 (m, 1H), 3.19 (s, 3H), 3.18 (m, 1H), 2.69 (m, 1H), 2.52 (s, 3H), 2.24 (d, 2H), 1.95 (m, 3H), 1.70 (m, 3H), 1.42 (m, 3H)

EXAMPLE 121

Preparation of 4-[N-[1-[N-(3-methyl-thiophen-2-ylcarbonyl)amino]cyclohexanecarbonyl]amino]-1-(2-methanesulfonylphenyl)piperidin-3-one In accordance with the same procedure as in Example 76, except that 1-[N-(3-methyl-thiophen-2-ylcarbonyl)amino] cyclohexanecarboxylic acid was used instead of 1-[N-(furan-2-ylcarbonyl)amino]cyclohexanecarboxylic acid in Step 3 thereof, 131 mg of the titled compound was prepared.

$^1$H-NMR (400 MHz, CDCl$_3$) δ 8.09 (d, 1H), 7.66 (m, 1H), 7.54 (d, 1H), 7.42 (m, 2H), 7.31 (d, 1H), 6.91 (d, 1H), 5.95 (s, 1H), 4.70 (m, 1H), 3.80 (d, 1H), 3.63 (d, 1H), 3.41 (m, 1H), 3.29 (td, 1H), 3.18 (s, 3H), 2.78 (m, 1H), 2.55 (s, 3H), 2.27 (m, 2H), 1.95-1.82 (m, 3H), 1.72 (m, 2H), 1.48 (m, 2H), 1.32 (m, 1H)

EXAMPLE 122

Preparation of 4-[N-[1-[N-(2-methyl-furan-3-ylcarbonyl)amino]cyclohexanecarbonyl]amino]-1-(2-methanesulfonylphenyl)piperidin-3-one In accordance with the same procedure as in Example 76, except that 1-[N-(2-methyl-furan-3-ylcarbonyl)amino]cyclohexanecarboxylic acid was used instead of 1-[N-(furan-2-ylcarbonyl)amino]cyclohexanecarboxylic acid in Step 3 thereof, 180 mg of the titled compound was prepared.

$^1$H-NMR (400 MHz, CDCl$_3$) δ 8.09 (d, 1H), 7.66 (q, 1H), 7.54 (d, 1H), 7.42 (m, 2H), 7.31 (d, 1H), 6.92 (d, 1H), 5.94 (s, 1H), 4.70 (m, 1H), 3.80 (d, 1H), 3.63 (d, 1H), 3.41 (m, 1H), 3.29 (td, 1H), 3.18 (s, 3H), 2.78 (m, 1H), 2.55 (s, 3H), 2.27 (m, 2H), 1.95-1.82 (m, 3H), 1.72 (m, 2H), 1.48 (m, 2H), 1.32 (m, 1H)

EXAMPLE 123

Preparation of 4-[N-[1-[N-(5-methyl-furan-2-ylcarbonyl)amino]cyclohexanecarbonyl]amino]-1-(2-methanesulfonylphenyl)piperidin-3-one In accordance with the same procedure as in Example 76, except that 1-[N-(5-methyl-furan-2-ylcarbonyl)amino]cyclohexanecarboxylic acid was used instead of 1-[N-(furan-2-ylcarbonyl)amino]cyclohexanecarboxylic acid in Step 3 thereof, 123 mg of the titled compound was prepared.

$^1$H-NMR (400 MHz, CDCl$_3$) δ 8.09 (d, 1H), 7.64 (m, 1H), 7.54 (d, 1H), 7.42 (m, 2H), 7.04 (d, 1H), 6.34 (s, 1H), 6.13 (d, 1H), 4.70 (m, 1H), 3.80 (d, 1H), 3.63 (d, 1H), 3.41 (m, 1H), 3.29 (dt, 1H), 3.18 (s, 3H), 2.78 (m, 1H), 2.40 (s, 3H), 2.27 (m, 2H), 1.95-1.82 (m, 3H), 1.72 (m, 2H), 1.48 (m, 2H), 1.32 (m, 1H)

EXAMPLE 124

Preparation of 4-[N-[1-[N-(5-bromo-furan-2-ylcarbonyl)amino]cyclohexanecarbonyl]amino]-1-(2-methanesulfonyl-4-methoxyphenyl)piperidin-3-one In accordance with the same procedure as in Example 76, except that 1-[N-(5-methyl-furan-2-ylcarbonyl)amino]cyclohexanecarboxylic acid was used instead of 1-[N-(furan-2-ylcarbonyl)amino]cyclohexanecarboxylic acid in Step 3 thereof, and 2-fluoro-5-methoxyphenyl methane sulfone was used instead of 1-fluorophenyl methyl sulfone in Step 5 thereof, 254 mg of the titled compound was prepared.

¹H-NMR (400 MHz, CDCl₃) δ7.8 (m, 1H), 7.48 (m, 1H), 7.38 (m, 2H), 7.10 (s, 1H), 6.48 (s, 1H), 6.38 (s, 1H), 4.63 (s, 1H), 3.21 (s, 3H), 2.18-1.31 (m, 12H)

EXAMPLE 125

Preparation of 4-[N-[1-[N-(4,5-dimethyl-furan-2-ylcarbonyl)amino]cyclohexanecarbonyl]amino]-1-(2-methanesulfonylphenyl)piperidin-3-one In accordance with the same procedure as in Example 76, except that 1-[N-(4,5-dimethyl-furan-2-ylcarbonyl)amino]cyclohexanecarboxylic acid was used instead of 1-[N-(furan-2-ylcarbonyl)amino]cyclohexanecarboxylic acid in Step 3 thereof, 270 mg of the titled compound was prepared.

¹H-NMR (400 MHz, CDCl₃) δ 8.09 (d, 1H), 7.66 (m, 1H), 7.54 (d, 1H), 7.42 (m, 2H), 6.92 (s, 1H), 6.32 (s, 1H), 4.70 (m, 1H), 3.80 (d, 1H), 3.63 (d, 1H), 3.41 (m, 1H), 3.29 (td, 1H), 3.18 (s, 3H), 2.78 (m, 1H), 2.55 (s, 3H), 2.29 (s, 3H), 2.27 (m, 2H), 2.01 (s, 3H), 1.95-1.82 (m, 3H), 1.72 (m, 2H), 1.48 (m, 2H), 1.32 (m, 1H)

EXAMPLE 126

Preparation of 4-[N-[1-[N-(4,5-dimethyl-furan-2-ylcarbonyl)amino]cyclohexanecarbonyl]amino]-1-[2-(pyrrolidin-2-one-1-yl)phenyl]piperidin-3-one In accordance with the same procedure as in Example 92, except that 4-[N-[1-[N-(4,5-dimethyl-furan-2-ylcarbonyl)amino]cyclohexanecarbonyl]amino]-1-[2-(4-chlorobutyryl)aminophenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 440 mg of the titled compound was prepared.

¹H-NMR (400 MHz, CDCl₃) δ 7.23 (m, 2H), 7.09 (m, 2H), 6.91 (s, 1H), 4.65 (m, 1H), 3.71 (m, 1H), 3.62 (m, 2H), 3.51 (m, 2H), 3.33 (d, 1H), 3.21 (t, 1H), 2.69 (m, 1H), 2.54 (m, 2H), 2.28 (d, 3H), 2.22 (m, 2H), 1.95 (s, 3H), 1.75 (m, 4H), 1.43-1.21 (m, 3H)

EXAMPLE 127

Preparation of 4-[N-[1-[N-(morpholin-4-ylcarbonyl)amino]cyclohexanecarbonyl]amino]-1-(2-methanesulfonylphenyl)piperidin-3-one In accordance with the same procedure as in Example 76, except that 1-[N-(morpholin-4-ylcarbonyl)amino]cyclohexanecarboxylic acid was used instead of 1-[N-(furan-2-ylcarbonyl)amino]cyclohexanecarboxylic acid in Step 3 thereof, 80 mg of the titled compound was prepared.

¹H-NMR (400 MHz, CDCl₃) δ 8.1(m, 1H), 7.6(m, 1H), 7.3(m, 2H), 6.8(d, 1H), 6.4(s, 1H), 4.7(m, 1H), 3.7(dd, 2H), 3.1(s, 3H), 1.4-2.0(m, 10H)

EXAMPLE 128

Preparation of 4-[N-[1-[N-(benzothiophen-2-ylcarbonyl)amino]cyclohexanecarbonyl]amino]-1-(2-methanesulfonylphenyl)piperidin-3-one In accordance with the same procedure as in Example 76, except that 1-[N-(benzothiophen-2-ylcarbonyl)amino]cyclohexanecarboxylic acid was used instead of 1-[N-(furan-2-ylcarbonyl)amino]cyclohexanecarboxylic acid in Step 3 thereof, 250 mg of the titled compound was prepared.

¹H-NMR (400 MHz, CDCl₃) δ 8.07 (d, 1H), 7.87 (m, 3H), 7.65 (m, 1H), 7.45-7.39 (m, 5H), 6.25 (s, 1H), 4.70 (m, 1H), 3.80 (d, 1H), 3.63 (d, 1H), 3.41 (m, 1H), 3.29 (td, 1H), 3.18 (s, 3H), 2.78 (m, 1H), 2.27 (m, 2H), 1.95-1.82 (m, 3H), 1.72 (m, 2H), 1.48 (m, 2H), 1.32 (m, 1H),

EXAMPLE 129

Preparation of 4-[N-[1-[N-(benzothiophen-2-ylcarbonyl)amino]cyclohexanecarbonyl]amino]-1-(2-tert-butoxycarbonylphenyl)piperidin-3-one In accordance with the same procedure as in Example 85, except that 4-[N-[1-[N-(benzothiophen-2-ylcarbonyl)amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride and 2-tert-butyl bromobenzoate was used instead of 1-bromo-4-fluoro-2-thiomethoxybenzene in Step 1 thereof, 110 mg of the titled compound was prepared.

¹H-NMR (400 MHz, CDCl₃) δ 7.84 (m, 2H), 7.74 (s, 1H), 7.51 (d, 1H), 7.49 (d, 1H), 7.43 (f, 1H), 7.32 (dd, 1H), 6.94 (m, 2H), 6.23 (s, 1H), 4.66 (m, 1H), 3.80 (d, 1H), 3.63 (d, 1H), 3.41 (m, 1H), 3.29 (td, 1H), 2.78 (m, 1H), 2.27 (m, 2H), 1.95-1.82 (m, 3H), 1.72 (m, 2H), 1.55 (s, 9H), 1.48 (m, 2H), 1.32 (m, 1H)

EXAMPLE 130

Preparation of 4-[N-[1-[N-(benzothiophen-2-ylcarbonyl)amino]cyclohexanecarbonyl]amino]-1-(2-chloro-5-trifluoromethylphenyl)piperidin-3-one In accordance with the same procedure as in Example 85, except that 4-[N-[1-[N-(benzothiophen-2-ylcarbonyl)amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride and 1-bromo-2-chloro-5-trifluoromethylbenzene was used instead of 1-bromo-4-fluoro-2-thiomethoxybenzene in Step 1 thereof, 222 mg of the titled compound was prepared ¹H-NMR (400 MHz, CDCl₃) δ 7.86 (m, 3H), 7.46 (m, 3H), 7.23 (m, 2H), 6.20 (s, 1H), 4.72 (m, 1H), 3.83 (d, 1H), 3.79 (d, 1H), 3.62 (d, 1H), 3.25 (t, 1H), 2.78 (m, 1H), 2.27 (m, 2H), 2.01 (t, 2H), 1.82-1.61 (m, 4H), 1.20 (m, 2H), 1.18 (m, 1H)

EXAMPLE 131

Preparation of 4-[N-[1-[N-(benzothiophen-2-ylcarbonyl)amino]cyclohexanecarbonyl]amino]-1-(4-chloro-2-fluoro-phenyl)piperidin-3-one In accordance with the same procedure as in Example 85, except that 4-[N-[1-[N-(benzothiophen-2-ylcarbonyl)amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride and 1-bromo-2-fluoro-4-chlorobenzene was used instead of 1-bromo-4-fluoro-2-thiomethoxybenzene in Step 1 thereof, 76 mg of the titled compound was prepared ¹H-NMR (400 MHz, CDCl₃) δ 7.86 (m, 3H), 7.42 (m, 3H), 7.06 (m, 2H), 6.83 (d, 1H), 6.24 (s, 1H), 4.67 (m, 1H), 3.82 (d, 1H), 3.78 (d, 1H), 3.62 (d, 1H), 3.27 (t, 1H), 2.78 (m, 1H), 2.27 (m, 2H), 2.01 (t, 2H), 1.82-1.61 (m, 4H), 1.20 (m, 2H), 1.18 (m, 1H)

EXAMPLE 132

Preparation of 4-[N-[1-[N-(benzothiophen-2-ylcarbonyl)amino]cyclohexanecarbonyl]amino]-1-(2-methylphenyl)piperidin-3-one In accordance with the same procedure as in Example 85, except that 4-[N-[1-[N-(benzothiophen-2-ylcarbonyl)amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride and 1-bromo-2-chloro-5-trifluoromethylbenzene was used instead of 1-bromotoluene in Step 1 thereof, 123 mg of the titled compound was prepared.

$^1$H-NMR (400 MHz, CDCl$_3$) δ 7.87 (m, 3H), 7.45 (m, 3H), 7.17 (m, 2H), 7.00 (m, 2H), 6.20 (s, 1H), 4.69 (m, 1H), 3.58 (m, 2H), 3.17 (m, 2H), 2.30 (m, 2H), 2.25 (s, 3H), 2.01 (t, 2H), 1.73 (m, 4H), 1.47-1.37 (m, 3H)

EXAMPLE 133

Preparation of 4-[N-[1-[N-(3-methyl-benzofuran-2-ylcarbonyl)amino]cyclohexanecarbonyl]amino]-1-(2-methanesulfonylphenyl)piperidin-3-one In accordance with the same procedure as in Example 76, except that 1-[N-(3-methyl-benzofuran-2-ylcarbonyl)amino]cyclohexanecarboxylic acid was used instead of 1-[N-(furan-2-ylcarbonyl)amino]cyclohexanecarboxylic acid in Step 3 thereof, 250 mg of the titled compound was prepared.

$^1$H-NMR (400 MHz, CDCl$_3$) δ 8.09 (d, 1H), 7.64 (m, 2H), 7.51-7.32 (m, 6H), 6.73 (s, 1H), 4.70 (m, 1H), 3.78 (d, 1H), 3.63 (d, 1H), 3.41 (m, 1H), 3.29 (td, 1H), 3.17 (s, 3H), 2.78 (m, 1H), 2.61 (s, 3H), 2.27 (m, 2H), 1.95-1.82 (m, 3H), 1.72 (m, 2H), 1.48 (m, 2H), 1.32 (m, 1H)

EXAMPLE 134

Preparation of 4-[N-[1-[N-(3-methyl-benzofuran-2-ylcarbonyl)amino]cyclohexanecarbonyl]amino]-1-(5-fluoro-2-trifluoromethylphenyl)piperidin-3-one In accordance with the same procedure as in Example 85, except that 4-[N-[1-[N-(3-methyl-benzofuran-2-ylcarbonyl)amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride and 1-bromo-2-trifluoromethyl-5-fluorobenzene was used instead of 1-bromotoluene in Step 1 thereof, 128 mg of the titled compound was prepared.

$^1$H-NMR (400 MHz, CDCl$_3$) δ 7.63 (d, 1H), 7.48-7.31 (m, 7H), 6.75 (s, 1H), 4.68 (m, 1H), 3.58 (d, 1H), 3.48 (d, 1H), 3.46 (d, 1H), 3.23 (m, 2H), 2.75 (m, 1H), 2.61 (s, 3H), 2.33(d, 2H), 2.04-1.97 (t, 2H), 1.81-1.72 (m, 4H), 1.52 (m, 2H), 1.21 (m, 1H)

EXAMPLE 135

Preparation of 4-[N-[1-[N-(3-methyl-benzofuran-2-ylcarbonyl)amino]cyclohexanecarbonyl]amino]-1-(5-cyano-2-methoxyphenyl)piperidin-3-one In accordance with the same procedure as in Example 85, except that 4-[N-[1-[N-(3-methyl-benzofuran-2-ylcarbonyl) amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride and 3-bromo-4-methoxybenzonitrile was used instead of 1-bromotoluene in Step 1 thereof, 270 mg of the titled compound was prepared.

$^1$H-NMR (400 MHz, CDCl$_3$) δ 7.63 (d, 1H), 7.50 (m, 3H), 7.33-7.29 (m, 2H), 7.11 (s, 1H), 6.88 (d, 1H), 6.74 (s, 1H), 4.71 (m, 1H), 3.89 (s, 3H), 3.84 (d, 1H), 3.59 (d, 1H), 3.51 (m, 1H), 3.24 (t, 1H), 2.78 (m, H), 2.61 (s, 3H), 2.30 (m, 2H), 2.03 (t, 2H), 1.82-1.61 (m, 4H), 1.20 (m, 2H), 1.18 (m, 1H)

EXAMPLE 136

Preparation of 4-[N-[1-[N-(quinolin-2-ylcarbonyl)amino]cyclohexanecarbonyl]amino]-1-(2-methanesulfonylphenyl)piperidin-3-one In accordance with the same procedure as in Example 76, except that 1-[N-(quinolin-2-ylcarbonyl)amino]cyclohexanecarboxylic acid was used instead of 1-[N-(furan-2-ylcarbonyl)amino]cyclohexanecarboxylic acid in Step 3 thereof, 310 mg of the titled compound was prepared.

$^1$H-NMR (400 MHz, CDCl$_3$) δ 8.64 (s, 1H), 8.36 (d, 1H), 8.30 (d, 1H), 8.17 (d, 1H), 8.06 (d, 1H), 7.91 (d, 1H), 7.81 (d, 1H), 7.67 (d, 1H), 7.42 (m, 1H, 7.68 (m, 3H), 7.40 (m, 2H), 7.32 (s, 1H), 4.74 (m, 1H), 3.78 (d, 1H), 3.63 (d, 1H), 3.60 (d, 1H), 3.22 (d, 1H), 3.16 (s, 3H), 2.62 (m, 1H), 2.40 (t, 2H), 2.02 (t, 2H), 1.91 (m, 1H), 1.78 (m, 3H), 1.55 (q, 2H), 1.26 (m, 1H)

EXAMPLE 137

Preparation of 4-[N-[1-[N-(quinolin-2-ylcarbonyl)amino]cyclohexanecarbonyl]amino]-1-[2-(pyrrolidin-2-one-1-yl)phenyl]piperidin-3-one In accordance with the same procedure as in Example 92, except that 4-[N-[1-[N-(quinolin-2-ylcarbonyl)amino]cyclohexanecarbonyl]amino]-1-[2-(4-chlorobutyryl)aminophenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl)aminophenyl]piperidin-3-ol in Step 2 thereof, 900 mg of the titled compound was prepared.

$^1$H-NMR (400 MHz, CDCl$_3$) δ 8.65 (s, 1H), 8.36 (d, 1H), 8.30 (s, 1H), 8.19 (d, 1H), 7.92 (d, 1H), 7.82 (m, 1H), 7.66 (m, 1H), 7.58 (m, 1H), 7.24 (m, 2H), 7.10 (m, 2H), 4.65 (m, 1H), 3.69 (m, 1H), 3,61 (m, 1H), 3.55 (d, 1H), 3.51 (d, 1H), 3.30 (d, H), 3.21 (t, 1H), 2.84 (m, 2H), 2.51 (m, 2H), 2.33 (m, 2H), 1.74 (m, 4H), 1.28 (m, 2H)

EXAMPLE 138

Preparation of 4-[N-[1-[N-(quinolin-2-ylcarbonyl)amino]cyclohexanecarbonyl]amino]-1-(2-nitrophenyl)piperidin-3-one In accordance with the same procedure as in Example 76, except that 1-[N-(quinolin-2-ylcarbonyl)amino]cyclohexanecarboxylic acid was used instead of 1-[N-(furan-2-ylcarbonyl)amino]cyclohexanecarboxylic acid in Step 3 thereof, and except that 1-fluoro-2-nitrobenzene was used instead of 1-fluorophenyl methane sulfone in Step 5 thereof, 1.7 g of the titled compound was prepared.

$^1$H-NMR (400 MHz, CDCl$_3$) δ 8.62 (s, 1H), 8.32 (d, 1H), 8.28 (d, 1H), 8.16 (d, 1H), 7.88 (d, 1H), 7.80-7.74 (m, 2H), 7.59 (t, 1H), 7.49 (d, 1H), 7.14-1.09 (m, 2H), 4.70 (m, 1H), 3.73 (s, 2H), 3.37 (m, 2H), 2.86 (m, 1H), 2.31 (m, 2H), 2.02 (m, 2H), 1.91 (m, 1H), 1.75 (m, 2H), 1.54 (f, 2H), 1.40 (m, 1H)

EXAMPLE 139

Preparation of 4-[N-[1-[N-(pyrazin-2-ylcarbonyl) amino]cyclohexanecarbonyl]amino]-1-(2-methanesulfonylphenyl)piperidin-3-one In accordance with the same procedure as in Example 76, except that 1-[N-(pyrazin-2-ylcarbonyl)amino]cyclohexanecarboxylic acid was used instead of 1-[N-(furan-2-ylcarbonyl)amino]cyclohexanecarboxylic acid in Step 3 thereof, 340 mg of the titled compound was prepared.

$^1$H-NMR (400 MHz, CDCl$_3$) δ 7.8 (m, 1H), 7.3-7.1 (m, 4H), 4.7 (m, 1H), 3.7 (dd, 2H), 3.2 (s, 3H), 1.3-2.1 (m, 10H)

EXAMPLE 140

Preparation of 4-[N-[1-[N-(pyrazin-2-ylcarbonyl) amino]cyclohexanecarbonyl]amino]-1-(2-methanesulfonylphenyl)piperidin-3-one dihydrochloride 50 ml of saturated hydrogenchloride-ethyl acetate solution was added to 4-[N-[1-[N-(pyrazin-2-ylcarbonyl)amino]cyclohexanecarbonyl]amino]-1-(2-methanesulfonylphenyl)piperidin-3-one (500 mg) obtained in Example 139. The reaction mixture was stirred for 2 hours at room temperature and filtered to give 380 mg of the titled compound as white solid.

$^1$H-NMR (400 MHz, CDCl$_3$) δ 9.87 (broad, 1H), 7.8 (m, 1H), 7.3-7.1 (m, 4H), 4.7 (m, 1H), 3.7 (dd, 2H), 3.2 (s, 3H), 1.3-2.1 (m, 10H)

EXAMPLE 141

Preparation of 4-[N-[1-[N-(isonicotinylcarbonyl) amino]cyclohexanecarbonyl]amino]-1-(2-methanesulfonylphenyl)piperidin-3-one In accordance with the same procedure as in Example 76, except that 1-[N-(isonicotinylcarbonyl)amino]cyclohexanecarboxylic acid was used instead of 1-[N-(furan-2-ylcarbonyl)amino]cyclohexanecarboxylic acid in Step 3 thereof, 430 mg of the titled compound was prepared.

$^1$H-NMR (400 MHz, CDCl$_3$) δ 8.8 (d, 2H), 7.8 (d, 2H), 7.2-7.4 (m, 3H), 6.3 (s, 1H), 4.7 (m, 1H), 3.7 (dd, 2H), 3.2 (s, 3H), 1.3-2.1 (m, 10H)

EXAMPLE 142

Preparation of 4-[N-[1-[N-(6-chloronicotinylcarbonyl)amino]cyclohexanecarbonyl]amino]-1-(2-methanesulfonylphenyl)piperidin-3-one In accordance with the same procedure as in Example 76, except that 1-[N-(6-chloronicotinylcarbonyl)amino]cyclohexanecarboxylic acid was used instead of 1-[N-(furan-2-ylcarbonyl)amino]cyclohexanecarboxylic acid in Step 3 thereof, 122 mg of the titled compound was prepared.

$^1$H-NMR (400 MHz, CDCl$_3$) δ 8.63 (d, 1H), 8.09-7.95 (m, 2H), 7.66 (t, 1H), 7.42 (d, 1H), 7.40 (m, 2H), 6.82 (d, 1H), 6.16 (s, 1H), 4.71 (m, 1H), 3.80 (d, 1H), 3.63 (d, 1H), 3.41 (m, 1H), 3.29 (td, 1H), 3.17 (s, 3H), 2.78 (m, 1H), 2.27 (m, 2H), 1.95-1.82 (m, 3H), 1.72 (m, 2H), 1.48 (m, 2H), 1.32 (m, 1H)

EXAMPLE 143

Preparation of 4-[N-[1-[N-(6-chloronicotinylcarbonyl)amino]cyclohexanecarbonyl]amino]-1-(4-fluoro-2-nitrophenyl)piperidin-3-one In accordance with the same procedure as in Example 76, except that 1-[N-(6-chloronicotinylcarbonyl)amino]cyclohexanecarboxylic acid was used instead of 1-[N-(furan-2-ylcarbonyl)amino]cyclohexanecarboxylic acid in Step 3 thereof, and except that 1-fluoronitrobenzene was used instead of 1-fluorophenyl methane sulfone in Step 5 thereof, 255 mg of the titled compound was prepared.

$^1$H-NMR (400 MHz, CDCl$_3$) δ 8.62 (s, 1H), 7.99 (m, 1H), 7.53 (m, 2H), 7.21 (m, 2H), 6.77 (d, 1H), 6.27 (s, 1H), 4.71 (m, 1H), 3.98 (m, 3H), 3.69 (s, 2H), 3.34 (m, 2H), 2.78 (m, 1H), 2.23 (d, 2H), 1.97 (m, 4H), 1.70 (m, 4H), 1.45-1.21 (m, 3H)

EXAMPLE 144

Preparation of 4-[N-[1-[N-(pyridin-2-ylcarbonyl) amino]cyclohexanecarbonyl]amino]-1-(2-methanesulfonylphenyl)piperidin-3-one In accordance with the same procedure as in Example 76, except that 1-[N-(pyridin-2-ylcarbonyl)amino]cyclohexanecarboxylic acid was used instead of 1-[N-(furan-2-ylcarbonyl)amino]cyclohexanecarboxylic acid in Step 3 thereof, 1.0 g of the titled compound was prepared.

$^1$H-NMR (400 MHz, CDCl$_3$) δ 8.6 (m, 2H), 8.4 (s, 1H), 8.1-8.2 (m, 3H), 7.8 (m, 1H), 7.2-7.6 (m, 3H), 4.7 (m, 1H), 3.6 (dd, 2H), 3.2 (s, 3H), 1.3-2.1 (m, 10H)

EXAMPLE 145

Preparation of 4-[N-[1-[N-(pyridin-2-ylcarbonyl) amino]cyclohexanecarbonyl]amino]-1-(2-methanesulfonylphenyl)piperidin-3-one hydrochloride 50 ml of saturated hydrogenchloride-ethyl acetate solution was added to 4-[N-[1-[N-(pyridin-2-ylcarbonyl)amino]cyclohexanecarbonyl]amino]-1-(2-methanesulfonylphenyl)piperidin-3-one (500 mg) obtained in Example 144. The reaction mixture was stirred for 2 hours at room temperature and filtered to give 410 mg of the titled compound as white solid.

$^1$H-NMR (400 MHz, CDCl$_3$) δ 9.32 (broad, 1H), 8.6 (m, 2H), 8.4 (s, 1H), 8.1-8.2 (m, 3H), 7.8 (m, 1H), 7.2-7.6 (m, 3H), 4.7 (m, 1H), 3.6 (dd, 2H), 3.2 (s, 3H), 1.3-2.1 (m, 10H)

EXAMPLE 146

Preparation of 4-[N-[1-[N-(4-fluorobenzoyl)amino] cyclohexanecarbonyl]amino]-1-(2-methanesulfonylphenyl)piperidin-3-one In accordance with the same procedure as in Example 76, except that 1-[N-(4-fluorobenzoyl)amino]cyclohexanecarboxylic acid was used instead of 1-[N-(furan-2-ylcarbonyl) amino]cyclohexanecarboxylic acid in Step 3 thereof, 653 mg of the titled compound was prepared.

$^1$H-NMR (400 MHz, CDCl$_3$) δ 7.8 (m, 2H), 7.6 (m, 1H), 7.4 (m, 2H), 6.1 (s, 1H), 4.7 (m, 1H), 3.7 (dd, 2H), 3.2 (s, 3H), 2.3 (m, 2H), 1.3-2.1 (m, 10H)

EXAMPLE 147

Preparation of 4-[N-[1-[N-(4-fluorobenzoyl)amino] cyclohexanecarbonyl]amino]-1-(4-fluoro-2-methanesulfonylphenyl)piperidin-3-one In accordance with the same procedure as in Example 76, except that 1-[N-(4-fluorobenzoyl)amino]cyclohexanecarboxylic acid was used instead of 1-[N-(furan-2-ylcarbonyl) amino]cyclohexanecarboxylic acid in Step 3 thereof, and 2,5-difluorophenyl methyl sulfone was used instead of 1-fluorophenyl methane sulfone in Step 5 thereof, 680 mg of the titled compound was prepared.
$^1$H-NMR (400 MHz, CDCl$_3$) δ 8.2 (m, 1H), 7.81 (m, 3H), 7.61 (m, 1H), 7.41 (m, 1H), 7.24 (m, 1H), 7.15 (m, 1H), 6.15 (s, 1H), 4.63 (s, 1H), 3.21 (s, 3H), 2.1-1.31(m, 12H)

EXAMPLE 148

Preparation of 4-[N-[1-[N-(4-fluorobenzoyl)amino] cyclohexanecarbonyl]amino]-1-(2-methanesulfonyl-4-methoxyphenyl)piperidin-3-one In accordance with the same procedure as in Example 76, except that 1-[N-(4-fluorobenzoyl)amino]cyclohexanecarboxylic acid was used instead of 1-[N-(furan-2-ylcarbonyl) amino]cyclohexanecarboxylic acid in Step 3 thereof, and 2-fluoro-5-methoxyphenyl methyl sulfone was used instead of 1-fluorophenyl methane sulfone in Step 5 thereof, 885 mg of the titled compound was prepared.
$^1$H-NMR (400 MHz, CDCl$_3$) δ 8.1 (m, 1H), 7.78 (m, 2H), 7.5 (m, 1H), 7.38 (m 1H), 7.20 (m, 1H), 7.15 (m, 1H), 6.2 (s, 1H), 4.62 (s, 1H), 3.82 (s, 3H), 3.21 (s, 3H), 2.1-1.31 (m, 12H)

EXAMPLE 149

Preparation of 4-[N-[1-[N-(4-fluorobenzoyl)amino] cyclohexanecarbonyl]amino]-1-(4-fluoro-2-trifluoromethylphenyl)piperidin-3-one In accordance with the same procedure as in Example 85, except that 4-[N-[1-[N-(4-fluorobenzoyl)amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride and 1-bromo-4-fluoro-2-trifluoromethylbenzene was used instead of 1-bromo-4-fluoro-2-thiomethoxybenzene in Step 1 thereof, 137 mg of the titled compound was prepared.
$^1$H-NMR (400 MHz, CDCl$_3$) δ 8.1 (m, 1H), 7.78 (m, 2H), 7.5 (m, 1H), 7.38 (m, 1H), 7.20 (m, 1H), 7.15-6.90 (m, 3H), 6.2 (s, 1H), 4.62 (s, 1H), 2.1-1.31 (m, 12H)

EXAMPLE 150

Preparation of 4-[N-[1-[N-(4-fluorobenzoyl)amino] cyclohexanecarbonyl]amino]-1-[2-(3-phenylpropionylamino)phenyl]piperidin-3-one In accordance with the same procedure as in Example 87, except that 4-[N-[1-[N-(4-fluorobenzoyl)amino]cyclohexanecarbonyl]amino]-1-(4-fluoro-2-aminophenyl)piperidin-3-ol was used instead of 4-[N-[1-[N-(furan-2-ylcarbonyl) amino]cyclohexanecarbonyl]amino]-1-(4-fluoro-2-aminophenyl)piperidin-3-ol and hydrocinnamoyl chloride was used instead of methoxyacetyl chloride in Step 3 thereof, 671 mg of the titled compound was prepared.
$^1$H-NMR (400 MHz, CDCl$_3$) δ 8.1 (m, 1H), 7.78 (m, 2H), 7.5 (m, 1H), 7.38 (m, 1H), 7.20 (m, 1H), 7.15-6.90 (m, 8H), 6.2 (s, 1H), 4.62 (s, 1H), 2.83 (m, 2H), 2.44 (m, 2H), 2.19 (m, 2H), 2.1-1.31 (m, 12H)

EXAMPLE 151

Preparation of 4-[N-[1-[N-(4-fluorobenzoyl)amino] cyclohexanecarbonyl]amino]-1-[2-(cyclopropylamino)phenyl]piperidin-3-one In accordance with the same procedure as in Example 87, except that 4-[N-[1-[N-(4-fluorobenzoyl)amino]cyclohexanecarbonyl]amino]-1-(4-fluoro-2-aminophenyl)piperidin-3-ol was used instead of 4-[N-[1-[N-(furan-2-ylcarbonyl) amino]cyclohexanecarbonyl]amino]-1-(4-fluoro-2-aminophenyl)piperidin-3-ol and cyclopropylcarbonyl chloride was used instead of methoxyacetyl chloride in Step 3 thereof, 1.5 g of the titled compound was prepared.
$^1$H-NMR (400 MHz, CDCl$_3$) δ 8.1 (m, 1H), 7.78 (m, 2H), 7.5 (m, 1H), 7.38 (m, 1H), 7.20 (m, 1H), 7.15-6.90 (m, 3H), 6.2 (s, 1H), 4.62 (s, 1H), 2.1-1.31 (m, 12H), 0.48 (m, 4H)

EXAMPLE 152

Preparation of 4-[N-[1-[N-(4-fluorobenzoyl)amino] cyclohexanecarbonyl]amino]-1-[4-fluoro-2-(2,3,4-trifluorobenzoylamino)phenyl]piperidin-3-one In accordance with the same procedure as in Example 87, except that 4-[N-[1-[N-(4-fluorobenzoyl)amino]cyclohexanecarbonyl]amino]-1-(4-fluoro-2-aminophenyl)piperidin-3-ol was used instead of 4-[N-[1-[N-(furan-2-ylcarbonyl) amino]cyclohexanecarbonyl]amino]-1-(4-fluoro-2-aminophenyl)piperidin-3-ol and 2,3,4-trifluorobenzoyl chloride was used instead of methoxyacetyl chloride in Step 3 thereof, 321 mg of the titled compound was prepared.
$^1$H-NMR (400 MHz, CDCl$_3$) δ 8.1 (m, 1H), 7.78 (m, 2H), 7.5 (m, 1H), 7.38 (m, 1H), 7.20 (m, 1H), 7.15-6.90 (m, 3H), 6.2 (s, 1H), 4.62 (s, 1H), 2.1-1.31 (m, 12H)

EXAMPLE 153

Preparation of 4-[N-[1-[N-(4-biphenylcarbonyl) amino]cyclohexanecarbonyl]amino]-1-(2-methanesulfonylphenyl)piperidin-3-one In accordance with the same procedure as in Example 76, except that 1-[N-(4-biphenylcarbonyl)amino]cyclohexanecarboxylic acid was used instead of 1-[N-(furan-2-ylcarbonyl)amino]cyclohexanecarboxylic acid in Step 3 thereof, 653 mg of the titled compound was prepared.
$^1$H-NMR (400 MHz, CDCl$_3$) δ 8.11 (d, 1H), 7.90 (d, 2H), 7.66 (m, 5H), 7.38 (m, 5H), 4.71 (m, 1H), 3.78 (d, 1H), 3.75 (d, 1H), 3.64 (d, 1H), 3.56(d, 1H), 3.19 (s, 3H), 2.78 (s, 3H), 2.15 (m, 2H), 1.89 (m, 3H), 1.66 (m, 4H), 1.38-1.26 (m, 3H)

EXAMPLE 154

Preparation of 4-[N-[1-[N-(4-trifluoromethylbenzoyl)amino]cyclohexanecarbonyl]amino]-1-(2-methanesulfonylphenyl)piperidin-3-one In accordance with the same procedure as in Example 76, except that 1-[N-(4-trifluoromethylbenzoyl)amino]cyclohexanecarboxylic acid was used instead of 1-[N-(furan-2- ylcarbonyl)amino]cyclohexanecarboxylic acid in Step 3 thereof, 432 mg of the titled compound was prepared.
$^1$H-NMR (400 MHz, CDCl$_3$) δ 8.10 (d, 1H), 8.07 (d, 2H), 7.87 (d, 1H), 7.68 (d, 1H), 7.48 (d, 1H), 7.38 (m, 2H), 7.29 (m, 2H), 6.20 (s, 1H), 4.71 (m, 1H), 3.78 (d, 1H), 3.64 (d, 1H), 3.20 (s, 3H), 2.78 (m, 1H), 2.05 (m, 2H), 1.87 (m, 3H), 1.62 (m, 5H), 1.16 (m, 3H)

EXAMPLE 155

Preparation of 4-[N-[1-[N-(4-(2-morpholinethoxy) benzoyl)amino]cyclohexanecarbonyl]amino]-1-(2-methanesulfonylphenyl)piperidin-3-one In accordance with the same procedure as in Example 76, except that 1-[N-(4-(2-morpholinethoxy)amino)cyclohexanecarboxylic acid was used instead of 1-[N-(furan-2-ylcarbonyl)amino]cyclohexanecarboxylic acid in Step 3 thereof, 543 mg of the titled compound was prepared.
$^1$H-NMR (400 MHz, CDCl$_3$) δ 8.05 (d, 1H), 7.8 (d, 2H), 7.68-7.24 (m, 4H), 6.68 (d, 2H), 4.89 (m, 1H), 4.08 (m, 4H), 3.75 (t, 2H), 3.15 (s, 3H), 2.18-1.15 (m, 12H)

EXAMPLE 156

Preparation of 4-[N-[1-[N-(4-(2-pyrrolidinethoxy) benzoyl)amino]cyclohexanecarbonyl]amino]-1-(2-methanesulfonylphenyl)piperidin-3-one In accordance with the same procedure as in Example 76, except that 1-[N-(4-(2-pyrrolidinethoxy)benzoyl)amino]cyclohexanecarboxylic acid was used instead of 1-[N-(furan-2-ylcarbonyl)amino]cyclohexanecarboxylic acid in Step 3 thereof, 543 mg of the titled compound was prepared.
$^1$H-NMR (400 MHz, CDCl$_3$) δ 8.05 (d, 1H), 7.8 (d, 2H), 7.68-7.24 (m, 4H), 6.68 (d, 2H), 4.69 (m, 1H), 4.08 (m, 4H), 3.82 (dd, 2H), 3.15 (s, 3H), 2.18-1.15 (m, 12H)

EXAMPLE 157

Preparation of 4-[N-[1-[N-(4-(2-piperidinethoxy) benzoyl)amino]cyclohexanecarbonyl]amino]-1-(2-methanesulfonylphenyl)piperidin-3-one In accordance with the same procedure as in Example 76, except that 1-[N-(4-(2-piperidinethoxy)benzoyl)amino]cyclohexanecarboxylic acid was used instead of 1-[N-(furan-2-ylcarbonyl)amino]cyclohexanecarboxylic acid in Step 3 thereof, 543 mg of the titled compound was prepared.
$^1$H-NMR (400 MHz, CDCl$_3$) δ 8.05 (d, 1H), 7.8 (d, 2H), 7.68-7.24 (m, 4H), 6.68 (d, 2H), 4.69 (m, 1H), 4.08 (m, 4H), 3.82 (dd, 2H), 3.15 (s, 3H), 2.8 (m, 2H), 2.18-1.15 (m, 12H)

EXAMPLE 158

Preparation of 4-[N-[1-[N-(4-(2-morpholinethoxy) benzoyl)amino]cyclohexanecarbonyl]amino]-1-(2-methanesulfonylphenyl)piperidin-3-one hydrochloride 50 ml of saturated hydrogenchloride-ethyl acetate solution was added to 4-[N-[1-[N-(4-(2-morpholinethoxy)benzoyl)amino]cyclohexanecarbonyl]amino]-1-(2-methanesulfonylphenyl)piperidin-3-one (500 mg) obtained in Example 155. The reaction mixture was stirred for 2 hours at room temperature and filtered to give 420 ml of the titled compound as white solid.
$^1$H-NMR (400 MHz, CDCl$_3$) δ8.05 (d, 1H), 7.83 (m, 5H), 7.52 (m, 2H), 7.24 (m, 2H), 6.88 (m, 2H), 4.65 (m, 4H), 4.2 (m, 4H), 3.92 (m, 2H), 3.62-3.21 (m, 5H), 2.1-1.31 (m, 12H)

EXAMPLE 159

Preparation of 4-[N-[1-[N-(4-(2-pyrrolidinethoxy) benzoyl)amino]cyclohexanecarbonyl]amino]-1-(2-methanesulfonylphenyl)piperidin-3-one hydrochloride 50 ml of saturated hydrogenchloride-ethyl acetate solution was added to 4-[N-[1-[N-(4-(2-pyrrolidinethoxy)benzoyl)amino]cyclohexanecarbonyl]amino]-1-(2-methanesulfonylphenyl)piperidin-3-one (500 mg) obtained in Example 156. The reaction mixture was stirred for 2 hours at room temperature and filtered to give 320 ml of the titled compound as white solid.
$^1$H-NMR (400 MHz, CDCl$_3$) δ 8.05 (d, 1H), 7.8-7.52 (m, 7H), 7.24 (m, 2H), 6.68 (m, 2H), 4.89 (m, 1H), 2.85-3.6 (m, 8H), 2.18-1.15 (m, 12H)

EXAMPLE 160

Preparation of 4-[N-[1-[N-(4-(2-piperidinethoxy) benzoyl)amino]cyclohexanecarbonyl]amino]-1-(2-methanesulfonylphenyl)piperidin-3-one hydrochloride 50 ml of saturated hydrogenchloride-ethyl acetate solution was added to 4-[N-[1-[N-(4-(2-piperidinethoxy)benzoyl)amino]cyclohexanecarbonyl]amino]-1-(2-methanesulfonylphenyl)piperidin-3-one (500 mg) obtained in Example 157. The reaction mixture was stirred for 2 hours at room temperature and filtered to give 472 mg of the titled compound as white solid.
$^1$H-NMR (400 MHz, CDCl$_3$) δ 8.05 (d, 1H), 7.8-7.52 (m, 7H), 7.24 (m, 2H), 6.68 (m, 2H), 4.89 (m, 1H), 2.85-3.6 (m, 8H), 2.25 (m, 2H), 2.18-1.15 (m, 12H)

EXAMPLE 161

Preparation of 4-[N-[1-[N-(5-(2-morpholinethoxy) benzofuran-2-ylcarbonyl)amino]cyclohexanecarbonyl]amino]-1-(2-methanesulfonylphenyl)piperidin-3-one In accordance with the same procedure as in Example 76, except that 1-[N-(5-(2-morpholinethoxy)benzofuran-2-ylcarbonyl)amino]cyclohexanecarboxylic acid was used instead of 1-[N-(furan-2-ylcarbonyl)amino]cyclohexanecarboxylic acid in Step 3 thereof, 543 mg of the titled compound was prepared.
$^1$H-NMR (400 MHz, CDCl$_3$) δ 8.05 (m, 1H), 7.8 (m, 2H), 7.68-7.24 (m, 4H), 6.68 (m, 2H), 4.69 (m, 1H), 4.08 (m, 4H), 3.82-3.4 (m, 4H), 3.15 (s, 3H), 2.8 (m, 2H), 2.18-1.15 (m, 12H)

EXAMPLE 162

Preparation of 4-[N-[1-[N-(5-(2-pyrrolidinethoxy) benzofuran-2-ylcarbonyl)amino]cyclohexanecarbonyl]amino]-1-(2-methanesulfonylphenyl)piperidin-3-one In accordance with the same procedure as in Example 76, except that 1-[N-(5-(2-pyrrolidinethoxy)benzofuran-2-ylcarbonyl)amino]cyclohexanecarboxylic acid was used instead of 1-[N-(furan-2-ylcarbonyl)amino]cyclohexanecarboxylic acid in Step 3 thereof, 759 mg of the titled compound was prepared.

¹H-NMR (400 MHz, CDCl₃) δ 8.05 (m, 1H), 7.8 (m, 2H), 7.68-7.24 (m, 4H), 6.68 (m, 2H), 4.69 (m, 1H), 4.2 (m, 2H), 3.82-3.6 (dd, 2H), 3.15 (s, 3H), 2.8 (m, 2H), 2.18-1.15 (m, 12H)

EXAMPLE 163

Preparation of 4-[N-[1-[N-(5-(2-piperidinethoxy) benzofuran-2-ylcarbonyl)amino]cyclohexanecarbonyl]amino]-1-(2-methanesulfonylphenyl)piperidin-3-one In accordance with the same procedure as in Example 76, except that 1-[N-(5-(2-piperidinethoxy)benzofuran-2-ylcarbonyl)amino]cyclohexanecarboxylic acid was used instead of 1-[N-(furan-2-ylcarbonyl)amino]cyclohexanecarboxylic acid in Step 3 thereof, 990 mg of the titled compound was prepared.

¹H-NMR (400 MHz, CDCl₃) δ 8.05 (m, 1H), 7.8 (m, 2H), 7.68-7.24 (m, 4H), 6.68 (m, 2H), 4.69 (m, 1H), 4.2 (m, 2H), 3.82-3.6 (dd, 2H), 3.15 (s, 3H), 2.8 (m, 2H), 2.18-1.15 (m, 14H)

EXAMPLE 164

Preparation of 4-[N-[1-[N-(5-(2-morpholinethoxy) benzofuran-2-ylcarbonyl)amino]cyclohexanecarbonyl]amino]-1-(2-methanesulfonylphenyl)piperidin-3-one hydrochloride 50 ml of saturated hydrogenchloride-ethyl acetate solution was added to 4-[N-[1-[N-(5-(2-morpholinethoxy)benzofuran-2-ylcarbonyl)amino]cyclohexanecarbonyl]amino]-1-(2-methanesulfonylphenyl)piperidin-3-one (500 mg) obtained in Example 161. The reaction mixture was stirred for 2 hours at room temperature and filtered to give 472 mg of the titled compound as white solid.

¹H-NMR (400 MHz, CDCl₃) δ8.05 (d, 1H), 7.8 (d, 2H), 7.68-7.24 (m, 4H), 6.68 (d, 2H), 4.69 (m, 1H), 4.08 (m, 4H), 3.88 (m, 2H), 3.65 (m, 4H), 3.15-3.55 (m, 7H), 2.8 (m, 2H), 2.18-1.15 (m, 12H)

EXAMPLE 165

Preparation of 4-[N-[1-[N-(5-(2-pyrrolidinethoxy) benzofuran-2-ylcarbonyl)amino]cyclohexanecarbonyl]amino]-1-(2-methanesulfonylphenyl)piperidin-3-one hydrochloride 50 ml of saturated hydrogenchloride-ethyl acetate solution was added to 4-[N-[1-[N-(5-(2-pyrrolidinethoxy)benzofuran-2-ylcarbonyl)amino]cyclohexanecarbonyl]amino]-1-(2-methanesulfonylphenyl)piperidin-3-one (500 mg) obtained in Example 162. The reaction mixture was stirred for 2 hours at room temperature and filtered to give 130 mg of the titled compound as white solid.

¹H-NMR (400 MHz, CDCl₃) δ8.05 (d, 1H), 7.8 (d, 2H), 7.68-7.24 (m, 4H), 6.68 (d, 2H), 4.69 (m, 1H), 4.08 (m, 4H), 3.82 (dd, 2H), 3.15 (s, 3H), 2.18-1.15 (m, 12H)

EXAMPLE 166

Preparation of 4-[N-[1-[N-(5-(2-piperidinethoxy) benzofuran-2-ylcarbonyl)amino]cyclohexanecarbonyl]amino]-1-(2-methanesulfonylphenyl)piperidin-3-one hydrochloride 50 ml of saturated hydrogenchloride-ethyl acetate solution was added to 4-[N-[1-[N-(5-(2-piperidinethoxy)benzofuran-2-ylcarbonyl)amino]cyclohexanecarbonyl]amino]-1-(2-methanesulfonylphenyl)piperidin-3-one (500 mg) obtained in Example 163. The reaction mixture was stirred for 2 hours at room temperature and filtered to give 250 mg of the titled compound as white solid.

¹H-NMR (400 MHz, CDCl₃) δ8.05 (d, 1H), 7.68 (m, 1H), 7.66-7.34 (m, 4H), 7.11 (s, 1H), 6.68 (d, 2H), 4.69 (m, 1H), 4.48 (m, 1H), 3.82-3.34 (m, 8H), 3.15 (s, 3H), 2.8 (m, 2H), 2.18-1.15 (m, 12H)

EXAMPLE 167

Preparation of 4-[N-[1-[N-(4-(2-oxopyrrolidine) benzoyl)amino]cyclohexanecarbonyl]amino]-1-(2-methanesulfonylphenyl)piperidin-3-one In accordance with the same procedure as in Example 76, except that 1-[N-(4-(2-oxopyrrolidine)benzoyl)amino]cyclohexanecarboxylic acid was used instead of 1-[N-(furan-2-ylcarbonyl)amino]cyclohexanecarboxylic acid in Step 3 thereof, 770 mg of the titled compound was prepared.

¹H-NMR (400 MHz, CDCl₃) δ 8.05 (m, 1H), 7.78-7.24 (m, 8H), 6.65 (m, 1H), 4.69 (m, 1H), 3.92 (m, 2H), 3.82-3.6 (dd, 2H), 3.15 (s, 3H), 2.8 (m, 2H), 2.2-2.42 (m, 4H), 2.18-1.15 (m, 12H)

EXAMPLE 168

Preparation of 4-[N-[1-[N-(4-(2-oxopyrrolidine) furan-2-ylcarbonyl)amino]cyclohexanecarbonyl]amino]-1-(2-methanesulfonylphenyl)piperidin-3-one In accordance with the same procedure as in Example 76, except that 1-[N-(4-(2-oxopyrrolidine)furan-2-ylcarbonyl)amino]cyclohexane carboxylic acid was used instead of 1-[N-(furan-2-ylcarbonyl)amino]cyclohexanecarboxylic acid in Step 3 thereof, 770 mg of the titled compound was prepared.

¹H-NMR (400 MHz, CDCl₃) δ 8.05 (m, 1H), 7.65 (m, 1H), 7.38-7.14 (m, 3H), 6.48 (m, 1H), 4.69 (m, 1H), 4.2 (m, 2H), 3.82-3.6 (dd, 2H), 3.15 (s, 3H), 2.8 (m, 2H), 2.18-1.15 (m, 12H)

EXAMPLE 169

Preparation of 4-[N-[1-[N-(4-(2-morpholinethoxy) benzoyl)amino]cyclohexanecarbonyl]amino]-1-(4-fluoro-2-methanesulfonylaminophenyl)piperidin-3-one In accordance with the same procedure as in Example 76, except that 1-[N-(4-(2-morpholinethoxy)benzoyl)amino]cyclohexanecarboxylic acid was used instead of 1-[N-(furan-2-ylcarbonyl)amino]cyclohexanecarboxylic acid in Step 3 thereof and 2,5-difluoro-1-methanesulfonylbenzene was used instead of 1-fluorophenyl methyl sulfone in Step 5 thereof, 155 mg of the titled compound was prepared.

¹H-NMR (400 MHz, CDCl₃) δ 8.05 (d, 1H), 7.83 (m, 5H), 7.52 (m, 2H), 7.24 (m, 2H), 6.88 (m, 4H), 4.65 (m, 4H), 4.2 (m, 4H), 3.92 (m, 2H), 3.62-3.21 (m, 5H), 2.1-1.31 (m, 12H)

EXAMPLE 170

Preparation of 4-[N-[1-[N-(4-(2-morpholinethoxy) benzoyl)amino]cyclohexanecarbonyl]amino]-1-[4-fluoro-2-(pyrrolidin-2-one-1-yl)phenyl]piperidin-3-one In accordance with the same procedure as in Example 92, except that 4-[N-[1-[N-(4-(2-morpholinethoxy)benzoyl) amino]cyclohexanecarbonyl]amino]-1-[4-fluoro-2-(4-chlorobutyryl)aminophenyl]piperidin-3-ol was used instead of 4-[N-[1-[N-(furan-2-ylcarbonyl)amino]cyclohexanecarbonyl]amino]-1-[4-fluoro-2-(3-chloro-2,2-dimethylpropionyl) aminophenyl]piperidin-3-ol in Step 2 thereof, 130 mg of the titled compound was prepared.

$^1$H-NMR (400 MHz, CDCl$_3$) δ8.05 (d, 1H), 7.83 (m, 5H), 7.52 (m, 2H), 7.24 (m, 2H), 6.88 (m, 2H), 4.65 (m, 4H), 4.2 (m, 4H), 3.92 (m, 2H), 3.62-3.21 (m, 5H), 2.1-1.31 (m, 16H)

EXAMPLE 171

Preparation of 4-[N-[1-[N-(4-(dimethylamino)benzoyl)amino]cyclohexanecarbonyl]amino]-1-(4-fluoro-2-methanesulfonylphenyl)piperidin-3-one In accordance with the same procedure as in Example 76, except that 1-[N-(4-(dimethylamino)benzoyl)amino]cyclohexanecarboxylic acid was used instead of 1-[N-(furan-2-ylcarbonyl)amino]cyclohexanecarboxylic acid in Step 3 thereof and 2,5-difluorophenyl methane sulfone was used instead of 1-fluorophenyl methyl sulfone in Step 5 thereof, 222 mg of the titled compound was prepared.

$^1$H-NMR (400 MHz, CDCl$_3$) δ8.05 (d, 1H), 7.83 (m, 5H), 7.52 (m, 2H), 7.24 (m, 2H), 6.68 (d, 2H), 6.01 (s, 1H), 4.65 (m, 1H), 4.65-4.79 (dd, 2H), 3.25 (s, 3H), 3.05 (s, 6H), 2.1-1.31 (m, 12H)

EXAMPLE 172

Preparation of 4-[N-[1-[N-(4-(diethylamino)benzoyl)amino]cyclohexanecarbonyl]amino]-1-(4-fluoro-2-methanesulfonylphenyl)piperidin-3-one In accordance with the same procedure as in Example 76, except that 1-[N-(4-(diethylamino)benzoyl)amino]cyclohexanecarboxylic acid was used instead of 1-[N-(furan-2-ylcarbonyl)amino]cyclohexanecarboxylic acid in Step 3 thereof and 2,5-difluorophenyl methane sulfone was used instead of 1-fluorophenyl methane sulfone in Step 5 thereof, 332 mg of the titled compound was prepared.

$^1$H-NMR (400 MHz, CDCl$_3$) δ 8.05 (d, 1H), 7.83 (m, 5H), 7.52 (m, 2H), 7.24 (m, 2H), 6.68 (d, 2H), 6.01 (s, 1H), 4.68 (m, 1H), 4.65-4.79 (dd, 2H), 3.35 (m, 4H), 3.21 (s, 3H), 2.2-1.15 (m, 12H), 1.05 (m, 6H)

EXAMPLE 173

Preparation of 4-[N-[1-[N-(4-(dimethylamino)benzoyl)amino]cyclohexanecarbonyl]amino]-1-(4-fluoro-2-methanesulfonylphenyl)piperidin-3-one hydrochloride 50 ml of saturated hydrogenchloride-ethyl acetate solution was added to 4-[N-[1-[N-(4-(dimethylamino)benzoyl) amino]cyclohexanecarbonyl]amino]-1-(4-fluoro-2-methanesulfonylphenyl)piperidin-3-one (500 mg) obtained in Example 171. The reaction mixture was stirred for 2 hours at room temperature and filtered to give 250 mg of the titled compound as white solid.

$^1$H-NMR (400 MHz, CDCl$_3$) δ8.0-8.2 (m, 2H), 7.8-7.6 (m, 2H), 7.48 (m, 1H), 7.38 (m, 2H), 4.68 (m, 1H), 3.28 (s, 3H), 3.02-3.2 (m, 6H), 3.21 (s, 3H), 2.18-1.31 (m, 12H)

EXAMPLE 174

Preparation of 4-[N-[1-[N-(4-(diethylamino)benzoyl)amino]cyclohexanecarbonyl]amino]-1-(4-fluoro-2-methanesulfonylphenyl)piperidin-3-one hydrochloride 50 ml of saturated hydrogenchloride-ethyl acetate solution was added to 4-[N-[1-[N-(4-(diethylamino)benzoyl) amino]cyclohexanecarbonyl]amino]-1-(4-fluoro-2-methanesulfonylphenyl)piperidin-3-one (500 mg) obtained in Example 172. The reaction mixture was stirred for 2 hours at room temperature and filtered to give 440 mg of the titled compound as white solid.

$^1$H-NMR (400 MHz, CDCl$_3$) δ8.0-8.2(m, 2H), 7.8(m, 1H), 7.52(m, 2H), 7.41(m, 2H), 7.15 (s, 1H), 4.72 (s, 1H), 3.4 (m, 4H), 3.21 (s, 3H), 2.18-1.31(m, 12H), 1.1(m, 6H)

EXAMPLE 175

Preparation of 4-[N-[1-[N-(4-(3-phenylpropionyl) amino)cyclohexanecarbonyl]amino]-1-(2-methanesulfonylphenyl)piperidin-3-one In accordance with the same procedure as in Example 76, except that 1-[N-(4-(3-phenylpropionyl)amino)cyclohexane carboxylic acid was used instead of 1-[N-(furan-2-ylcarbonyl)amino]cyclohexanecarboxylic acid in Step 3 thereof, 132 mg of the titled compound was prepared.

$^1$H-NMR (400 MHz, CDCl$_3$) δ 7.63 (d, 1H), 7.48-7.00 (m, 8H), 5.10 (s, 2H), 4.68 (m, 1H), 3.58 (d, 1H), 3.48 (d, 1H), 3.46 (d, 1H), 3.23 (m, 2H), 2.99 (s, 3H), 2.75 (m, 3H), 2.33 (m, 4H), 2.04-1.97 (t, 2H), 1.81-1.72 (m, 4H), 1.52 (m, 2H), 1.21 (m, 1H)

EXAMPLE 176

Preparation of 4-[N-[1-[N-(2-methylcinnamoyl) amino]cyclohexanecarbonyl]amino]-1-(2-methanesulfonylphenyl)piperidin-3-one In accordance with the same procedure as in Example 76, except that 1-[N-(2-methylcinnamoyl)amino]cyclohexanecarboxylic acid was used instead of 1-[N-(furan-2-ylcarbonyl)amino]cyclohexanecarboxylic acid in Step 3 thereof, 450 mg of the titled compound was prepared.

$^1$H-NMR (400 MHz, CDCl$_3$) δ 8.10 (d, 1H), 7.68 (d, 1H), 7.34 (m, 8H), 5.99 (s, 1H), 4.71 (m, 1H), 4.09 (m, 1H), 3.78 (d, 1H), 3.67 (d, 1H), 3.63 (d, 1H), 3.20 (s, 3H), 2.78 (m, 1H), 2.25 (m, 2H), 2.15 (s, 3H), 1.89 (m, 3H), 1.66 (m, 4H), 1.38-1.26 (m, 3H)

EXAMPLE 177

Preparation of 4-[N-[1-[N-(benzyloxycarbonyl) amino]cyclohexanecarbonyl]amino]-1-(2-acetylamino) phenyl]piperidin-3-one In accordance with the same procedure as in Example 87, except that 4-[N-[1-[N-(benzyloxycarbonyl)amino]cyclohexanecarbonyl]amino]-3-piperidinol hydrochloride was used instead of 4-[N-[1-[N-(furan-2-ylcarbonyl)amino]cyclohexanecarbonyl]amino]-3-piperidinol hydrochloride in Step 1 thereof, and acetyl chloride was used instead of methoxyacetyl chloride in Step 3 of thereof, 670 mg of the titled compound was prepared.

$^1$H-NMR (400 MHz, CDCl$_3$) δ 7.56 (d, 1H), 7.48-6.95 (m, 8H), 5.10 (s, 2H), 4.68 (m, 1H), 3.58 (d, 1H), 3.48 (d, 1H), 3.46 (d, 1H), 3.23 (m, 2H), 2.75 (m, 1H), 2.33 (d, 2H), 2.04-1.97 (t, 2H), 1.81-1.72 (m, 4H), 1.52 (m, 2H), 1.21 (m, 1H)

EXAMPLE 178

Preparation of 4-[N-[1-[N-(benzyloxycarbonyl)amino]cyclohexanecarbonyl]amino]-1-(2-trifluoromethylphenyl)piperidin-3-one In accordance with the same procedure as in Example 24, except that 4-[N-[1-[N-(benzyloxycarbonyl)amino]cyclohexanecarbonyl]amino]-1-(4-fluoro-2-aminophenyl)piperidin-3-ol hydrochloride was used instead of 4-[N-[1-[N-(benzofuran-2-ylcarbonyl)amino]cyclohexanecarbonyl]amino]-3-piperidinol hydrochloride and 1-bromo-2-trifluoromethylbenzene was used instead of 1-bromo-4-fluoro-2-trifluoromethylbenzene in Step 1 of Example 24, 228 mg of the titled compound was prepared.

$^1$H-NMR (400 MHz, CDCl$_3$) δ 7.63 (d, 1H), 7.48-7.00 (m, 8H), 5.10 (s, 2H), 4.68 (m, 1H), 3.58 (d, 1H), 3.48 (d, 1H), 3.46 (d, 1H), 3.23 (m, 2H), 2.75 (m, 1H), 2.33 (d, 2H), 2.04-1.97 (t, 2H), 1.81-1.72 (m, 4H), 1.52 (m, 2H), 1.21 (m, 1H)

EXAMPLE 179

Preparation of 4-[N-[1-[N-(pyran-2-one-5-ylcarbonyl)amino]cyclohexanecarbonyl]amino]-1-(2-methanesulfonylphenyl)piperidin-3-one In accordance with the same procedure as in Example 76, except that 1-[N-(pyran-2-one-5-ylcarbonyl)amino]cyclohexanecarboxylic acid was used instead of 1-[N-(furan-2-ylcarbonyl)amino]cyclohexanecarboxylic acid in Step 3 thereof, 750 mg of the titled compound was prepared.

$^1$H-NMR (400 MHz, CDCl$_3$) δ 8.62 (broad, 1H), 8.10 (d, 1H), 7.67 (m, 2H), 7.38 (m, 2H), 7.30 (s, 1H), 7.20 (d, 1H), 6.89 (d, 1H), 5.71 (d, 1H), 4.71 (m, 1H), 4.09 (m, 1H), 3.78 (d, 1H), 3.67 (d, 1H), 3.63 (d, 1H), 2.78 (m, 1H), 2.15 (m, 2H), 1.89 (m, 3H), 1.66 (m, 4H), 1.38-1.26 (m, 3H),

EXAMPLE 180

Preparation of 4-[N-[1-[N-((6-methyl)-7H-imidazo[2,1-b]oxazol-5-ylcarbonyl)amino]cyclohexanecarbonyl]amino]-1-(2-methanesulfonylphenyl)piperidin-3-one In accordance with the same procedure as in Example 76, except that 1-[N-((6-methyl)-7H-imidazo[2,1-b]oxazol-5-ylcarbonyl)amino]cyclohexanecarboxylic acid was used instead of 1-[N-(furan-2-ylcarbonyl)amino]cyclohexanecarboxylic acid in Step 3 thereof, 59 mg of the titled compound was prepared.

$^1$H-NMR (400 MHz, CDCl$_3$) δ 8.24 (d, 1H), 8.10 (d, 1H), 7.68 (d, 1H), 7.42 (d, 1H), 7.38 (m, 2H), 6.89 (d, 1H), 4.76 (m, 1H), 3.78 (d, 1H), 3.64 (d, 1H), 3.56 (d, 1H), 3.19 (s, 3H), 2.78 (s, 3H), 2.15 (m, 2H), 1.89 (m, 3H), 1.66 (m, 4H), 1.38-1.26 (m, 3H)

EXAMPLE 181

Preparation of 4-[N-[1-[N-((6-methyl)-chromon-2-ylcarbonyl)amino]cyclohexanecarbonyl]amino]-1-(2-methanesulfonylphenyl)piperidin-3-one In accordance with the same procedure as in Example 76, except that 1-[N-((6-methyl)-chromon-2-ylcarbonyl)amino]cyclohexanecarboxylic acid was used instead of 1-[N-(furan-2-ylcarbonyl)amino]cyclohexanecarboxylic acid in Step 3 thereof, 82 mg of the titled compound was prepared.

$^1$H-NMR (400 MHz, CDCl$_3$) δ 8.54 (broad, 1H), 8.10 (d, 1H), 7.87 (s, 1H), 7.70 (s, 1H), 7.68 (d, 1H), 7.42 (d, 1H), 7.38 (m, 4H), 7.03 (s, 1H), 6.83 (s, 1H), 5.19 (m, 1H), 4.32 (m, 1H), 3.78 (d, 1H), 3.64 (d, 1H), 3.56(d, 1H), 3.19 (s, 3H), 2.78 (s, 3H), 2.15 (m, 2H), 1.89 (m, 3H), 1.66 (m, 4H), 1.38-1.26 (m, 3H)

EXAMPLE 182

Preparation of 4-[N-[1-[N-(isobutyryl)amino]cyclohexanecarbonyl]amino]-1-(2-methanesulfonylphenyl)piperidin-3-one In accordance with the same procedure as in Example 76, except that 1-[N-(isobutyryl)amino]cyclohexanecarboxylic acid was used instead of 1-[N-(furan-2-ylcarbonyl)amino]cyclohexanecarboxylic acid in Step 3 thereof, 382 mg of the titled compound was prepared.

$^1$H-NMR (400 MHz, CDCl$_3$) δ8.10 (d, 1H), 7.68 (d, 1H), 7.38 (m, 2H), 5.52 (s, 1H), 4.66 (m, 1H), 3.78 (d, 1H), 3.64 (d, 1H), 3.36(d, 1H), 3.27 (d, 1H), 3.19 (s, 3H), 2.78 (m, 1H), 2.44 (m, 1H), 2.17 (t, 2H), 1.89-1.71 (m, 3H), 1.69-1.49 (m, 3H), 1.34 (m, 3H), 1.18 (m, 7H)

EXAMPLE 183

Preparation of 4-[N-[1-[N-(isovaleryl)amino]cyclohexanecarbonyl]amino]-1-(2-methanesulfonylphenyl)piperidin-3-one In accordance with the same procedure as in Example 76, except that 1'-[N-(isovaleryl)amino]cyclohexanecarboxylic acid was used instead of 1-[N-(furan-2-ylcarbonyl)amino]cyclohexanecarboxylic acid in Step 3 thereof, 442 mg of the titled compound was prepared.

$^1$H-NMR (400 MHz, CDCl$_3$) δ 8.10 (d, 1H), 7.68 (d, 1H), 7.38 (m, 2H), 5.52 (s, 1H), 4.66 (m, 1H), 3.78 (d, 1H), 3.64 (d, 1H), 3.36(d, 1H), 3.27 (d, 1H), 3.19 (s, 3H), 2.78 (m, 1H), 2.17 (m, 4H), 1.89-1.71 (m, 3H), 1.69-1.49 (m, 4H), 1.37 (m, 3H), 0.99 (d, 6H)

EXAMPLE 184

Preparation of 4-[N-[1-[N-(3,3-dimethylacryloyl)amino]cyclohexanecarbonyl]amino]-1-(2-methanesulfonylphenyl)piperidin-3-one In accordance with the same procedure as in Example 76, except that 1-[N-(3,3-dimethylacryloyl)amino]cyclohexanecarboxylic acid was used instead of 1-[N-(furan-2-ylcarbonyl)amino]cyclohexanecarboxylic acid in Step 3 thereof, 442 mg of the titled compound was prepared.

$^1$H-NMR (400 MHz, CDCl$_3$) δ 8.10 (d, 1H), 7.68 (d, 1H), 7.38 (m, 2H), 5.06 (d, 1H, J=28 Hz), 4.66 (m, 1H), 3.78 (d, 1H), 3.64 (d, 1H), 3.52 (d, 1H), 3.20 (s, 3H), 2.78 (m, 1H), 2.17 (m, 2H), 1.89 (m, 6H), 1.69-1.49 (m, 5H), 1.37 (m, 3H),

EXAMPLE 185

Preparation of 4-[N-[1-[N-(2-methoxyacetyl)amino]cyclohexanecarbonyl]amino]-1-(2-methanesulfonylphenyl)piperidin-3-one In accordance with the same procedure as in Example 76, except that 1-[N-(2-methoxyacetyl)amino]cyclohexanecarboxylic acid was used instead of 1-[N-(furan-2-ylcarbonyl)amino]cyclohexanecarboxylic acid in Step 3 thereof, 872 mg of the titled compound was prepared.

$^1$H-NMR (400 MHz, CDCl$_3$) δ 8.10 (d, 1H), 7.68 (d, 1H), 7.38 (m, 2H), 6.68 (s, 1H), 4.66 (m, 1H), 3.94 (s, 2H), 3.78 (d, 1H), 3.64 (d, 1H), 3.49 (s, 3H), 3.27 (d, 1H), 3.19 (s, 3H), 2.78 (m, 1H), 2.17 (m, 2H), 1.89-1.71 (m, 4H), 1.69-1.49 (m, 4H), 1.37 (m, 4H)

EXAMPLE 186

Preparation of 4-[N-[1-[N-(cyclopropanecarbonyl)amino]cyclohexanecarbonyl]amino]-1-(2-methanesulfonylphenyl)piperidin-3-one In accordance with the same procedure as in Example 76, except that 1-[N-(cyclopropanecarbonyl)amino]cyclohexanecarboxylic acid was used instead of 1-[N-(furan-2-ylcarbonyl)amino]cyclohexanecarboxylic acid in Step 3 thereof, 731 mg of the titled compound was prepared.

$^1$H-NMR (400 MHz, CDCl$_3$) δ 8.10 (d, 1H), 7.68 (d, 1H), 7.38 (m, 2H), 5.74 (s, 1H), 4.71 (m, 1H), 3.78 (d, 1H), 3.64 (d, 1H), 3.20 (s, 3H), 2.78 (m, 1H), 2.12 (m, 2H), 1.89 (m, 3H), 1.66 (m, 4H), 1.43 (m, 4H), 0.99 (m, 2H), 0.78 (m, 2H)

EXAMPLE 187

Preparation of 4-[N-[1-[N-(cyclobutanecarbonyl)amino]cyclohexanecarbonyl]amino]-1-(2-methanesulfonylphenyl)piperidin-3-one In accordance with the same procedure as in Example 76, except that 1-[N-(cyclobutanecarbonyl)amino]cyclohexanecarboxylic acid was used instead of 1-[N-(furan-2-ylcarbonyl)amino]cyclohexanecarboxylic acid in Step 3 thereof, 639 mg of the titled compound was prepared.

$^1$H-NMR (400 MHz, CDCl$_3$) δ 8.10 (d, 1H), 7.68 (d, 1H), 7.38 (m, 2H), 5.52 (s, 1H), 4.66 (m, 1H), 3.78 (d, 1H), 3.64 (d, 1H), 3.36(d, 1H), 3.19 (s, 3H), 3.08 (m, 1H), 2.78 (m, 1H), 2.32 (m, 2H), 2.17 (m, 4H), 1.89-1.71 (m, 5H), 1.69-1.49 (m, 5H), 1.37 (m, 3H)

EXAMPLE 188

Preparation of 4-[N-[1-[N-(cyclopentanecarbonyl)amino]cyclohexanecarbonyl]amino]-1-(2-methanesulfonylphenyl)piperidin-3-one In accordance with the same procedure as in Example 76, except that 1-[N-(cyclopentanecarbonyl)amino]cyclohexanecarboxylic acid was used instead of 1-[N-(furan-2-ylcarbonyl)amino]cyclohexanecarboxylic acid in Step 3 thereof, 888 mg of the titled compound was prepared.

$^1$H-NMR (400 MHz, CDCl$_3$) δ 8.10 (d, 1H), 7.68 (d, 1H), 7.38 (m, 2H), 5.57 (s, 1H), 4.66 (m, 1H), 3.78 (d, 1H), 3.64 (d, 1H), 3.36(d, 1H), 3.19 (s, 3H), 3.08 (m, 1H), 2.78 (m, 1H), 2.22-2.15 (m, 2H), 1.92-1.58 (m, 16H), 1.35 (m, 4H)

EXAMPLE 189

Preparation of 4-[N-[1-[N-(cyclohexanecarbonyl)amino]cyclohexanecarbonyl]amino]-1-(2-methanesulfonylphenyl)piperidin-3-one In accordance with the same procedure as in Example 76, except that 1-[N-(cyclohexanecarbonyl)amino]cyclohexanecarboxylic acid was used instead of 1-[N-(furan-2-ylcarbonyl)amino]cyclohexanecarboxylic acid in Step 3 thereof, 565 mg of the titled compound was prepared.

$^1$H-NMR (400 MHz, CDCl$_3$) δ 8.10 (d, 1H), 7.68 (d, 1H), 7.38 (m, 2H), 5.57 (s, 1H), 4.66 (m, 1H), 3.78 (d, 1H), 3.64 (d, 1H), 3.36(d, 1H), 3.19 (s, 3H), 3.08 (m, 1H), 2.78 (m, 1H), 2.22-2.15 (m, 3H), 1.92-1.71 (m, 8H), 1.69-1.49 (m, 3H), 1.37-1.24 (m, 11H)

EXAMPLE 190

Preparation of 4-[N-[1-[N-((3-isobuthyloxy)propionyl)amino]cyclohexanecarbonyl]amino]-1-(2-methanesulfonylphenyl)piperidin-3-one In accordance with the same procedure as in Example 76, except that 1-[N-((3-isobuthyloxy)propionyl)amino]cyclohexanecarboxylic acid was used instead of 1-[N-(furan-2-ylcarbonyl)amino]cyclohexanecarboxylic acid in Step 3 thereof, 777 mg of the titled compound was prepared.

$^1$H-NMR (400 MHz, CDCl$_3$) δ 8.10 (d, 1H), 7.68 (d, 1H), 7.38 (m, 2H), 6.76 (s, 1H), 4.66 (m, 1H), 3.78 (m, 3H), 3.71 (d, 1H), 3.64(d, 1H), 3.31 (t, 2H), 3.20 (s, 3H), 3.08 (m, 1H), 2.78 (m, 1H), 2.57 (t, 2H), 2.22-2.15 (m, 2H), 1.92-1.72 (m, 4H), 1.66-1.51 (m, 4H), 1.40 (m, 3H), 0.99 (d, 6H)

EXAMPLE 191

Preparation of 4-[N-[1-[N-((3-benzyloxy)propionyl)amino]cyclohexanecarbonyl]amino]-1-(2-methanesulfonylphenyl)piperidin-3-one In accordance with the same procedure as in Example 76, except that 1-[N-((3-benzyloxy)propionyl)amino]cyclohexanecarboxylic acid was used instead of 1-[N-(furan-2-ylcarbonyl)amino]cyclohexanecarboxylic acid in Step 3 thereof, 337 mg of the titled compound was prepared.

$^1$H-NMR (400 MHz, CDCl$_3$) δ 8.62 (s, 1H), 8.10 (d, 1H), 7.6 (m, 2H), 7.38 (m, 7H), 6.60 (s, 1H), 4.63 (m, 3H), 3.82 (t, 2H), 3.78 (m, 3H), 3.71 (d, 1H), 3.64(d, 1H), 3.31 (t, 2H), 3.20 (s, 3H), 2.70 (m, 1H), 2.57 (t, 2H), 2.22-2.15 (m, 2H), 1.92-1.72 (m, 4H), 1.66-1.51 (m, 4H), 1.40 (m, 3H), 1.22 (d, 3H)

EXAMPLE 192

Preparation of 4-[N-[1-[N-((N-t-butoxycarbonyl)piperidin-4-ylcarbonyl)amino]cyclohexanecarbonyl]amino]-1-(2-methanesulfonylphenyl)piperidin-3-one In accordance with the same procedure as in Example 76, except that 1-[N-((N-t-butoxyacarbonyl)piperidin-4-ylcarbonyl)amino] cyclohexanecarboxylic acid was used instead of 1-[N-(furan-2-ylcarbonyl)amino]cyclohexanecarboxylic acid in Step 3 thereof, 442 mg of the titled compound was prepared.

$^1$H-NMR (400 MHz, CDCl$_3$) δ 8.10 (d, 1H), 7.68 (d, 1H), 7.38 (m, 2H), 5.55 (s, 1H), 4.96 (m, 1H), 4.19 (m, 2H), 3.97 (m, 3H), 3.38 (d, 1H), 3.29 (s, 3H), 3.18 (d, 1H), 2.81 (m,

6H), 2.61 (t, 1H), 2.56 (t, 1H), 2.17 (m, 6H), 1.82 (m, 6H), 1.57 (m, 6H), 1.45 (s, 9H), 1.30 (m, 3H) 2.78 (m, 1H), 2.22-2.15 (m, 2H), 1.92-1.58 (m, 16H), 1.35 (m, 4H)

Test 1: Inhibition of Cathepsin K Activity

Recombinant human cathepsin K was prepared in accordance with *Biol, Pharm. Bull,* 19(8), 1026-1031 (1996) and *J. Biol. Chem.* 271, 2126-2132 (1996). Stock solutions of 2.5 mM Z-Phe-Arg-AMC (BACHEM, 1-1160) and all inhibitors were prepared in dimethyl sulfoxide. In vitro assays for cathepsin K were conducted with 25 uM Z-Phe-Arg-AMC as a substrate at pH 5.5 in 100 mM Na acetate buffer containing 20 mM cysteine and 5 mM EDTA in the presence of 2% final concentration of DMSO. Reaction was initiated by the addition of enzyme to samples, which were then incubated for 1 hour at 37° C. The fluorescence was monitored at 460 nm (excitation wavelength 360 nm) using fluorescence plate reader.

The concentrations of the test compounds, which inhibit 50% of cathepsin K activity, are represented as $IC_{50}$ in Table 1.

TABLE 1

| Test Compound | $IC_{50}$(nM) |
| --- | --- |
| Example 1 | 8.17 |
| Example 2 | 5.97 |
| Example 5 | 5.05 |
| Example 6 | 2.69 |
| Example 7 | 6.24 |
| Example 8 | 10.4 |
| Example 15 | 1.45 |
| Example 16 | 10.8 |
| Example 19 | 4.41 |
| Example 26 | 19.9 |
| Example 27 | 8.07 |
| Example 34 | 1.93 |
| Example 35 | 2.35 |
| Example 36 | 2.13 |
| Example 37 | 3.78 |
| Example 41 | 7.73 |
| Example 42 | 3.87 |
| Example 43 | 4.97 |
| Example 44 | 4.96 |
| Example 45 | 6.80 |
| Example 48 | 0.67 |
| Example 49 | 0.45 |
| Example 50 | 1.20 |
| Example 51 | 4.11 |
| Example 53 | 1.22 |
| Example 54 | 6.09 |
| Example 56 | 1.62 |
| Example 58 | 4.82 |
| Example 67 | 4.77 |
| Example 68 | 3.12 |
| Example 69 | 1.59 |
| Example 70 | 1.73 |
| Example 75 | 0.51 |
| Example 76 | 8.17 |
| Example 77 | 5.97 |
| Example 80 | 5.05 |
| Example 83 | 2.69 |
| Example 84 | 6.24 |
| Example 85 | 10.4 |
| Example 92 | 1.45 |
| Example 95 | 10.8 |
| Example 99 | 4.41 |
| Example 106 | 19.9 |
| Example 107 | 8.07 |
| Example 114 | 1.93 |
| Example 116 | 2.35 |
| Example 117 | 2.13 |
| Example 121 | 7.73 |
| Example 122 | 3.87 |
| Example 123 | 4.97 |

TABLE 1-continued

| Test Compound | $IC_{50}$(nM) |
| --- | --- |
| Example 124 | 4.96 |
| Example 125 | 6.80 |
| Example 128 | 0.67 |
| Example 129 | 0.45 |
| Example 130 | 1.20 |
| Example 131 | 4.11 |
| Example 133 | 1.22 |
| Example 134 | 6.09 |
| Example 136 | 1.62 |
| Example 138 | 4.82 |
| Example 147 | 4.77 |
| Example 148 | 3.12 |
| Example 153 | 0.36 |
| Example 154 | 1.37 |
| Example 155 | 1.29 |
| Example 156 | 1.90 |
| Example 158 | 3.15 |
| Example 159 | 3.25 |
| Example 160 | 3.14 |
| Example 161 | 0.41 |
| Example 162 | 0.45 |
| Example 163 | 0.55 |
| Example 164 | 0.52 |
| Example 165 | 1.63 |
| Example 166 | 0.71 |
| Example 167 | 3.07 |
| Example 168 | 15.79 |
| Example 169 | 0.58 |
| Example 170 | 1.69 |
| Example 171 | 0.77 |
| Example 172 | 0.58 |
| Example 173 | 1.59 |
| Example 174 | 1.00 |

As shown in Table 1, the compounds of the present invention have a cathepsin K activity inhibition effect.

Test 2: Selectivity Study

Selectivity study for the compounds of the present invention was performed using cathepsin C (Sigma, C8511), cathepsin G (Calbiochem, 219373), cathepsin H (Calbiochem, 219388), cathepsin L (Calbiochem, 219402), and cathepsin S (Eur. J. Biochem. 236, 558 (1996) as enzyme sources.

1) Cathepsin C

Cathepsin C (Sigma, C8511) was dissolved in D.W. buffer (pH 5.5). All inhibitors were prepared in dimethyl sulfoxide (DMSO). In vitro assays for cathepsin C were conducted with Gly-Phe-pNA (Sigma, G-0142) as a substrate. Samples were pre-incubated for 10 minutes at 37° C. Reaction was initiated by the addition of enzyme to samples, which were then incubated for 1 hour at 37° C. The absorbance of p-nitroaniline released was monitored at 405 nm using spectrophotometer.

2) Cathepsin G

Cathepsin G (Calbiochem, 219373) was dissolved in 50 mM NaOAc and 150 mM NaCl buffer (pH 5.5). All inhibitors were prepared in dimethyl sulfoxide (DMSO). In vitro assays for cathepsin G were conducted with Suc-Ala-Ala-Pro-Phe-pNA (Calbiochem, 219407) as a substrate. Samples were pre-incubated for 10 minutes at 25° C. Reaction was initiated by the addition of enzyme to samples, which were then incubated for 1 hour at 25° C. The absorbance of p-nitroaniline released was monitored at 405 nm using spectrophotometer.

3) Cathepsin H

Cathepsin H (Calbiochem, 219388) was dissolved in 20 mM NaOAc, 1 mM EDTA-2Na and 100 mM NaCl buffer (pH 4.6). All inhibitors were prepared dimethyl sulfoxide (DMSO). In vitro assays for cathepsin H were conducted with L-Arg-pNA (BACHEM, 1-1160) as a substrate. Samples were pre-incubated for 5 minutes at 40° C. Reaction was initiated by the addition of enzyme to samples, which were then incubated for 1 hour at 40° C. The absorbance of p-nitroaniline released was monitored at 405 nm using spectrophotometer.

4) Cathepsin L

Cathepsin L (Calbiochem, 219402) was dissolved in 50 mM NaOAc buffer (pH 5.0). All inhibitors were prepared in dimethyl sulfoxide (DMSO). In vitro assays for cathepsin G were conducted with Z-Phe-Arg-AMC (BACHEM, 1-1160) as a substrate. Samples were pre-incubated for 5 minutes at 25° C. Reaction was initiated by the addition of enzyme to samples, which were then incubated for 1 hour at 25° C. The fluorescence of AMC (7-amino-4-methylcoumarin) was monitored at 460 nm (excitation wavelength 360 nm), using fluorescence spectrophotometer.

5) Cathepsin S

Recombinant human Cathepsin S (Eur. J. Biochem. 236, 558 (1996) was dissolved in 0.1 M NaOAc 1 mM EDTA-4Na buffer (pH 5.5). All inhibitors were prepared in dimethyl sulfoxide (DMSO). In vitro assays for cathepsin S were conducted with Z-Val-Val-AMC (BACHEM, 1-1160) as a substrate. Samples were pre-incubated for 10 minutes at 4° C. Reaction was initiated by the addition of enzyme to samples, which were then incubated for 30 minutes at 37° C. The florescence of AMC (7-amino-4-methylcoumarin) released was monitored at 465 nm (excitation wavelength 360 nm), using fluorescence spectrophotometer.

The concentrations of the test compounds, which inhibit 50% of cathepsin s C, G, H, L and S activity, are represented as $IC_{50}$ in Table 2.

TABLE 2

| Test Compound | Cathepsins ($IC_{50}$, nM) | | | | |
|---|---|---|---|---|---|
| | C | G | H | L | S |
| Example 1 | 382 | >240 | >240 | 138 | 133 |
| Example 2 | >1000 | >1000 | >1000 | 2100 | 2100 |
| Example 44 | 394 | >690 | >690 | 574 | 460 |
| Example 57 | >1000 | >1000 | >1000 | 285 | 731 |
| Example 60 | >1000 | >1000 | >1000 | 103 | >150 |
| Example 61 | >1000 | >1000 | >1000 | >300 | >300 |
| Example 62 | >1000 | >1000 | >1000 | >450 | >450 |
| Example 75 | >1000 | >1000 | >1000 | 32.5 | >150 |
| Example 76 | >2460 | >2460 | >2460 | 971 | 204 |
| Example 80 | >1000 | >1000 | >1000 | 381 | 109 |
| Example 83 | >810 | >810 | >810 | 352 | 177 |
| Example 84 | >1000 | >1000 | >1000 | 986 | 212 |
| Example 94 | >1000 | >1000 | >1000 | 1452 | 197 |
| Example 124 | >1000 | >1000 | >1000 | 69.6 | 124 |
| Example 147 | >1000 | >1000 | >1000 | 249 | 214 |
| Example 148 | >1000 | >1000 | >1000 | 178 | 141 |

As shown in Table 2, the compounds of the present invention have also a high selective inhibition effect against cathepsin K activity.

Test 3: Pharmacokinetic Study

The compounds of the present invention were orally administered to rat with 10 mg/kg dose. The pharmacokinetic data were as follows: $C_{max}$ of 500~4,000 ng/ml, AUC of 1,500~6,500 ng-hr/ml, and the half-life ($T_{1/2}$) of about 1~6 hours. The bioavailabilities of the compounds of the present invention by oral administrations, which were calculated after intravenous administrations of the same doses, were about 30% ~90%.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A compound of formula (I) or a pharmaceutically acceptable salt thereof:

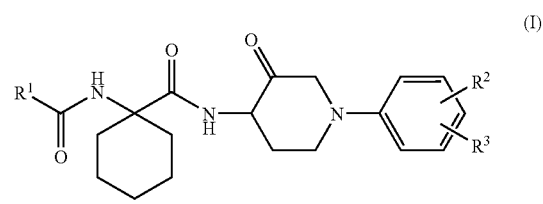

(I)

wherein:

$R^1$ is a $C_{1-6}$ alkyl group optionally substituted with phenyl, $C_{1-6}$ alkoxy, or benzyloxy; a $C_{2-6}$ alkenyl group optionally substituted with phenyl; a $C_{3-6}$ cycloalkyl group; a $C_{1-5}$ alkoxy group; a phenyl group substituted with halogen, phenyl, trifluoromethoxy, oxopyrrolidyl, mono- or di-$C_{1-4}$ alkylamino or $R^4$—$C_{1-4}$ alkoxy (wherein, $R^4$ is morpholine, pyrrolidine or piperidine); a furanyl group optionally substituted with one or more functional groups selected from the group consisting of $C_{1-6}$ alkyl, halogen, and oxopyrrolidyl; a benzofuranyl group optionally substituted with $C_{1-6}$ alkyl or $R^4$—$C_{1-4}$ alkoxy (wherein, $R^4$ is morpholine, pyrrolidine or piperidine); a thiophenyl group substituted with $C_{1-6}$ alkyl or halogen; a $C_{1-6}$ alkyl-isoxazolyl group; a pyridyl group optionally substituted with halogen; a morpholinyl group; a benzothiophenyl group; a quinolinyl group; a pyrazinyl group; a benzyloxy group; an oxopyranyl group; a $C_{1-6}$ alkyl-7H-imidazo[2,1-b]oxazolyl group; a $C_{1-6}$ alkyl-chromon-2-yl group; or a (N-t-butoxycarbonyl)piperidinyl group, and $R^2$ and $R^3$ are, each independently, hydrogen; hydroxy; nitro; halogen; cyano; a $C_{1-6}$ alkyl group optionally substituted with one or more halogen atoms; $C_{1-5}$ alkoxy; $C_{1-5}$ alkyl-thio; furyl; 1H-tetrazol-5-yl; oxazolyl; or a group selected from the formula consisting of (II), (III) and (IV):

(II)

(III)

(IV)

wherein, $R^5$ is hydrogen; hydroxy; $C_{1-6}$ alkyl; $C_{1-5}$ alkoxy; mono- or di-$C_{1-6}$ alkylamino; or $C_{3-6}$ cycloalkylamino, R⁶ is C₁₋₆ alkyl; phenyl optionally substituted with a C₁₋₄ alkoxy group; benzyl optionally substituted with a C₁₋₄ alkoxy group, R⁷ and R⁸ are, each independently, hydrogen; a C₁₋₆ alkylcarbonyl group optionally substituted with halogen, C₁₋₄ alkoxy, or phenyl; C₂₋₆ alkenylcarbonyl; C₁₋₄ alkoxycarbonyl; C₃₋₆ cycloalkylcarbonyl; benzoyl optionally substituted with one or more halogen atoms; mono- or di-C₁₋₄ alkylcarbamoyl; or C₁₋₄ alkylsulfonyl, or bonded each ether to form a morpholine, azetidin-2-one, 3,3-dimethylazetidin-2-one, pyrrolidin-2-one, pyrrole, 2,5-dihydropyrrole, piperidin-2-one, oxazolidin-2-one, imidazolidin-2-one, imidazolidin-2,5-dione, tetrazole, 1,1-dioxoisothiazolidine, or C₁₋₆ alkyl-aziridin-2-one ring, and n is 0, 1, or 2.

2. The compound of formula (I) or its pharmaceutically acceptable salt of claim 1, wherein R¹ is a furanyl group optionally substituted with C₁₋₆ alkyl, halogen, or oxopyrrolidyl; or a benzofuranyl group optionally substituted with C₁₋₆ alkyl or R⁴—C₁₋₄ alkoxy (wherein, R⁴ is morpholine, pyrrolidine or piperidine) and R² and R³ are, each independently, hydrogen; halogen; or a group of formula (III) or (IV).

3. The compound of formula (I) or its pharmaceutically acceptable salt thereof of claim 1, which is selected from the group consisting of:

4-[N-[1-[N-(benzofuran-2-ylcarbonyl)amino]cyclohexanecarbonyl]amino]-1-(2-methanesulfonylphenyl)piperidin-3-one;

4-[N-[1-[N-(benzofuran-2-ylcarbonyl)amino]cyclohexanecarbonyl]amino]-1-(2-nitrophenyl)piperidin-3-one;

4-[N-[1-[N-(benzofuran-2-ylcarbonyl)amino]cyclohexanecarbonyl]amino]-1-(4-fluoro-2-nitrophenyl)piperidin-3-one;

4-[N-[1-[N-(benzofuran-2-ylcarbonyl)amino]cyclohexanecarbonyl]amino]-1-(5-chloro-2-nitrophenyl)piperidin-3-one;

4-[N-[1-[N-(benzofuran-2-ylcarbonyl)amino]cyclohexanecarbonyl]amino]-1-(4-methanesulfonylphenyl)piperidin-3-one;

4-[N-[1-[N-(benzofuran-2-ylcarbonyl)amino]cyclohexanecarbonyl]amino]-1-(2-acetylphenyl)piperidin-3-one;

4-[N-[1-[N-(benzofuran-2-ylcarbonyl)amino]cyclohexanecarbonyl]amino]-1-(4-cyanophenyl)piperidin-3-one;

4-[N-[1-[N-(benzofuran-2-ylcarbonyl)amino]cyclohexanecarbonyl]amino]-1-(2-cyano-3-fluorophenyl)piperidin-3-one;

4-[N-[1-[N-(benzofuran-2-ylcarbonyl)amino]cyclohexanecarbonyl]amino]-1-(2-cyano-6-fluorophenyl)piperidin-3-one;

4-[N-[1-[N-(benzofuran-2-ylcarbonyl)amino]cyclohexanecarbonyl]amino]-1-(2-cyano-5-fluorophenyl)piperidin-3-one;

4-[N-[1-[N-(benzofuran-2-ylcarbonyl)amino]cyclohexanecarbonyl]amino]-1-(3-cyano-5-fluorophenyl)piperidin-3-one;

4-[N-[1-[N-(benzofuran-2-ylcarbonyl)amino]cyclohexanecarbonyl]amino]-1-(2-ethanesulfonylphenyl)piperidin-3-one;

4-[N-[1-[N-(benzofuran-2-ylcarbonyl)amino]cyclohexanecarbonyl]amino]-1-(4-acetylphenyl)piperidin-3-one;

4-[N-[1-[N-(benzofuran-2-ylcarbonyl)amino]cyclohexanecarbonyl]amino]-1-(4-formylphenyl)piperidin-3-one;

4-[N-[1-[N-(benzofuran-2-ylcarbonyl)amino]cyclohexanecarbonyl]amino]-1-(2-formylphenyl)piperidin-3-one;

4-[N-[1-[N-(benzofuran-2-ylcarbonyl)amino]cyclohexanecarbonyl]amino]-1-(4-nitrophenyl)piperidin-3-one;

4-[N-[1-[N-(benzofuran-2-ylcarbonyl)amino]cyclohexanecarbonyl]amino]-1-(3-methyl-4-nitrophenyl)piperidin-3-one;

4-[N-[1-[N-(benzofuran-2-ylcarbonyl)amino]cyclohexanecarbonyl]amino]-1-(3-fluoro-2-formylphenyl)piperidin-3-one;

4-[N-[1-[N-(benzofuran-2-ylcarbonyl)amino]cyclohexanecarbonyl]amino]-1-(3-chloro-2-formylphenyl)piperidin-3-one;

4-[N-[1-[N-(benzofuran-2-ylcarbonyl)amino]cyclohexanecarbonyl]amino]-1-(2-formyl-4-nitrophenyl)piperidin-3-one;

4-[N-[1-[N-(benzofuran-2-ylcarbonyl)amino]cyclohexanecarbonyl]amino]-1-(2-formyl-6-fluorophenyl)piperidin-3-one;

4-[N-[1-[N-(benzofuran-2-ylcarbonyl)amino]cyclohexanecarbonyl]amino]-1-(2-fluoro-3-formylphenyl)piperidin-3-one;

4-[N-[1-[N-(benzofuran-2-ylcarbonyl)amino]cyclohexanecarbonyl]amino]-1-(2-isopropylsulfonylphenyl)piperidin-3-one;

4-[N-[1-[N-(benzofuran-2-ylcarbonyl)amino]cyclohexanecarbonyl]amino]-1-(4-fluoro-2-trifluoromethylphenyl)piperidin-3-one;

4-[N-[1-[N-(benzofuran-2-ylcarbonyl)amino]cyclohexanecarbonyl]amino]-1-(2-cyanophenyl)piperidin-3-one;

4-[N-[1-[N-(benzofuran-2-ylcarbonyl)amino]cyclohexanecarbonyl]amino]-1-[2-(4-morpholino)phenyl]piperidin-3-one;

4-[N-[1-[N-(benzofuran-2-ylcarbonyl)amino]cyclohexanecarbonyl]amino]-1-(2-ethoxyphenyl)piperidin-3-one;

4-[N-[1-[N-(benzofuran-2-ylcarbonyl)amino]cyclohexanecarbonyl]amino]-1-(2-fluoro-4-trifluoromethylphenyl)piperidin-3-one;

4-[N-[1-[N-(benzofuran-2-ylcarbonyl)amino]cyclohexanecarbonyl]amino]-1-(2-chloro-4-trifluoromethylphenyl)piperidin-3-one;

4-[N-[1-[N-(benzofuran-2-ylcarbonyl)amino]cyclohexanecarbonyl]amino]-1-(2,4-dichlorophenyl)piperidin-3-one;

4-[N-[1-[N-(benzofuran-2-ylcarbonyl)amino]cyclohexanecarbonyl]amino]-1-(4-chloro-2-fluorophenyl)piperidin-3-one;

4-[N-[1-[N-(benzofuran-2-ylcarbonyl)amino]cyclohexanecarbonyl]amino]-1-(2-methoxy-5-cyanophenyl)piperidin-3-one;

4-[N-[1-[N-(benzofuran-2-ylcarbonyl)amino]cyclohexanecarbonyl]amino]-1-(4-cyano-2-fluorophenyl)piperidin-3-one;

4-[N-[1-[N-(benzofuran-2-ylcarbonyl)amino]cyclohexanecarbonyl]amino]-1-[2-(2-furyl)phenyl]piperidin-3-one;

4-[N-[1-[N-(benzofuran-2-ylcarbonyl)amino]cyclohexanecarbonyl]amino]-1-(2-bromophenyl)piperidin-3-one;

4-[N-[1-[N-(benzofuran-2-ylcarbonyl)amino]cyclohexanecarbonyl]amino]-1-(2-methylthiophenyl)piperidin-3-one;

4-[N-[1-[N-(benzofuran-2-ylcarbonyl)amino]cyclohexanecarbonyl]amino]-1-[2-(tert-butoxycarbonyl)phenyl]piperidin-3-one;

4-[N-[1-[N-(benzofuran-2-ylcarbonyl)amino]cyclohexanecarbonyl]amino]-1-(2-ethoxycarbonylphenyl)piperidin-3-one;

4-[N-[1-[N-(benzofuran-2-ylcarbonyl)amino]cyclohexanecarbonyl]amino]-1-(2-methoxyphenyl)piperidin-3-one;

4-[N-[1-[N-(benzofuran-2-ylcarbonyl)amino]cyclohexanecarbonyl]amino]-1-(4-fluoro-2-methylphenyl)piperidin-3-one;

4-[N-[1-[N-(benzofuran-2-ylcarbonyl)amino]cyclohexanecarbonyl]amino]-1-(2-isopropoxyphenyl)piperidin-3-one;

4-[N-[1-[N-(benzofuran-2-ylcarbonyl)amino]cyclohexanecarbonyl]amino]-1-(2-ethylthiophenyl)piperidin-3-one;

4-[N-[1-[N-(benzofuran-2-ylcarbonyl)amino]cyclohexanecarbonyl]amino]-1-[2-(3,3-dimethylazetidin-2-one-1-yl)phenyl]piperidin-3-one;

4-[N-[1-[N-(benzofuran-2-ylcarbonyl)amino]cyclohexanecarbonyl]amino]-1-[2-(pyrrolidin-2-one-1-yl)phenyl]piperidin-3-one;

4-[N-[1-[N-(benzofuran-2-ylcarbonyl)amino]cyclohexanecarbonyl]amino]-1-[2-(piperidin-2-one-1-yl)phenyl]piperidin-3-one;

4-[N-[1-[N-(benzofuran-2-ylcarbonyl)amino]cyclohexanecarbonyl]amino]-1-[2-(2-oxazolidinon-1-yl)phenyl]piperidin-3-one;

4-[N-[1-[N-(benzofuran-2-ylcarbonyl)amino]cyclohexanecarbonyl]amino]-1-[2-(2-imidazolidinon-1-yl)phenyl]piperidin-3-one;

4-[N-[1-[N-(benzofuran-2-ylcarbonyl)amino]cyclohexanecarbonyl]amino]-1-[2-[N-(ethoxycarbonyl)amino]phenyl]piperidin-3-one;

4-[N-[1-[N-(benzofuran-2-ylcarbonyl)amino]cyclohexanecarbonyl]amino]-1-[2-[N-(methoxycarbonyl)amino]phenyl]piperidin-3-one;

4-[N-[1-[N-(benzofuran-2-ylcarbonyl)amino]cyclohexanecarbonyl]amino]-1-[2-[N-(4-chlorobutyryl)amino]phenyl]piperidin-3-one;

4-[N-[1-[N-(benzofuran-2-ylcarbonyl)amino]cyclohexanecarbonyl]amino]-1-[2-[N-(isobutyryl)amino]phenyl]piperidin-3-one;

4-[N-[1-[N-(benzofuran-2-ylcarbonyl)amino]cyclohexanecarbonyl]amino]-1-[2-[N-(methoxyacetyl)amino]phenyl]piperidin-3-one;

4-[N-[1-[N-(benzofuran-2-ylcarbonyl)amino]cyclohexanecarbonyl]amino]-1-[2-[N-(cyclopropanecarbonyl)amino]phenyl]piperidin-3-one;

4-[N-[1-[N-(benzofuran-2-ylcarbonyl)amino]cyclohexanecarbonyl]amino]-1-[2-[N-(3-phenylpropionyl)amino]phenyl]piperidin-3-one;

4-[N-[1-[N-(benzofuran-2-ylcarbonyl)amino]cyclohexanecarbonyl]amino]-1-[2-[N-(2-fluorobenzoyl)amino]phenyl]piperidin-3-one;

4-[N-[1-[N-(benzofuran-2-ylcarbonyl)amino]cyclohexanecarbonyl]amino]-1-[2-[N-(acetyl)amino]phenyl]piperidin-3-one;

4-[N-[1-[N-(benzofuran-2-ylcarbonyl)amino]cyclohexanecarbonyl]amino]-1-[2-(2,5-dihydropyrrol-1-yl)phenyl]piperidin-3-one;

4-[N-[1-[N-(benzofuran-2-ylcarbonyl)amino]cyclohexanecarbonyl]amino]-1-[2-(tetrazol-1-yl)phenyl]piperidin-3-one;

4-[N-[1-[N-(benzofuran-2-ylcarbonyl)amino]cyclohexanecarbonyl]amino]-1-[2-(pyrrol-1-yl)-5-fluorophenyl]piperidin-3-one;

4-[N-[1-[N-(benzofuran-2-ylcarbonyl)amino]cyclohexanecarbonyl]amino]-1-[2-(pyrrol-1-yl)phenyl]piperidin-3-one;

4-[N-[1-[N-(benzofuran-2-ylcarbonyl)amino]cyclohexanecarbonyl]amino]-1-[2-(N,N-dimethylcarbamoyl)phenyl]piperidin-3-one;

4-[N-[1-[N-(benzofuran-2-ylcarbonyl)amino]cyclohexanecarbonyl]amino]-1-[2-(N-methylcarbamoyl)phenyl]piperidin-3-one;

4-[N-[1-[N-(benzofuran-2-ylcarbonyl)amino]cyclohexanecarbonyl]amino]-1-(2-carboxylphenyl)piperidin-3-one;

4-[N-[1-[N-(benzofuran-2-ylcarbonyl)amino]cyclohexanecarbonyl]amino]-1-(4-carboxyphenyl)piperidin-3-one;

4-[N-[1-[N-(benzofuran-2-ylcarbonyl)amino]cyclohexanecarbonyl]amino]-1-[2-(1,3-oxazol-5-yl)phenyl]piperidin-3-one;

4-[N-[1-[N-(benzofuran-2-ylcarbonyl)amino]cyclohexanecarbonyl]amino]-1-(2-hydroxyphenyl)piperidin-3-one;

4-[N-[1-[N-(benzofuran-2-ylcarbonyl)amino]cyclohexanecarbonyl]amino]-1-[2-(1H-tetrazol-5-yl)phenyl]piperidin-3-one;

4-[N-[1-[N-(benzofuran-2-ylcarbonyl)amino]cyclohexanecarbonyl]amino]-1-(2-methylsulfinylphenyl)piperidin-3-one;

4-[N-[1-[N-(benzofuran-2-ylcarbonyl)amino]cyclohexanecarbonyl]amino]-1-(2-ethylsulfinylphenyl)piperidin-3-one;

4-[N-[1-[N-(benzofuran-2-ylcarbonyl)amino]cyclohexanecarbonyl]amino]-1-(2-isopropylsulfinylphenyl)piperidin-3-one;

4-[N-[1-[N-(benzofuran-2-ylcarbonyl)amino]cyclohexanecarbonyl]amino]-1-[2-N-(acryloyl)aminophenyl]piperidin-3-one;

4-[N-[1-[N-(benzofuran-2-ylcarbonyl)amino]cyclohexanecarbonyl]amino]-1-[2-(3,3-dimethylureido)phenyl]piperidin-3-one;

4-[N-[1-[N-(benzofuran-2-ylcarbonyl)amino]cyclohexanecarbonyl]amino]-1-[2-(methoxycarbonyl)phenyl]piperidin-3-one;

4-[N-[1-[N-(benzofuran-2-ylcarbonyl)amino]cyclohexanecarbonyl]amino]-1-phenylpiperidin-3-one;

4-[N-[1-[N-(benzofuran-2-ylcarbonyl)amino]cyclohexanecarbonyl]amino]-1-[2-(1,1-dioxo-isothiazolin-2-yl)phenyl]piperidin-3-one;

4-[N-[1-[N-(furan-2-ylcarbonyl)amino]cyclohexylcarbonyl]amino]-1-(2-methanesulfonylphenyl)piperidin-3-one;

4-[N-[1-[N-(furan-2-ylcarbonyl)amino]cyclohexylcarbonyl]amino]-1-(3-fluoro-2-methanesulfonylphenyl)piperidin-3-one;

4-[N-[1-[N-(furan-2-ylcarbonyl)amino]cyclohexylcarbonyl]amino]-1-(4-fluoro-2-nitrophenyl)piperidin-3-one;

4-[N-[1-[N-(furan-2-ylcarbonyl)amino]cyclohexylcarbonyl]amino]-1-(4-fluoro-2-formylphenyl)piperidin-3-one;

4-[N-[1-[N-(furan-2-ylcarbonyl)amino]cyclohexylcarbonyl]amino]-1-(2-isopropylsulfonylphenyl)piperidin-3-one;

4-[N-[1-[N-(furan-2-ylcarbonyl)amino]cyclohexanecarbonyl]amino]-1-(2-phenylsulfonylphenyl)piperidin-3-one;
4-[N-[1-[N-(furan-2-ylcarbonyl)amino]cyclohexanecarbonyl]amino]-1-(2-(4-methoxybenzylsulfonylphenyl)piperidin-3-one;
4-[N-[1-[N-(furan-2-ylcarbonyl)amino]cyclohexylcarbonyl]amino]-1-(4-fluoro-2-methanesulfonylphenyl)piperidin-3-one;
4-[N-[1-[N-(furan-2-ylcarbonyl)amino]cyclohexylcarbonyl]amino]-1-(4-methoxy-2-methanesulfonylpheny)piperidin-3-one;
4-[N-[1-[N-(furan-2-ylcarbonyl)amino]cyclohexylcarbonyl]amino]-1-(4-fluoro-2-thiomethoxyphenyl)piperidin-3-one;
4-[N-[1-[N-(furan-2-ylcarbonyl)amino]cyclohexylcarbonyl]amino]-1-(2-cyanophenyl)piperidin-3-one;
4-[N-[1-[N-(furan-2-ylcarbonyl)amino]cyclohexylcarbonyl]amino]-1-(4-fluoro-2-methoxyacetylaminophenyl)piperidin-3-one;
4-[N-[1-[N-(furan-2-ylcarbonyl)amino]cyclohexylcarbonyl]amino]-1-(4-fluoro-2-methoxycarbonylaminophenyl)piperidin-3-one;
4-[N-[1-[N-(furan-2-ylcarbonyl)amino]cyclohexylcarbonyl]amino]-1-(4-fluoro-2-cyclopropylcarbonylaminophenyl)piperidin-3-one;
4-[N-[1-[N-(furan-2-ylcarbonyl)amino]cyclohexylcarbonyl]amino]-1-(4-fluoro-2-isobutyrylaminophenyl)piperidin-3-one;
4-[N-[1-[N-(furan-2-ylcarbonyl)amino]cyclohexylcarbonyl]amino]-1-[4-fluoro-2-(4-chlorobutyryl)aminophenyl]piperidin-3-one;
4-[N-[1-[N-(furan-2-ylcarbonyl)amino]cyclohexylcarbonyl]amino]-1-[4-fluoro-2-(3,3-dimethylazetidin-2-one-1-yl)phenyl]piperidin-3-one;
4-[N-[1-[N-(furan-2-ylcarbonyl)amino]cyclohexanecarbonyl]amino]-1-[4-fluoro-2-(3-methyl-aziridin-2-one-1-yl)phenyl]piperidin-3-one;
4-[N-[1-[N-(furan-2-ylcarbonyl)amino]cyclohexanecarbonyl]amino]-1-[4-fluoro-2-(azetidin-2-one-1-yl)phenyl]piperidin-3-one;
4-[N-[1-[N-(furan-2-ylcarbonyl)amino]cyclohexylcarbonyl]amino]-1-[4-fluoro-2-(pyrrolidin-2-one-1-yl)phenyl]piperidin-3-one;
4-[N-[1-[N-(furan-2-ylcarbonyl)amino]cyclohexanecarbonyl]amino]-1-[4-fluoro-2-(1,3-imidazolidin-2,5-dione-1-yl)phenyl]piperidin-3-one;
4-[N-[1-[N-(furan-2-ylcarbonyl)amino]cyclohexylcarbonyl]amino]-1-[4-fluoro-2-(1,1-dioxo-isothiazolidin-2-yl)phenyl]piperidin-3-one;
4-[N-[1-[N-(furan-2-ylcarbonyl)amino]cyclohexylcarbonyl]amino]-1-[4-fluoro-2-(piperidin-2-one-1-yl)phenyl]piperidin-3-one;
4-[N-[1-[N-(furan-2-ylcarbonyl)amino]cyclohexylcarbonyl]amino]-1-[4-fluoro-2-(pyrrol-1-yl)]piperidin-3-one;
4-[N-[1-[N-(furan-2-ylcarbonyl)amino]cyclohexylcarbonyl]amino]-1-[4-fluoro-2-(oxazol-4-yl)phenyl]piperidin-3-one;
4-[N-[1-[N-(furan-2-ylcarbonyl)amino]cyclohexylcarbonyl]amino]-1-[4-fluoro-2-(N-methylcarbamoyl)phenyl]piperidin-3-one;
4-[N-[1-[N-(furan-2-ylcarbonyl)amino]cyclohexylcarbonyl]amino]-1-[2-(N,N-dimethylcarbamoyl)phenyl]piperidin-3-one;
4-[N-[1-[N-(furan-2-ylcarbonyl)amino]cyclohexylcarbonyl]amino]-1-[2-(N-cyclopropylcarbamoyl)phenyl]piperidin-3-one;
4-[N-[1-[N-(5-methyl-isoxazol-3-ylcarbonyl)amino]cyclohexylcarbonyl]amino]-1-(2-aminophenyl)piperidin-3-one;
4-[N-[1-[N-(5-methyl-isoxazol-3-ylcarbonyl)amino]cyclohexylcarbonyl]amino]-1-(2-nitrophenyl)piperidin-3-one;
4-[N-[1-[N-(5-methyl-isoxazol-3-ylcarbonyl)amino]cyclohexylcarbonyl]amino]-1-(2-methanesulfonylphenyl)piperidin-3-one;
4-[N-[1-[N-(5-methyl-isoxazol-3-ylcarbonyl)amino]cyclohexylcarbonyl]amino]-1-(2-ethanesulfonylphenyl)piperidin-3-one;
4-[N-[1-[N-(5-methyl-isoxazol-3-ylcarbonyl)amino]cyclohexylcarbonyl]amino]-1-[4-fluoro-2-(3,3-dimethyl-azetidin-2-one-1-yl)phenyl]piperidin-3-one;
4-[N-[1-[N-(5-methyl-isoxazol-3-ylcarbonyl)amino]cyclohexylcarbonyl]amino]-1-[4-fluoro-2-(pyrrolidin-2-one-1-yl)phenyl]piperidin-3-one;
4-[N-[1-[N-(5-methyl-isoxazol-3-ylcarbonyl)amino]cyclohexylcarbonyl]amino]-1-[4-fluoro-2-(oxazolidin-2-one-3-yl)phenyl]piperidin-3-one;
4-[N-[1-[N-(5-methyl-isoxazol-3-ylcarbonyl)amino]cyclohexylcarbonyl]amino]-1-[4-fluoro-2-(imidazolidin-2-one-1-yl)phenyl]piperidin-3-one;
4-[N-[1-[N-(5-methyl-isoxazol-3-ylcarbonyl)amino]cyclohexylcarbonyl]amino]-1-[2-(3,3-dimethyl-azetidin-2-one-1-yl)phenyl]piperidin-3-one;
4-[N-[1-[N-(5-methyl-isoxazol-3-ylcarbonyl)amino]cyclohexylcarbonyl]amino]-1-[2-(pyrrolidin-2-one-1-yl)phenyl]piperidin-3-one;
4-[N-[1-[N-(5-chloro-thiophen-2-ylcarbonyl)amino]cyclohexylcarbonyl]amino]-1-(2-methanesulfonylphenyl)piperidin-3-one;
4-[N-[1-[N-(5-chloro-thiophen-2-ylcarbonyl)amino]cyclohexylcarbonyl]amino]-1-(2-ethanesulfonylphenyl)piperidin-3-one;
4-[N-[1-[N-(5-chloro-thiophen-2-ylcarbonyl)amino]cyclohexylcarbonyl]amino]-1-(2-isopropanesulfonylphenyl)piperidin-3-one;
4-[N-[1-[N-(5-chloro-thiophen-2-ylcarbonyl)amino]cyclohexylcarbonyl]amino]-1-(5-fluoro-2-methanesulfonylphenyl)piperidin-3-one;
4-[N-[1-[N-(5-methyl-thiophen-2-ylcarbonyl)amino]cyclohexylcarbonyl]amino]-1-(2-methanesulfonylphenyl)piperidin-3-one;
4-[N-[1-[N-(5-methyl-thiophen-2-ylcarbonyl)amino]cyclohexanecarbonyl]amino]-1-(2-isopropanesulfonylphenyl)piperidin-3-one;
4-[N-[1-[N-(5-methyl-thiophen-2-ylcarbonyl)amino]cyclohexylcarbonyl]amino]-1-(5-fluoro-2-methanesulfonylphenyl)piperidin-3-one;
4-[N-[1-[N-(3-methyl-thiophen-2-ylcarbonyl)amino]cyclohexylcarbonyl]amino]-1-(2-methanesulfonylphenyl)piperidin-3-one;
4-[N-[1-[N-(2-methyl-furan-3-ylcarbonyl)amino]cyclohexylcarbonyl]amino]-1-(2-methanesulfonylphenyl)piperidin-3-one;
4-[N-[1-[N-(5-methyl-furan-2-ylcarbonyl)amino]cyclohexylcarbonyl]amino]-1-(2-methanesulfonylphenyl)piperidin-3-one;
4-[N-[1-[N-(5-bromo-furan-2-ylcarbonyl)amino]cyclohexylcarbonyl]amino]-1-(2-methanesulfonyl-4-methoxyphenyl)piperidin-3-one;

4-[N-[1-[N-(4,5-dimethyl-furan-2-ylcarbonyl)amino]cyclohexylcarbonyl]amino]-1-(2-methanesulfonylphenyl)piperidin-3-one;
4-[N-[1-[N-(4,5-dimethyl-furan-2-ylcarbonyl)amino]cyclohexylcarbonyl]amino]-1-[2-(pyrrolidin-2-one-1-yl)phenyl]piperidin-3-one;
4-[N-[1-[N-(morpholin-4-ylcarbonyl)amino]cyclohexylcarbonyl]amino]-1-(2-methanesulfonylphenyl)piperidin-3-one;
4-[N-[1-[N-(benzothiophen-2-ylcarbonyl)amino]cyclohexylcarbonyl]amino]-1-(2-methanesulfonylphenyl)piperidin-3-one;
4-[N-[1-[N-(benzothiophen-2-ylcarbonyl)amino]cyclohexylcarbonyl]amino]-1-(2-tert-butoxycarbonylphenyl)piperidin-3-one;
4-[N-[1-[N-(benzothiophen-2-ylcarbonyl)amino]cyclohexylcarbonyl]amino]-1-(2-chloro-5-trifluoromethylphenyl)piperidin-3-one;
4-[N-[1-[N-(benzothiophen-2-ylcarbonyl)amino]cyclohexylcarbonyl]amino]-1-(4-chloro-2-fluoro-phenyl)piperidin-3-one;
4-[N-[1-[N-(benzothiophen-2-ylcarbonyl)amino]cyclohexylcarbonyl]amino]-1-(2-methylphenyl)piperidin-3-one;
4-[N-[1-[N-(3-methyl-benzofuran-2-ylcarbonyl)amino]cyclohexylcarbonyl]amino]-1-(2-methanesulfonylphenyl)piperidin-3-one;
4-[N-[1-[N-(3-methyl-benzofuran-2-ylcarbonyl)amino]cyclohexylcarbonyl]amino]-1-(5-fluoro-2-trifluoromethylphenyl)piperidin-3-one;
4-[N-[1-[N-(3-methyl-benzofuran-2-ylcarbonyl)amino]cyclohexylcarbonyl]amino]-1-(5-cyano-2-methoxyphenyl)piperidin-3-one;
4-[N-[1-[N-(quinolin-2-ylcarbonyl)amino]cyclohexylcarbonyl]amino]-1-(2-methanesulfonylphenyl)piperidin-3-one;
4-[N-[1-[N-(quinolin-2-ylcarbonyl)amino]cyclohexylcarbonyl]amino]-1-[2-(pyrrolidin-2-one-1-yl)phenyl]piperidin-3-one;
4-[N-[1-[N-(quinolin-2-ylcarbonyl)amino]cyclohexylcarbonyl]amino]-1-(2-nitrophenyl)piperidin-3-one;
4-[N-[1-[N-(pyrazin-2-ylcarbonyl)amino]cyclohexylcarbonyl]amino]-1-(2-methanesulfonylphenyl)piperidin-3-one;
4-[N-[1-[N-(pyrazin-2-ylcarbonyl)amino]cyclohexylcarbonyl]amino]-1-(2-methanesulfonylphenyl)piperidin-3-one dihydrochloride;
4-[N-[1-[N-(isonicotinylcarbonyl)amino]cyclohexylcarbonyl]amino]-1-(2-methanesulfonylphenyl)piperidin-3-one;
4-[N-[1-[N-(6-chloronicotinylcarbonyl)amino]cyclohexylcarbonyl]amino]-1-(2-methanesulfonylphenyl)piperidin-3-one;
4-[N-[1-[N-(6-chloronicotinylcarbonyl)amino]cyclohexylcarbonyl]amino]-1-(4-fluoro-2-nitrophenyl)piperidin-3-one;
4-[N-[1-[N-(pyridin-2-carbonyl)amino]cyclohexylcarbonyl]amino]-1-(2-methanesulfonylphenyl)piperidin-3-one;
4-[N-[1-[N-(pyridin-2-carbonyl)amino]cyclohexylcarbonyl]amino)-1-(2-methanesulfonylphenyl)piperidin-3-one hydrochloride;
4-[N-[1-[N-(4-fluorobenzoyl)amino]cyclohexylcarbonyl]amino]-1-(2-methanesulfonylphenyl)piperidin-3-one;
4-[N-[1-[N-(4-fluorobenzoyl)amino]cyclohexylcarbonyl]amino]-1-(4-fluoro-2-methanesulfonylphenyl)piperidin-3-one;
4-[N-[1-[N-(4-fluorobenzoyl)amino]cyclohexylcarbonyl]amino]-1-(2-methanesulfonyl-4-methoxyphenyl)piperidin-3-one;
4-[N-[1-[N-(4-fluorobenzoyl)amino]cyclohexanecarbonyl]amino]-1-(4-fluoro-2-trifluoromethylphenyl)piperidin-3-one;
4-[N-[1-[N-(4-fluorobenzoyl)amino]cyclohexanecarbonyl]amino]-1-[(2-(3-phenylpropionylamino)phenyl]piperidin-3-one;
4-[N-[1-[N-(4-fluorobenzoyl)amino]cyclohexanecarbonyl]amino]-1-[2-(cyclopropylamino)phenyl]piperidin-3-one;
4-[N-[1-[N-(4-fluorobenzoyl)amino]cyclohexanecarbonyl]amino]-1-[4-fluoro-2-(2,3,4-trifluorobenzoylamino)phenyl]piperidin-3-one;
4-[N-[1-[N-(4-biphenylcarbonyl)amino]cyclohexanecarbonyl]amino]-1-(2-methanesulfonylphenyl)piperidin-3-one;
4-[N-[1-[N-(4-trifluoromethylbenzoyl)amino]cyclohexanecarbonyl]amino]-1-(2-methanesulfonylphenyl)piperidin-3-one;
4-[N-[1-[N-(4-(2-morpholinethoxy)benzoyl)amino]cyclohexanecarbonyl]amino]-1-(2-methanesulfonylphenyl)piperidin-3-one;
4-[N-[1-[N-(4-(2-pyrrolidinethoxy)benzoyl)amino]cyclohexanecarbonyl]amino]-1-(2-methanesulfonylphenyl)piperidin-3-one;
4-[N-[1-[N-(4-(2-piperidinethoxy)benzoyl)amino]cyclohexanecarbonyl]amino]-1-(2-methanesulfonylphenyl)piperidin-3-one;
4-[N-[1-[N-(4-(2-morpholinethoxy)benzoyl)amino]cyclohexanecarbonyl]amino]-1-(2-methanesulfonylphenyl)piperidin-3-one hydrochloride;
4-[N-[1-[N-(4-(2-pyrrolidinethoxy)benzoyl)amino]cyclohexanecarbonyl]amino]-1-(2-methanesulfonylphenyl)piperidin-3-one hydrochloride;
4-[N-[1-[N-(4-(2-piperidinethoxy)benzoyl)amino]cyclohexanecarbonyl]amino]-1-(2-methanesulfonylphenyl)piperidin-3-one hydrochloride;
4-[N-[1-[N-(5-(2-morpholinethoxy)benzofuran-2-ylcarbonyl)amino]cyclohexanecarbonyl]amino]-1-(2-methanesulfonylphenyl)piperidin-3-one;
4-[N-[1-[N-(5-(2-pyrrolidinethoxy)benzofuran-2-ylcarbonyl)amino]cyclohexanecarbonyl]amino]-1-(2-methanesulfonylphenyl)piperidin-3-one;
4-[N-[1-[N-(5-(2-piperidinethoxy)benzofuran-2-ylcarbonyl)amino]cyclohexanecarbonyl]amino]-1-(2-methanesulfonylphenyl)piperidin-3-one;
4-[N-[1-[N-(5-(2-morpholinethoxy)benzofuran-2-ylcarbonyl)amino]cyclohexanecarbonyl]amino]-1-(2-methanesulfonylphenyl)piperidin-3-one hydrochloride;
4-[N-[1-[N-(5-(2-pyrrolidinethoxy)benzofuran-2-ylcarbonyl)amino]cyclohexanecarbonyl]amino]-1-(2-methanesulfonylphenyl)piperidin-3-one hydrochloride;
4-[N-[1-[N-(5-(2-piperidinethoxy)benzofuran-2-ylcarbonyl)amino]cyclohexanecarbonyl]amino]-1-(2-methanesulfonylphenyl)piperidin-3-one hydrochloride;
4-[N-[1-[N-(4-(2-oxopyrrolidine)benzoyl)amino]cyclohexanecarbonyl]amino]-1-(2-methanesulfonylphenyl)piperidin-3-one;
4-[N-[1-[N-(4-(2-oxopyrrolidine)furan-2-ylcarbonyl)amino]cyclohexanecarbonyl]amino]-1-(2-methanesulfonylphenyl)piperidin-3-one;
4-[N-[1-[N-(4-(2-morpholinethoxy)benzoyl)amino]cyclohexanecarbonyl]amino]-1-(4-fluoro-2-methanesulfonylaminophenyl)piperidin-3-one;

4-[N-[1-[N-(4-(2-morpholinethoxy)benzoyl)amino]cyclohexanecarbonyl]amino]-1-[4-fluoro-2-(pyrrolidin-2-one-1-yl)phenyl]piperidin-3-one;
4-[N-[1-[N-(4-(dimethylamino)benzoyl)amino]cyclohexanecarbonyl]amino]-1-(4-fluoro-2-methanesulfonylphenyl)piperidin-3-one;
4-[N-[1-[N-(4-(diethylamino)benzoyl)amino]cyclohexanecarbonyl]amino]-1-(4-fluoro-2-methanesulfonylphenyl)piperidin-3-one;
4-[N-[1-[N-(4-(dimethylamino)benzoyl)amino]cyclohexanecarbonyl]amino]-1-(4-fluoro-2-methanesulfonylphenyl)piperidin-3-one hydrochloride;
4-[N-[1-[N-(4-(diethylamino)benzoyl)amino]cyclohexanecarbonyl]amino]-1-(4-fluoro-2-methanesulfonylphenyl)piperidin-3-one hydrochloride;
4-[N-[1-[N-(3-phenylpropionyl)amino]cyclohexylcarbonyl]amino]-1-(2-methanesulfonylphenyl)piperidin-3-one;
4-[N-[1-[N-(2-methylcinnamoyl)amino]cyclohexanecarbonyl]amino]-1-(2-methanesulfonylphenyl)piperidin-3-one;
4-[N-[1-[N-(benzyloxycarbonyl)amino]cyclohexylcarbonyl]amino]-1-(2-acetylamino)piperidin-3-one;
4-[N-[1-[N-(benzyloxycarbonyl)amino]cyclohexylcarbonyl]amino]-1-(2-trifluoromethylphenyl)piperidin-3-one;
4-[N-[1-[N-(pyran-2-one-5-ylcarbonyl)amino]cyclohexanecarbonyl]amino]-1-(2-methanesulfonylphenyl)piperidin-3-one;
4-[N-[1-[N-((6-methyl)-7H-imidazo[2,1-b]oxazol-5-ylcarbonyl)amino]cyclohexanecarbonyl]amino]-1-(2-methanesulfonylphenyl)piperidin-3-one;
4-[N-[1-[N-((6-methyl)-chromon-2-ylcarbonyl)amino]cyclohexanecarbonyl]amino]-1-(2-methanesulfonylphenyl)piperidin-3-one;
4-[N-[1-[N-(isobutyryl)amino]cyclohexanecarbonyl]amino]-1-(2-methanesulfonylphenyl)piperidin-3-one;
4-[N-[1-[N-(isovaleryl)amino]cyclohexanecarbonyl]amino]-1-(2-methanesulfonylphenyl)piperidin-3-one;
4-[N-[1-[N-(3,3-dimethylacryloyl)amino]cyclohexanecarbonyl]amino]-1-(2-methanesulfonylphenyl)piperidin-3-one;
4-[N-[1-[N-(2-methoxyacetyl)amino]cyclohexanecarbonyl]amino]-1-(2-methanesulfonylphenyl)piperidin-3-one;
4-[N-[1-[N-(cyclopropanecarbonyl)amino]cyclohexanecarbonyl]amino]-1-(2-methanesulfonylphenyl)piperidin-3-one;
4-[N-[1-[N-(cyclobutanecarbonyl)amino]cyclohexanecarbonyl]amino]-1-(2-methanesulfonylphenyl)piperidin-3-one;
4-[N-[1-[N-(cyclopentanecarbonyl)amino]cyclohexanecarbonyl]amino]-1-(2-methanesulfonylphenyl)piperidin-3-one;
4-[N-[1-[N-(cyclohexanecarbonyl)amino]cyclohexanecarbonyl]amino]-1-(2-methanesulfonylphenyl)piperidin-3-one;
4-[N-[1-[N-((3-isobutyloxy)propionyl)amino]cyclohexanecarbonyl]amino]-1-(2-methanesulfonylphenyl)piperidin-3-one;
4-[N-[1-[N-((3-benzyloxy)propionyl)amino]cyclohexanecarbonyl]amino]-1-(2-methanesulfonylphenyl)piperidin-3-one; and
4-[N-[1-[N-((N-t-butoxycarbonyl)piperidin-4-ylcarbonyl)amino]cyclohexanecarbonyl]amino]-1-(2-methanesulfonylphenyl)piperidin-3-one.

4. A process for preparing a compound of formula (I) or a pharmaceutically acceptable salt thereof, which comprises oxidizing a compound of formula (V) with an oxidizing agent:

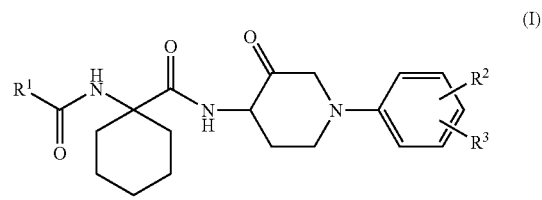

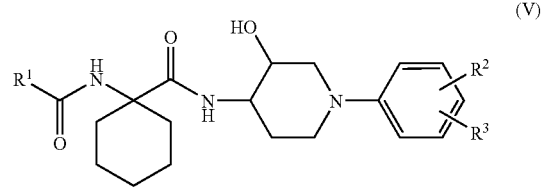

wherein, $R^1$, $R^2$, and $R^3$ are the same as defined in claim 1.

5. The process of claim 4, wherein the oxidizing agent is a pyridine-$SO_3$ complex, oxaryl chloride-dimethylsulfoxide, or pyridinium chlorochromate.

6. A compound of formula (V) or a pharmaceutically acceptable salt thereof:

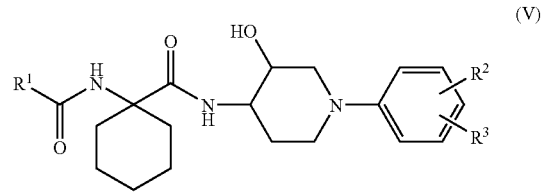

wherein, $R^1$, $R^2$, and $R^3$ are the same as defined in claim 1.

7. A process for preparing a compound of formula (V) or a pharmaceutically acceptable salt thereof, which comprises reacting a compound of formula (VI) with a compound of formula (VII):

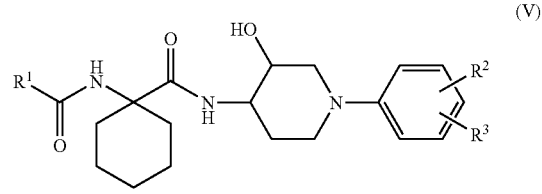

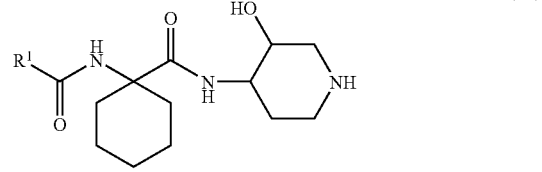

-continued

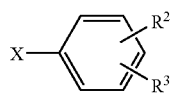 (VII)

wherein, $R^1$, $R^2$, and $R^3$ are the same as defined in claim 1; and X is halogen, nitro, $C_{1-7}$ alkylsulfonyl, or trifluorosulfonate.

8. The process of claim 7, wherein the reaction is carried out in the presence of a base and a palladium catalyst.

9. The process of claim 8, wherein the palladium catalyst is palladium diacetate (Pd(OAc)$_2$) or tris(dibenzylideneacetone)dipalladium (Pd$_2$(dba)$_2$).

10. A pharmaceutical composition for inhibiting cysteine proteases comprising a therapeutically effective amount of a compound of claim 1 or a pharmaceutically acceptable salt thereof, and a pharmaceutically acceptable carrier.

* * * * *